United States Patent
Meyer et al.

(10) Patent No.: US 10,213,394 B1
(45) Date of Patent: Feb. 26, 2019

(54) COMPOSITION AND METHOD FOR TREATING NEUROLOGICAL DISEASE

(71) Applicant: Osmotica Kereskedelmi és Szolgáltató Korlátolt Felelõsségû Társaság, Budapest (HU)

(72) Inventors: Glenn A. Meyer, Wilmington, NC (US); Joaquina Faour, Ciudad Autonoma de Buenos Aires (AR); Ana Cristina Pastini, Ciudad Autonoma de Buenos Aires (AR); Marcelo Fernando Befumo, Ciudad Autonoma de Buenos Aires (AR)

(73) Assignee: Osmotica Kereskedelmi és Szolgáltató Korlátolt Felelõsségû Társaság, Budapest (HU)

( * ) Notice: Subject to any disclaimer, the term of this patent is extended or adjusted under 35 U.S.C. 154(b) by 0 days.

(21) Appl. No.: 15/898,148

(22) Filed: Feb. 15, 2018

(51) Int. Cl.
| | |
|---|---|
| A61K 9/00 | (2006.01) |
| A61K 9/20 | (2006.01) |
| A61K 31/13 | (2006.01) |
| A61P 25/14 | (2006.01) |
| A61P 25/16 | (2006.01) |

(52) U.S. Cl.
CPC ............ *A61K 31/13* (2013.01); *A61K 9/0004* (2013.01); *A61K 9/0053* (2013.01); *A61K 9/20* (2013.01); *A61P 25/14* (2018.01); *A61P 25/16* (2018.01)

(58) Field of Classification Search
CPC .... A61K 31/13; A61K 31/198; A61K 31/197; A61K 9/20; A61K 9/0004; A61K 45/06; A61K 2300/00; A61P 25/16
See application file for complete search history.

(56) References Cited

U.S. PATENT DOCUMENTS

| | | |
|---|---|---|
| 3,878,276 A | 4/1975 | Hoernschemeyer |
| 3,977,404 A | 8/1976 | Theeuwes |
| 4,008,719 A | 2/1977 | Theeuwes et al. |
| 4,014,334 A | 3/1977 | Theeuwes et al. |
| 4,034,758 A | 7/1977 | Theeuwes |
| 4,036,227 A | 7/1977 | Zaffaroni et al. |
| 4,077,407 A | 3/1978 | Theeuwes et al. |
| 4,093,708 A | 6/1978 | Zaffaroni et al. |
| 4,777,049 A | 10/1988 | Magruder et al. |
| 4,870,174 A | 9/1989 | Paradies |
| 5,057,321 A | 10/1991 | Edgren et al. |
| 5,190,763 A | 3/1993 | Edgren et al. |
| 5,192,550 A | 3/1993 | Edgren et al. |
| 5,221,536 A | 6/1993 | Edgren et al. |
| 5,358,721 A | 10/1994 | Guittard et al. |
| 5,370,879 A | 12/1994 | Masterson et al. |
| 5,382,601 A | 1/1995 | Nuernberg et al. |
| 6,004,582 A | 12/1999 | Faour et al. |
| 6,194,000 B1 | 2/2001 | Smith et al. |
| 6,217,905 B1 | 4/2001 | Edgren et al. |
| 6,248,359 B1 | 6/2001 | Faour |
| 6,284,276 B1 | 9/2001 | Rudnic et al. |
| 6,352,721 B1 | 3/2002 | Faour |
| 6,491,949 B2 | 12/2002 | Faour et al. |
| 6,521,255 B2 | 2/2003 | Faour et al. |
| 6,569,456 B2 | 5/2003 | Faour et al. |
| 6,572,890 B2 | 6/2003 | Faour et al. |
| 6,599,284 B2 | 7/2003 | Faour |
| 6,599,532 B2 | 7/2003 | Faour et al. |
| 6,605,302 B2 | 8/2003 | Faour et al. |
| 6,613,357 B2 | 9/2003 | Faour et al. |
| 6,753,011 B2 | 6/2004 | Faour |
| 6,913,768 B2 | 7/2005 | Couch et al. |
| 8,252,331 B2 | 8/2012 | Meyer et al. |
| 8,293,799 B2 | 10/2012 | Feleder et al. |
| 8,329,217 B2 | 12/2012 | Vergez et al. |
| 8,389,578 B2 | 3/2013 | Went et al. |
| 8,574,626 B2 | 11/2013 | Vergez et al. |
| 8,591,947 B2 | 11/2013 | Vergez et al. |
| 8,637,080 B2 | 1/2014 | Pastini et al. |
| 8,685,451 B2 | 4/2014 | Toneguzzo et al. |
| 8,741,343 B2 | 6/2014 | Went et al. |
| 8,796,337 B2 | 8/2014 | Went et al. |
| 8,889,740 B1 | 11/2014 | Went et al. |
| 8,895,614 B2 | 11/2014 | Went et al. |
| 8,895,615 B1 | 11/2014 | Went et al. |
| 8,895,616 B1 | 11/2014 | Went et al. |
| 8,895,617 B1 | 11/2014 | Went et al. |
| 8,895,618 B1 | 11/2014 | Went et al. |
| 8,987,333 B2 | 3/2015 | Went et al. |
| 9,072,697 B2 | 7/2015 | Went et al. |
| 9,833,412 B2 | 12/2017 | Toneguzzo et al. |
| 9,867,791 B2 | 1/2018 | Went et al. |
| 9,867,792 B2 | 1/2018 | Went et al. |
| 9,867,793 B2 | 1/2018 | Went et al. |
| 9,877,933 B2 | 1/2018 | Went et al. |

(Continued)

FOREIGN PATENT DOCUMENTS

| | | |
|---|---|---|
| WO | WO-0038686 A1 | 7/2000 |
| WO | WO-0126663 A1 | 4/2001 |

(Continued)

OTHER PUBLICATIONS

Nishikawa (Parkinsonism and Related Disorders, 2009, p. 351-353). (Year: 2009).*

(Continued)

*Primary Examiner* — Umamaheswari Ramachandran
(74) *Attorney, Agent, or Firm* — Sterne, Kessler, Goldstein & Fox P.L.L.C.

(57) ABSTRACT

The present disclosure is directed to methods of treating neurological disorders in a patient such as Parkinson's disease, drug-induced extrapyramidal reactions, and/or levodopa-induced dyskinesia comprising administering to the patient once daily in the morning a pharmaceutical composition comprising about 50 mg to about 400 mg of extended-release amantadine or a pharmaceutically acceptable salt thereof.

28 Claims, 17 Drawing Sheets

(56) References Cited

U.S. PATENT DOCUMENTS

| | | |
|---|---|---|
| 2003/0045577 A1 | 3/2003 | Madhat |
| 2003/0211071 A1 | 11/2003 | Bologna et al. |
| 2004/0082543 A1 | 4/2004 | Cheung |
| 2004/0087658 A1 | 5/2004 | Moebius |
| 2005/0163851 A1 | 7/2005 | Feleder et al. |
| 2005/0267176 A1 | 12/2005 | Barberich |
| 2006/0063810 A1 | 3/2006 | Vergez et al. |
| 2006/0159763 A1 | 7/2006 | Meyer et al. |
| 2007/0077301 A1 | 4/2007 | Meyer et al. |
| 2008/0227743 A1 | 9/2008 | Nguyen et al. |
| 2008/0274061 A1 | 11/2008 | Schollmayer et al. |
| 2013/0115249 A1 | 5/2013 | Vergez et al. |
| 2013/0165517 A1 | 6/2013 | Went et al. |
| 2014/0242163 A1 | 8/2014 | Went et al. |
| 2015/0045438 A1 | 2/2015 | Went et al. |
| 2015/0045439 A1 | 2/2015 | Went et al. |
| 2015/0045446 A1 | 2/2015 | Went et al. |
| 2015/0045447 A1 | 2/2015 | Went et al. |
| 2015/0045448 A1 | 2/2015 | Went et al. |
| 2015/0051292 A1 | 2/2015 | Went et al. |
| 2015/0057355 A1 | 2/2015 | Went et al. |
| 2015/0119465 A1 | 4/2015 | Went et al. |
| 2015/0126612 A1 | 5/2015 | Went et al. |
| 2015/0157579 A1 | 6/2015 | Went et al. |
| 2016/0151307 A1 | 6/2016 | Went et al. |
| 2016/0256413 A1 | 9/2016 | Went et al. |
| 2016/0256414 A1 | 9/2016 | Went et al. |
| 2016/0263052 A1 | 9/2016 | Went et al. |
| 2016/0263053 A1 | 9/2016 | Went et al. |
| 2016/0263054 A1 | 9/2016 | Went et al. |
| 2016/0263055 A1 | 9/2016 | Went et al. |
| 2016/0263056 A1 | 9/2016 | Went et al. |
| 2016/0263057 A1 | 9/2016 | Went et al. |
| 2016/0263058 A1 | 9/2016 | Went et al. |
| 2017/0151183 A1 | 6/2017 | Went et al. |
| 2017/0151190 A1 | 6/2017 | Went et al. |

FOREIGN PATENT DOCUMENTS

| | | |
|---|---|---|
| WO | WO-0236099 A1 | 5/2002 |
| WO | WO-02100392 A1 | 12/2002 |
| WO | WO-2004012741 A1 | 2/2004 |
| WO | WO-2004087116 A2 | 10/2004 |
| WO | WO-2005072705 A1 | 8/2005 |
| WO | WO-2006058236 A2 | 6/2006 |
| WO | WO-2006089494 A1 | 8/2006 |

OTHER PUBLICATIONS

Chen et al. (Drug-Induced Movement Disorders: A primer, https://www.uspharmacist.com/article/drug-induced-movement-disorders-a-primer, 2007). (Year: 2007).*

Ahmed, A., et al., "Dissolution Rate Studies on Acetaminophen Tablets," Pakistan Journal of Pharmaceutical Sciences 13(2):39-43, Faculty of Pharmacy, University of Karachi, Pakistan (Jul. 2000).

Benjamin, C.L. Lai., et al., "Epidemiology of Parkinson's disease," BJCM 43(3):133-137, (Apr. 2001).

Bryson, Y.J., et al., "A Prospective Double-blind Study of Side Effects Associated With the Administration of Amantadine for Influenza a Virus Prophylaxis," The Journal of Infectious Diseases 141(5):543-547, Oxford University Press, United States (May 1980).

Costa, P., et al., "Modeling and Comparison of Dissolution Profiles," European Journal of Pharmaceutical Sciences 13(2):123-133, Elsevier Science B.V, Netherlands (May 2001).

Danielczyk, W., et al., "Twenty-five Years of Amantadine Therapy in Parkinson's Disease," Journal of neural transmission. Supplementum 46:399-405, Springer-Verlag, Austria (1995).

Emami, J., et al., "Formulation of Sustained—Release Lithium Carbonate Matrix Tablets: Influence of Hydrophilic Materials on the Release Rate and in Vitro-in Vivo Evaluation," Journal of Pharmacy and Pharmaceutical Sciences 7(3):338-344, The Society, Canada (Nov. 2004).

Endo Laboratories, SYMMETREL, Amantadine Hydrochloride, USP, Tablets and Syrup, Clinical Pharmacology, 2003, 12 pages.

Entsuah, R., et al., "A Benefit-risk Analysis of Once-daily Venlafaxine Extended Release (Xr) and Venlafaxine Immediate Release (Ir) in Outpatients With Major Depression," Psychopharmacology Bulletin 33(4):671-676, Public Health Service, United States (1997).

Flaherty, J.A., et al., "Mental Side Effects of Amantadine Therapy: Its Spectrum and Characteristics in a Normal Population," The Journal of Clinical Psychiatry 42(9):344-345, Physicians Postgraduate Press, United States (Sep. 1981).

Golden, R.N., et al., "Efficacy and Tolerability of Controlled-release and Immediate-release Paroxetine in the Treatment of Depression," The Journal of Clinical Psychiatry 63(7):577-584, Physicians Postgraduate Press, United States (Jul. 2002).

Hartshorne, N.J., et al., "Unexpected Amantadine Intoxication in the Death of a Trauma Patient," American Journal of Forensic Medicine and Pathology 16(4):340-343, Lippincott Williams & Wilkins, United States (Dec. 1995).

Hayden, F.G., et al., "Comparative Single-dose Pharmacokinetics of Amantadine Hydrochloride and Rimantadine Hydrochloride in Young and Elderly Adults," Antimicrobial Agents and Chemotherapy 28(2):216-221, American Society for Microbiology, United States (Aug. 1985).

Hayden, F.G., et al., "Differences in Side Effects of Amantadine Hydrochloride and Rimantadine Hydrochloride Relate to Differences in Pharmacokinetics," Antimicrobial Agents and Chemotherapy 23(3):458-464, American Society for Microbiology, United States (Mar. 1983).

Hesselink, M.B., et al., "Modifications of the Behavioral Profile of Non-competitive Nmda Receptor Antagonists, Memantine, Amantadine and (+)mk-801 After Chronic Administration," Behavioural Pharmacology 10(1):85-98, Lippincott Williams and Wilkins, England (Feb. 1999).

Keyser, L.A., et al., "Comparison of Central Nervous System Adverse Effects of Amantadine and Rimantadine Used as Sequential Prophylaxis of Influenza a in Elderly Nursing Home Patients," Archives of Internal Medicine 160(10):1485-1488, American Medical Association, United States (May 2000).

Lauritsen, B.J., et al., "Serum Lithium Concentrations Around the Clock With Different Treatment Regimens and the Diurnal Variation of the Renal Lithium Clearance," Acta Psychiatrica Scandinavica 64(4):314-319, Wiley-Blackwell, United States (Oct. 1981).

Metman, L.V, et al., "Amantadine for Levodopa-induced Dyskinesias: a 1-year Follow-up Study," Archives of Neurology 56(11):1383-1386, American Medical Association, United States, (Nov. 1999).

Minami, J., et al., "Comparison of Once-daily Nifedipine Controlled-release With Twice-daily Nifedipine Retard in the Treatment of Essential Hypertension," British Journal of Clinical Pharmacology 57(5):632-639, Wiley-Blackwell, England (May 2004).

Office Action dated Oct. 2, 2003 for united kingdom GB0217493.6.

Office Action dated Oct. 2, 2003 for united kingdom GB0313801.

Office Action dated Oct. 2, 2003 for united kingdom GB217492.8, 34 Pages.

Opie, L.H., et al., "Nifedipine and Mortality. Grave Defects in the Dossier," Circulation 92(5):1068-1073, Lippincott Williams & Wilkins, United States (Sep. 1995).

Pacifici, G.M., et al., "Effect of Amantadine on Drug-induced Parkisonism: Relationship Between Plasma Levels and Effect," British Journal of Clinical Pharmacology 3(5):883-889, Wiley-Blackwell, England (Oct. 1976).

PK-Merz, Summary of Product Characteristics, Qualitative and Quantitative Composition, Pharmaceutical Form, Film-coated tablet, Therapeutic indications, 8 pages.

Popik, P., et al., "Inhibition of Reinforcing Effects of Morphine and Motivational Aspects of Naloxone-Precipitated Opioid Withdrawal by N-Methyl-d-aspartate Receptor Antagonist, Memantine," The Journal of Pharmacology and Experimental Therapeutics 280(2):854-865, American Society for Pharmacology and Experimental Therapeutics, United States (Feb. 1997).

Schall, R., et al., "Bioequivalence of Controlled-release Calcium Antagonists," Clinical Pharmacokinectics 32(1):75-89, Part of Springer Science+business Media, Switzerland (Jan. 1997).

(56) References Cited

OTHER PUBLICATIONS

Schwab, R.S., et al., "Amantadine in Parkinson's Disease. Review of More Than Two Years' Experience," Journal of the American Medical Association 222(7):792-795, American Medical Association, United States (Nov. 1972).

Schwab, R.S., et al., "Amantadine in the Treatment of Parkinson's Disease," Journal of the American Medical Association 208(7):1168-1170, American Medical Association, United States (May 1969).

Smith, J.P., et al., "Amantadine Therapy for Chronic Hepatitis C: a Dose Escalation Study," The American Journal of Gastroenterology 99(6):1099-1104, Nature Publishing Group, United States (Jun. 2004).

Stanicova, A., et al., "Amantadine: An Antiviral and Antiparkinsonian Agent," Veterinary medicine 46(9-10):244-256, (Sep. 2001).

SYMMETREL, amantadine hydrochloride, Pharmacology, Parkinson's Disease, 1991, 14 pages.

Toal, C.B., "Formulation Dependent Pharmacokinetics—does the Dosage Form Matter for Nifedipine?" Journal of Cardiovascular Pharmacology 44(1):82-86, Lippincott Williams & Wilkins, United States, (Jul. 2004).

Troy, S.M., et al., "Bioavailability of Once-daily Venlafaxine Extended Release Compared With the Immediate-release Formulation in Healthy Adult Volunteers," Current Therapeutic Research 58(8):492-503, (Aug. 1997).

U.S. Appl. No. 60/633,319, filed Dec. 3, 2004, inventors Meyer, G.A, et al.

Vismari, L., et al., "Bioavailability of Immediate and Controlled Release Formulations of Lithium Carbonate," Brazilian Journal of Psychiatry 24(2):74-79, (Jun. 2002).

Warren, N., et al., "The Use of Amantadine in Parkinson's Disease and other Akinetic-Rigid Disorders," Advances in Clinical Neuroscience & Rehabilitation 4(5):38-41, (Nov./Dec. 2004).

Efficacy and Safety of Amantadine HC1 Extended Release Tablets in Parkinson's Disease Subjects with Levodopa-Induced Dyskinesias (ALLAY-LID II), ClinicalTrials.gov, accessed at https://clinicaltrials.gov/ct2/show/NCT02153645, accessed on Jun. 3, 2014, 7 pages.

Efficacy and Safety of Amantadine HC1 Extended Release Tablets in Parkinson's Disease Subjects with Levodopa-Induced Dyskinesias (ALLAY-LID I), ClinicalTrials.gov, https://clinicaltrials.gov/ct2/show/NCT02153645, accessed on Jun. 3, 2014, 7 pages.

Pahwa, R., et al., Randomized Trial of Extended Release Amantadine in Parkinson's Disease Patients with Levodopa-induced Dyskinesia (EASED Study), presented at the 17$^{th}$ International Congress of Parkinson's Disease and Movement Disorders (MDS), Jun. 16-20, 2013, 1 page.

SYMMETRL® (Amantadine Hydrochloride, USP) Tablets and Syrup, Jan. 2009, 15 pages.

Highlights of Prescribing Information, GOVOVRI™ (amantadine) extended release capsules, for oral use Initial U.S. Approval:1968, Aug. 2017, 19 pages.

* cited by examiner

COMPOSITION AND METHOD FOR TREATING NEUROLOGICAL DISEASE

FIELD OF THE INVENTION

This invention relates to compositions and methods for treating neurological disorders, such as Parkinson's disease, drug-induced extrapyramidal reactions, and levodopa-induced dyskinesia.

BACKGROUND OF THE INVENTION

A neurological disorder is any disorder of the nervous system, which can be categorized according to the primary location affected, the primary type of dysfunction involved, or the primary type of cause. The broadest division is between central nervous system disorders and peripheral nervous system disorders. Movement disorder is one of the sub-categories that involves the disorder of the central and/or peripheral nervous system such as Parkinson's disease, secondary Parkinsonism, essential tremor, amyotrophic lateral sclerosis, Tourette's Syndrome, multiple sclerosis, extrapyramidal movement disorders, and various types of Peripheral Neuropathy.

Among the various neurological disorders, Parkinson's Disease (PD) is a progressive, chronic, neurodegenerative disease characterized by impairment or death of neurons in the substantia nigra pars compacta. This neuronal deficit leads to motor symptoms including muscle rigidity, postural instability, tremor, akinesia or bradykinesia. In addition to the motor symptoms, most patients develop other health problems related to PD. These symptoms are diverse but are collectively known as non-motor symptoms and can likewise be troublesome and disabling. The average age of onset of PD is approximately 60 years. Parkinson's disease is the second most common neurodegenerative disease after Alzheimer's disease with an incidence of up to 1/1,000 person-years. The prevalence of PD in the United States (US) is 0.3%, which increases to 4-5% among people aged 85 years. Approximately 1,000,000 people in the US have PD. Levodopa is the most common drug prescribed to relieve the symptoms of PD. However, it is associated with motor and psychiatric side-effects. Consequently, interest has turned to alternative drugs with improved side-effect profiles to replace or augment levodopa. Amantadine, originally used as an antiviral drug, has been shown to improve the symptoms of PD.

Levodopa-induced dyskinesia is a form of dyskinesia associated with levodopa, used to treat Parkinson's disease. It often involves hyperkinetic movements, including chorea, dystonia, and athetosis. In the context of PD, dyskinesia is often the result of long-term dopamine therapy. These motor fluctuations occur in up to 80% of PD patients after 5-10 years of levodopa treatment, with the percentage of affected patients increasing over time. Amantadine has also been shown to improve levodopa-induced dyskinesia.

Drug-induced extrapyramidal reactions, also referred to as drug-induced extrapyramidal symptoms or drug-induced extrapyramidal side effects, are drug-induced movement disorders that include acute and tardive symptoms. These symptoms include dystonia (continuous spasms and muscle contractions), akathisia (motor restlessness), parkinsonism (characteristic symptoms such as rigidity), bradykinesia (slowness of movement), tremor, and tardive dyskinesia (irregular, jerky movements). Several types of drugs may cause drug-induced extrapyramidal reactions, such as antipsychotics, neuroleptic agents, antiemetics, and antidepressants. Levodopa has been previously tested for use in the treatment of drug-induced extrapyramidal syndrome but with a disappointing therapeutic response.

Amantadine hydrochloride, a noncompetitive NMDA receptor antagonist, is currently approved both as an immediate release product and as an extended release product in the US. The first New Drug Application for amantadine in the US was approved 40 years ago, with an indication for idiopathic PD and other forms of symptomatic parkinsonism. Amantadine has been shown in clinical studies to be an effective treatment to reduce motor fluctuations in patients with advanced PD. Amantadine has also been effective in treating drug-induced extrapyramidal reactions caused by administration of, for example, antipsychotics or drugs to slow the progression of PD. However, treatment with amantadine has previously been only with immediate release ("IR") amantadine as tablets, capsules or oral liquid or syrup. Administration of the IR form raised issues with patient compliance, because of the number of dosages required per day, and the negative side effects from use of the IR dosage form throughout the day.

To address the ongoing challenge of balancing the efficacies with the relative risk of adverse events, the inventors have developed a novel extended-release (ER) dosage form of amantadine. The extended-release dosage form and once daily morning dosing schedule were developed to provide more consistent levels of amantadine throughout the day and to enhance patient compliance by reducing administration from two or more times a day to once daily in the morning.

BRIEF SUMMARY OF THE INVENTION

The present disclosure provides a method of treating a patient with Parkinson's disease, the method comprising administering to the patient a pharmaceutical composition comprising amantadine, or a pharmaceutically acceptable salt thereof, in an extended release form, and amantadine, or a pharmaceutically acceptable salt thereof, in an immediate release form. In some embodiments, the patient is an adult.

The present disclosure also provides a method of treating drug-induced extrapyramidal reactions in a patient, the method comprising administering to the patient a pharmaceutical composition comprising amantadine, or a pharmaceutically acceptable salt thereof, in an extended release form, and amantadine, or a pharmaceutically acceptable salt thereof, in an immediate release form. In some embodiments, the patient is an adult.

The present disclosure also provides a method of treating levodopa-induced dyskinesia in a patient, the method comprising administering to the patient a pharmaceutical composition comprising amantadine, or a pharmaceutically acceptable salt thereof, in an extended release form, and amantadine, or a pharmaceutically acceptable salt thereof, in an immediate release form. In some embodiments, the patient is an adult.

The present disclosure also provides a method of treating one or more of Parkinson's disease, drug-induced extrapyramidal reactions, and levodopa-induced dyskinesia in a patient, the method comprising administering to the patient a pharmaceutical composition comprising amantadine, or a pharmaceutically acceptable salt thereof, in an extended release form, and amantadine, or a pharmaceutically acceptable salt thereof, in an immediate release form. In some embodiments, the patient is an adult.

In some embodiments, the pharmaceutical composition comprises about 50 mg to about 400 mg of amantadine or a pharmaceutically acceptable salt thereof. In some embodiments, the amantadine or a pharmaceutically acceptable salt thereof in an extended release form is from about 70 mg to about 300 mg. In some embodiments, the amantadine or a pharmaceutically acceptable salt thereof in an immediate release form is from about 40 mg to about 70 mg.

In some embodiments, at least about 50% of amantadine or a pharmaceutically acceptable salt thereof is in an extended release form. In one embodiment, between about 60% and about 82% of amantadine or a pharmaceutically acceptable salt thereof is in an extended release form.

In some embodiments, the composition is administered once daily in the morning.

In some embodiments, the pharmaceutical composition comprises about 129 mg to about 258 mg of amantadine free base equivalent.

In some embodiments, the pharmaceutical composition is a dosage form comprising 129 mg, 193 mg, or 258 mg of amantadine free base equivalent.

In some embodiments, the pharmaceutical composition is a dosage form comprising about 48 mg of amantadine free base equivalent, in an immediate release form.

In some embodiments, the pharmaceutically acceptable salt thereof is amantadine HCl.

In some embodiments, the pharmaceutical composition is a dosage form comprising 160 mg, 240 mg, or 320 mg of amantadine HCl.

In some embodiments, the dC/dT values of the pharmaceutical composition of the invention and the immediate release form are measured in the same pharmacokinetic study.

In some embodiments, the method comprises: i) administering to the patient a pharmaceutical composition comprising about 160 mg of amantadine or a pharmaceutically acceptable salt thereof for at least one week; and ii) increasing the dose of amantadine or a pharmaceutically acceptable salt thereof to a maximum daily dose of about 320 mg. In some embodiments, the dose is increased to about 240 mg of amantadine or a pharmaceutically acceptable salt thereof. In some embodiments, the dose increase is weekly. In one embodiment, each of the pharmaceutical compositions comprises an extended release component comprising amantadine or a pharmaceutically acceptable salt thereof; and an immediate release component comprising about 60 mg amantadine or a pharmaceutically acceptable salt thereof.

In some embodiments, the method comprises: i) administering to the patient a pharmaceutical composition comprising about 129 mg of amantadine free base equivalent for at least one week; and ii) increasing the dose of amantadine free base equivalent to a maximum daily dose of about 322 mg. In one embodiment, the maximum daily dose of about 322 mg comprises a pharmaceutical composition comprising about 129 mg of amantadine free base equivalent and a pharmaceutical composition comprising about 193 mg of amantadine free base equivalent. In some embodiments, the dose is increased to about 193 mg of amantadine free base equivalent. In some embodiments, the dose increase is weekly. In one embodiment, each of the pharmaceutical compositions comprises an extended release component comprising amantadine or a pharmaceutically acceptable salt thereof; and an immediate release component comprising about 48 mg amantadine free base equivalent.

In some embodiments, the method comprises: i) administering to the patient a pharmaceutical composition comprising about 129 mg of amantadine free base equivalent for at least one week; ii) increasing the dose of amantadine by administering to the patient a pharmaceutical composition comprising about 193 mg of amantadine free base equivalent. In some embodiments, each of the pharmaceutical compositions comprises an extended release component comprising amantadine free base equivalent; and an immediate release component comprising about 48 mg of amantadine free base equivalent. In some embodiments, the pharmaceutical composition is administered once daily in the morning.

In some embodiments, the method comprises: i) administering to the patient a pharmaceutical composition consisting essentially of about 129 mg of amantadine free base equivalent for at least one week; ii) increasing the dose of amantadine by administering to the patient a pharmaceutical composition consisting essentially of about 193 mg of amantadine free base equivalent. In some embodiments, each of the pharmaceutical compositions consists of an extended release component consisting essentially of amantadine free base equivalent and an immediate release component consisting essentially of about 48 mg of amantadine free base equivalent. In some embodiments, the pharmaceutical composition is administered once daily in the morning.

In some embodiments, the method comprises: i) administering to the patient a pharmaceutical composition comprising about 129 mg of amantadine free base equivalent for at least one week; ii) increasing the dose of amantadine by administering to the patient a pharmaceutical composition comprising about 193 mg of amantadine free base equivalent for at least one week; iii) increasing the dose of amantadine by administering to the patient a pharmaceutical composition comprising about 258 mg of amantadine free base equivalent.

In some embodiments, each of the pharmaceutical compositions comprises i) an extended release component comprising amantadine free base equivalent; and ii) an immediate release component comprising about 48 mg of amantadine free base equivalent. In some embodiments, the pharmaceutical compositions are administered once daily in the morning. In some embodiments, the method further comprises: iv) decreasing the dose of amantadine by administering to the patient a pharmaceutical composition comprising about 193 mg of amantadine free base equivalent for at least one week; and v) decreasing the dose of amantadine by administering to the patient a pharmaceutical composition comprising about 129 mg of amantadine free base equivalent for at least one week.

In some embodiments, the pharmaceutical composition provides a mean change in amantadine plasma concentration as a function of time (dC/dT) that is between about 40% and about 70% of the dC/dT provided by the same quantity of amantadine or a pharmaceutically acceptable salt thereof in an immediate release form, wherein the dC/dT values are measured in a single dose human pharmacokinetic study over the time period between 0 and 4 hours after administration.

In some embodiments, the $T_{max}$ of the pharmaceutical composition after a single-dose administration is between about 5 and about 12 hours.

In some embodiments, the median $T_{max}$ of the pharmaceutical composition after a single-dose administration is about 7.5 hours.

In some embodiments, the mean $C_{max}$ of the pharmaceutical composition after a single-dose administration is between about 540 and about 895 ng/ml.

In some embodiments, the mean $C_{max}$ of the pharmaceutical composition after a single-dose administration is between about 370 and about 550 ng/ml.

In some embodiments, the mean $C_{max}$ of the pharmaceutical composition after a single-dose administration is between about 265 and about 390 ng/ml.

In some embodiments, the mean $AUC_{0-\infty}$ of the pharmaceutical composition after a single-dose administration is between about 12,000 and about 26,000 ng·h/mL.

In some embodiments, the mean $AUC_{0-\infty}$ of the pharmaceutical composition after a single-dose administration is between about 8,000 and about 20,000 ng·h/mL.

In some embodiments, the mean $AUC_{0-\infty}$ of the pharmaceutical composition after a single-dose administration is between about 6,000 and about 12,000 ng·h/mL.

In some embodiments, the mean $AUC_{0-\infty}$ of the pharmaceutical composition after a single-dose administration is between about 6,900 and about 11,000 ng·h/mL.

In some embodiments, the mean $AUC_{0-\infty}$ of the pharmaceutical composition after a single-dose administration is between about 10,000 and about 40,000 ng·h/mL.

In some embodiments, the pharmaceutical composition has an in vitro dissolution profile ranging between about 0.1% to about 50% in about 0.5 hour, about 20% to about 80% in about 2.5 hours, about 40% to about 90% in about 4 hours, and no less than about 85% in about 8 hours as measured in water using a USP type II (paddle) dissolution system at 50 rpm, at a temperature of 37±0.5 C.

In one embodiment, the pharmaceutical composition has an in vitro dissolution profile ranging between about 28% to about 48% in about 0.5 hour, about 39% to about 63% in about 2.5 hours, about 61% to about 85% in about 4 hours, and no less than about 85% in about 8 hours as measured in water using a USP type II (paddle) dissolution system at 50 rpm, at a temperature of 37±0.5 C.

In another embodiment, the pharmaceutical composition has an in vitro dissolution profile ranging between about 15% to about 35% in about 0.5 hour, about 29% to about 53% in about 2.5 hours, about 53% to about 77% in about 4 hours, and no less than about 85% in about 8 hours as measured in water using a USP type II (paddle) dissolution system at 50 rpm, at a temperature of 37±0.5 C.

In yet another embodiment, the pharmaceutical composition has an in vitro dissolution profile ranging between about 9% to about 29% in about 0.5 hour, about 37% to about 62% in about 2.5 hours, about 59% to about 83% in about 4 hours, and no less than about 85% in about 8 hours as measured in water using a USP type II (paddle) dissolution system at 50 rpm, at a temperature of 37±0.5 C.

In some embodiments, the drug-induced extrapyramidal reaction is selected from the group consisting of dystonia, akathisia, parkinsonism, bradykinesia, tremor, and tardive dyskinesia, or any combination thereof.

In some embodiments, the drug-induced extrapyramidal reaction is caused by an antipsychotic, antiemetic, antidepressant, or any combination thereof. In one embodiment, the antipsychotic comprises haloperidol, fluphenazine, thilthixene, trifluoroperazine, acetophenazine, prochlorperazine, perphenazine, loxapine, chlorpromazine, triflupromazine, molindone, mesoridazine, chlorprothixene, thioridazine, clozapine or any combinations thereof. In one embodiment, the antiemetic comprises metoclopramide, trimethobenzamide or a combination thereof. In one embodiment, the antidepressant comprises selective serotonin reuptake inhibitors (SSRI), serotonin-norepinephrine reuptake inhibitors (SNRI), norepinephrine-dopamine reuptake inhibitors (NDRI) or any combination thereof.

In some embodiments, the patient continues to receive the antipsychotic, antiemetic, antidepressant, or any combination thereof.

In some embodiments, the method improves dyskinesia in a patient with levodopa-induced dyskinesia (LID) as determined by a reduction in a total Unified Dyskinesia Rating Scale (UdysRS) score after twelve weeks.

In some embodiments, the reduction in UdysRS score is between about −2 and about −7 after twelve weeks, compared to placebo.

In some embodiments, the reduction in UdysRS score is about −5 after twelve weeks, compared to placebo.

In some embodiments, the reduction in UdysRS score is between about −9 and about −17 after twelve weeks.

In some embodiments, the reduction in UdysRS score is about −13 after twelve weeks.

In some embodiments, the method increases the number of awake ON hours without dyskinesia in the patient.

In some embodiments, the method increases the number of awake ON hours without dyskinesia in the patient by about 1 to about 4 hours after twelve weeks.

In some embodiments, the method increases the number of awake ON hours without dyskinesia in the patient by about 4 hours after twelve weeks.

In some embodiments, the number of awake ON hours without dyskinesia in the patient is between about 9 and about 14 hours.

In some embodiments, the methods do not worsen Parkinson's disease symptoms in the patient.

In some embodiments, the methods do not worsen drug-induced extrapyramidal symptoms in the patient.

In some embodiments, the methods do not worsen levodopa-induced dyskinesia in the patient.

In some embodiments, the relative bioavailability of amantadine or a pharmaceutically acceptable salt thereof is approximately the same under fed and fasting conditions.

In some embodiments, the pharmaceutical composition is an osmotic device. In one embodiment, the osmotic devise comprises a semipermeable membrane.

In some embodiments, the osmotic device comprises: i) an extended release component comprising about 70 mg to about 300 mg of amantadine or a pharmaceutically acceptable salt thereof; and ii) an immediate release component comprising about 40 to about 70 mg of amantadine or a pharmaceutically acceptable salt thereof. In one embodiment, the pharmaceutical composition provides a mean change in amantadine plasma concentration as a function of time (dC/dT) that is between about 40% and about 70% of the dC/dT provided by the same quantity of amantadine or a pharmaceutically acceptable salt thereof in an immediate release form, wherein the dC/dT values are measured in a single dose human pharmacokinetic study over the time period between 0 and 4 hours after administration.

In some embodiments, the pharmaceutical composition is administered as a combination with a second agent. In some embodiments, the second agent further comprises one or more compounds selected from the group consisting of aromatic-L-amino-acid decarboxylase inhibitors, dopamine agonists, COMT (catechol O-methyltransferase) inhibitors, MAO-B (monoamine oxidase B) inhibitors, anticholinergics, benzodiazepines, SSRIs (selective serotonin reuptake inhibitors), tricyclic and tetracyclic antidepressants, non-steroidal anti-inflammatory agents, non-narcotic analgesic, narcotic analgesics, ADORA2A (adenosine A2A receptor) antagonists, anti-epileptic agents, and any combinations thereof.

DETAILED DESCRIPTION OF THE INVENTION

Definitions

Figure 1:
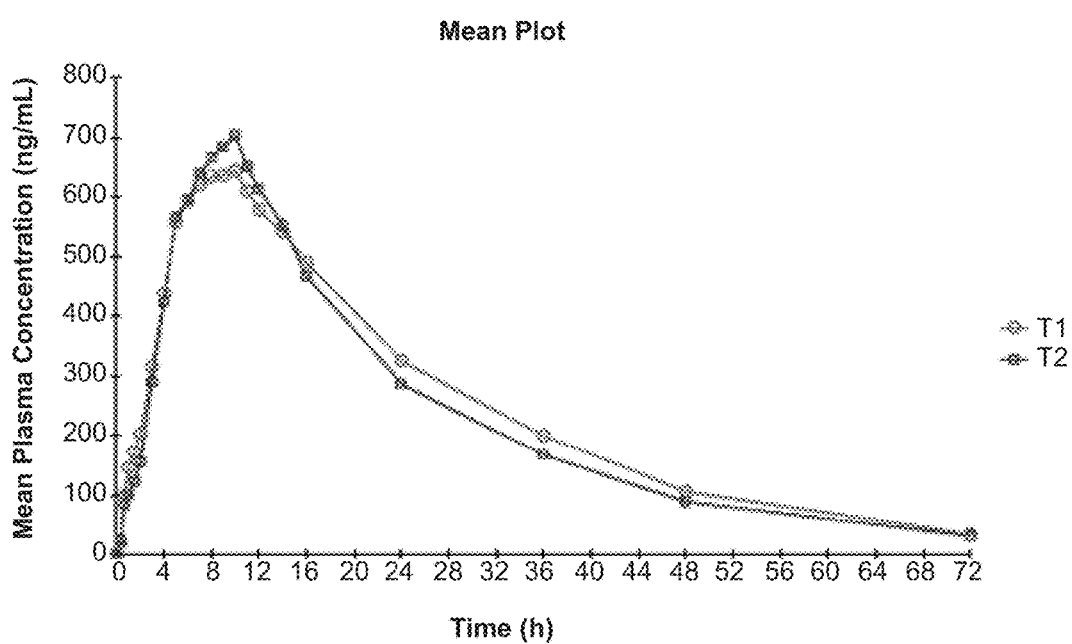
FIG. 1 depicts the amantadine plasma concentration-time (mean) profile following oral administration of one 320-mg Amantadine HCl ER Tablet under fasting (T1) or fed (T2) condition. Study III.

Unless defined otherwise, all technical and scientific terms used herein have the same meaning as commonly understood by one of ordinary skill in the art to which this disclosure belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference.

Although methods and materials similar or equivalent to those described herein can be used in practice or testing of the present disclosure, suitable methods and materials are described below. The materials, methods and examples are illustrative only and are not intended to be limiting. Other features and advantages of the disclosure will be apparent from the detailed description and from the claims.

In order to further define this disclosure, the following terms and definitions are provided.

The singular forms "a," "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

The term "about" is used herein to mean approximately, roughly, around, or in the regions of.

When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower).

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "immediate release" or "IR" as used herein means a release of an active agent to an environment over a period of seconds to no more than about 30 minutes once release has begun and release begins within a second to no more than about 15 minutes after administration.

The term "rapid release" as used herein means a release of an active agent to an environment over a period of 1 minute to one hour once release has begun and release can begin within a few minutes after administration or after expiration of a delay period (lag time) after administration.

The term "controlled release" as used herein means a release of an active agent to an environment over a period of about eight hours up to about 12 hours, 16 hours, 18 hours, 20 hours, a day, or more than a day. A controlled release can begin within a few minutes after administration or after expiration of a delay period (lag time) after administration.

The term "sustained release" as used herein means a controlled release of an active agent to maintain a constant drug level in the blood or target tissue of a subject to which the device is administered.

The term "extended release" or "ER" as used herein means a controlled release of an active agent from a dosage form to an environment over an extended period of time. As used herein, the term "extended release" profile assumes the definition as widely recognized in the art of pharmaceutical sciences. An extended release dosage form will release drug at substantially constant rate over an extended period of time or a substantially constant amount of drug will be released incrementally over an extended period of time. The term "extended release", as regards to drug release, includes the terms "prolonged release", "sustained release", or "slow release", as these terms are used in the pharmaceutical sciences.

The term "amantadine" as used herein refers to the free base or a pharmaceutically acceptable salt form of amantadine.

The term "free base" as used herein includes, but is not limited to, the unprotonated form of a therapeutic agent, molecule, or compound. Additionally, "free base" includes, but is not limited to, the neutral form of a molecule or compound.

The term "free base equivalent" as used herein refers to the salt form of a therapeutic agent, molecule, or compound that has the same molar quantity as its free base. For example, 60 mg amantadine HCl salt is 48 mg amantadine free base equivalent. 160 mg amantadine HCl salt is 129 mg amantadine free base equivalent. 240 mg amantadine HCl salt is 193 mg amantadine free base equivalent. 320 mg amantadine HCl salt is 258 mg amantadine free base equivalent. All numbers are rounded up to the nearest integer.

The term "unitary core" as used herein means the core of an osmotic device that is not divided into two or more layers or laminas. The core is considered to be the composition enclosed within the semipermeable membrane of the osmotic device.

The term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "effective amount" or "pharmaceutically effective amount" as used herein refers to the amount or quantity of a drug or pharmaceutically active substance which is sufficient to elicit the required or desired therapeutic response, or in other words, the amount which is sufficient to elicit an appreciable biological response when administered to a patient.

The term "unit dosage form" or "unit dose composition" as used herein refers to a device containing a quantity of the therapeutic compound, said quantity being such that one or more predetermined units may be provided as a single therapeutic administration.

The term "$C_{max}$" as used herein refers to the maximum plasma concentration of a drug after it is administered to a patient.

The term "$T_{max}$" as used herein refers to the time required to reach the maximal plasma concentration ("$C_{max}$") after administration of a drug.

The term "AUC" as used herein refers to the area under the curve of a plot of plasma concentration versus time following administration of a drug.

The term "$AUC_{0-t}$" as used herein refers to the area under the drug concentration-time curve from time zero to the time of the last measurable concentration ($C_1$).

The term "$AUC_{0-\infty}$" as used herein refers to the area under the drug concentration-time curve from time zero to infinity The term "dC/dT" as used herein refers to the change of plasma concentration of a drug over a prescribed time.

The term "steady state" as used herein means that the amount of the drug reaching the system is approximately the same as the amount of the drug leaving the system. Thus, at "steady-state," the patient's body eliminates the drug at approximately the same rate that the drug becomes available to the patient's system through absorption into the blood stream.

The term "LOCF" as used herein refers to last observation carried forward.

The term "treating" or "treatment" as used herein refers to the administration of a composition to a subject for therapeutic purposes.

The term "UDysRS" as used herein refers to the Unified Dyskinesia Ratings Scale.

The term "awake ON hours" or "awake 'ON' hours", as used herein, refers to time in which the medication has therapeutic benefits related to mobility, slowness and/or rigidity.

The term "awake OFF hours" or "awake 'OFF' hours" as used herein refers to time when a medication's therapeutic effect has diminished or stopped and no longer provides a benefit related to mobility, slowness and/or stiffness.

The term "mean" refers to an average value in a patient population. For example, a "mean Cmax" refers to an average of the maximum plasma concentrations of a drug in a patient population.

The term "adult" refers to a person 18 years of age or older.

Methods of Treatment

The present invention relates to a method of treating Parkinson's disease, comprising administering to the patient a pharmaceutical composition comprising 100 mg to 400 mg of amantadine or a pharmaceutically acceptable salt thereof. In some embodiments, the method comprises treating a patient with idiopathic Parkinson's disease, symptomatic parkinsonism, parkinsonism in association with cerebral arteriosclerosis, or any combination thereof.

The present invention also relates to a method of treating drug-induced extrapyramidal reactions in a patient, comprising administering to the patient a pharmaceutical composition comprising amantadine, or a pharmaceutically acceptable salt thereof, in an extended release form, and amantadine, or a pharmaceutically acceptable salt thereof, in an immediate release form.

The drug-induced extrapyramidal reactions may be caused by the previous or concomitant administration of drugs such as one or more antipsychotics, antidepressants, or other drugs to treat PD or symptoms of PD.

The present invention also relates to a method of treating levodopa-induced dyskinesia in a patient, comprising administering to the patient a pharmaceutical composition comprising amantadine, or a pharmaceutically acceptable salt thereof, in an extended release form, and amantadine, or a pharmaceutically acceptable salt thereof, in an immediate release form.

The present invention also relates to a method of treating one or more of Parkinson's disease, drug-induced extrapyramidal reactions, and levodopa-induced dyskinesia in a patient, comprising administering to the patient a pharmaceutical composition comprising amantadine, or a pharmaceutically acceptable salt thereof, in an extended release form, and amantadine, or a pharmaceutically acceptable salt thereof, in an immediate release form.

In some embodiments, the pharmaceutical composition is administered daily or once daily in the morning. In some embodiments, the pharmaceutical composition is administered daily or once daily in the afternoon. In some embodiments, the pharmaceutical composition is administered daily or once daily in the evening. In one embodiment, the pharmaceutical composition is administered more than 4 hours before bedtime.

In some embodiments, the patient is an adult.

In some embodiments of the invention, a pharmaceutically acceptable salt of amantadine is an inorganic acid salt. In some embodiments, the inorganic salt of amantadine is a mineral acid salt. In some embodiments, the inorganic salt of amantadine is a hydrochloride, a hydrobromide, a hydroiodide, a nitrate, a sulfate, a bisulfate, or a phosphate salt of amantadine. In one embodiment, the amantadine salt is a hydrochloride salt.

Dosing

In some embodiments, the amount of amantadine administered per day is from about 50 mg to about 1000 mg, from about 50 mg to about 900 mg, from about 50 mg to about 800 mg, from about 50 mg to about 700 mg, from about 50 mg to about 600 mg, from about 50 mg to about 500 mg, from about 50 mg to about 400 mg, from about 50 mg to about 300 mg, from about 50 mg to about 200 mg, or from about 50 mg to about 100 mg.

In some embodiments, the amount of amantadine administered per day is from about 100 mg to about 1000 mg, from about 100 mg to about 900 mg, from about 100 mg to about 800 mg, from about 100 mg to about 700 mg, from about 100 mg to about 600 mg, from about 100 mg to about 500 mg, from about 100 mg to about 400 mg, from about 100 mg to about 300 mg, or from about 100 mg to about 200 mg. In one embodiment, the amount of amantadine administered per day is from about 100 mg to about 400 mg. In another embodiment, the amount of amantadine administered per day is from about 160 mg to about 320 mg.

In some embodiments, the amount of amantadine free base equivalent administered per day is from about 100 mg to about 1000 mg, from about 100 mg to about 900 mg, from about 100 mg to about 800 mg, from about 100 mg to about 700 mg, from about 100 mg to about 600 mg, from about 100 mg to about 500 mg, from about 100 mg to about 400 mg, from about 100 mg to about 300 mg, or from about 100 mg to about 200 mg. In one embodiment, the amount of amantadine free base equivalent administered per day is from about 120 mg to about 300 mg. In another embodiment, the amount of amantadine free base equivalent administered per day is from about 130 mg to about 250 mg. In some embodiments, the amount of amantadine free base equivalent administered per day is from about 129 mg to about 258 mg. In some embodiments, the amount of amantadine free base equivalent administered per day is from 129 mg to 258 mg.

In some embodiments, the amount of amantadine administered per day is from about 100 mg to about 150 mg, from about 150 mg to about 200 mg, from about 200 mg to about 250 mg, from about 250 mg to about 300 mg, from about 300 mg to about 350 mg, from about 350 mg to about 400 mg. In one embodiment, the amount of amantadine administered per day is about 160 mg. In another embodiment, the amount of amantadine administered per day is about 240 mg. In another embodiment, the amount of amantadine administered per day is about 320 mg. In another embodiment, the amount of amantadine administered per day is 160 mg. In another embodiment, the amount of amantadine administered per day is 240 mg. In yet another embodiment, the amount of amantadine administered per day is 320 mg. In one embodiment, the amount of amantadine free base equivalent administered is 129 mg or about 129 mg. In one embodiment, the amount of amantadine free base equivalent administered per day is 129 mg or about 129 mg. In another embodiment, the amount of amantadine free base equivalent administered is 193 mg or about 193 mg. In another embodiment, the amount of amantadine free base equivalent administered per day is 193 mg or about 193 mg. In yet another embodiment, the amount of amantadine free base equivalent administered is 258 mg or about 258 mg. In yet another embodiment, the amount of amantadine free base equivalent administered per day is 258 mg or about 258 mg.

In some embodiments, the pharmaceutical composition comprises an extended release component comprising amantadine or a pharmaceutically acceptable salt thereof and an immediate release component comprising amantadine or a pharmaceutically acceptable salt thereof.

In some embodiments, the amount of amantadine in an extended release form administered per day is from about 50 mg to about 500 mg, from about 50 mg to about 400 mg, from about 50 mg to about 300 mg, from about 50 mg to about 200 mg, or from about 50 mg to about 100 mg.

In some embodiments, the amount of amantadine in the extended release form administered per day is from about 50 mg to about 500 mg, from about 50 mg to about 400 mg, from about 50 mg to about 300 mg, or from about 50 mg to about 200 mg. In one embodiment, the amount of amantadine in the extended release form administered per day is from about 70 mg to about 300 mg.

In some embodiments, the amount of amantadine in the extended release form administered per day is from about 50 mg to about 100 mg, from about 100 mg to about 150 mg, from about 150 mg to about 200 mg, from about 200 mg to about 250 mg, or from about 250 mg to about 300 mg. In one embodiment, the amount of amantadine in the extended release form administered per day is about 100 mg. In another embodiment, the amount of amantadine in the extended release form administered per day is about 180 mg. In another embodiment, the amount of amantadine in the extended release form administered per day is about 260 mg. In one embodiment, the amount of amantadine in the extended release form administered per day is about 81 mg of amantadine free base equivalent. In another embodiment, the amount of amantadine in the extended release form administered per day is about 145 mg of amantadine free base equivalent. In another embodiment, the amount of amantadine in the extended release form administered form per day is about 210 mg of amantadine free base equivalent.

In some embodiments, the amount of amantadine in the immediate release form administered per day is from about 20 mg to about 100 mg, from about 20 mg to about 90 mg, from about 20 mg to about 80 mg, from about 20 mg to about 70 mg, from about 20 mg to about 60 mg, from about 20 mg to about 50 mg, from about 20 mg to about 40 mg, or from about 20 mg to about 30 mg.

In some embodiments, the amount of amantadine in the immediate release form administered per day is from about 40 mg to about 100 mg, from about 40 mg to about 90 mg, from about 40 mg to about 80 mg, from about 40 mg to about 70 mg, or from about 40 mg to about 60 mg. In one embodiment, the amount of amantadine in the immediate release form administered per day is from about 40 mg to about 70 mg.

In some embodiments, the amount of amantadine in the immediate release form administered per day is from about 10 mg to about 20 mg, from about 20 mg to about 30 mg, from about 30 mg to about 40 mg, from about 40 mg to about 50 mg, from about 50 mg to about 60 mg, from about 60 mg to about 70 mg, from about 70 mg to about 80 mg, from about 80 mg to about 90 mg, or from about 90 mg to about 100 mg. In one embodiment, the amount of amantadine in the immediate release form administered per day is about 60 mg. In one embodiment, the amount of amantadine in the immediate release form administered per day is about 48 mg of amantadine free base equivalent.

In some embodiments, the amantadine administered is amantadine HCl. In one embodiment, the amount of amantadine HCl administered per day is about 160 mg, wherein the 160 mg amantadine HCl comprises about 100 mg amantadine HCl in the extended release form and about 60 mg amantadine HCl in the immediate release form. In another embodiment, the amount of amantadine HCl administered per day is about 240 mg, wherein the 240 mg amantadine HCl comprises about 180 mg amantadine HCl in the extended release form and about 60 mg amantadine HCl in the immediate release form. In another embodiment, the amount of amantadine HCl administered per day is about 320 mg, wherein the about 320 mg amantadine HCl comprises about 260 mg amantadine HCl in the extended release form and about 60 mg amantadine HCl in the immediate release form.

In some embodiments, the pharmaceutical composition is a dosage form comprising from about 100 mg to about 300 mg of amantadine free base equivalent. In one embodiment, the pharmaceutical composition is a dosage form comprising about 129 mg of amantadine free base equivalent (which equals about 160 mg of amantadine HCl). In another embodiment, the pharmaceutical composition is a dosage form comprising about 193 mg of amantadine free base equivalent (which equals about 240 mg of amantadine HCl). In one embodiment, the pharmaceutical composition is a dosage form comprising about 258 mg of amantadine free base equivalent (which equals about 320 mg of amantadine HCl).

In one embodiment, the pharmaceutical composition is a dosage form comprising about 81 mg of amantadine free base equivalent in extended release form and about 48 mg of amantadine free base equivalent in immediate release form. In another embodiment, the pharmaceutical composition is a dosage form comprising about 145 mg of amantadine free base equivalent in extended release form and about 48 mg of amantadine free base equivalent in immediate release form. In yet another embodiment, the pharmaceutical composition is a dosage form comprising about 210 mg of amantadine free base equivalent in extended release form and about 48 mg of amantadine free base equivalent in immediate release form.

Dosing Frequency and Dose Escalation

According to the present invention, a subject (e.g., human) having or at risk of having PD, is administered any of the pharmaceutical compositions described herein. In addition, according to the present invention, a subject (e.g., human) having or at risk of having a drug-induced extrapyramidal reaction, is administered any of the pharmaceutical compositions described herein.

In addition, according to the present invention, a subject (e.g., human) having or at risk of having levodopa-induced dyskinesia, is administered any of the pharmaceutical compositions described herein.

In some embodiments, the pharmaceutical compositions are administered at a constant, therapeutically-effective dose from the onset of therapy. For example, a pharmaceutical composition containing an extended release component and an immediate release component of amantadine may be administered three times per day, twice per day, or once per day in a unit dose comprising a total daily amantadine dose of about 50 mg, about 100 mg, about 200 mg, about 300 mg, about 400 mg, about 500 mg, about 600 mg, about 700 mg, or about 800 mg. In one embodiment, the pharmaceutical composition is administered once daily. In one embodiment, the pharmaceutical composition is administered in the morning. In one embodiment, the pharmaceutical composition is administered in the afternoon. In one embodiment, the pharmaceutical composition is administered in the evening.

In one embodiment, the pharmaceutical composition is administered more than 4 hours before bedtime. In some embodiments, a pharmaceutical composition containing an extended release component and an immediate release component of amantadine HCl may be administered twice per day or once per day in a unit dose comprising a total daily amantadine dose, or pharmaceutically acceptable salt thereof, of about 160 mg, about 240 mg, or about 320 mg.

In some embodiments, the pharmaceutical compositions are administered in a dose-escalating fashion. In some embodiments, the method of treatment comprises a Titration Period (the initial dose), a Maintenance Period, and/or a Taper Period.

In some embodiments, the Titration Period is in weekly intervals, from about one week to about four weeks, from about one week to about three weeks, from about one week to about two weeks, from about two weeks to about four weeks, from about two weeks to about three weeks, or from about three weeks to about four weeks. In some embodiments, the Titration Period is about one week, about two weeks, about three weeks, or about four weeks. In one embodiment, the Titration Period is about one week. In another embodiment, the Titration Period is about two weeks. In one embodiment, the Titration Period is one week. In another embodiment, the Titration Period is two weeks. In one embodiment, the patient is observed for the occurrence of hallucinations throughout treatment, especially at initiation and after dose increases. In some embodiments, the treatment should not be discontinued abruptly. The dose should be reduced gradually from higher doses to 129 mg daily for 1 to 2 weeks before discontinuing.

In some embodiments, the amount of amantadine administered per day is from about 50 mg to about 500 mg, from about 50 mg to about 400 mg, from about 50 mg to about 300 mg, or from about 50 mg to about 200 mg during the Titration Period. In one embodiment, the amount of amantadine administered per day is about 160 mg, or about 240 mg during the Titration Period. In another embodiment, the amount of amantadine administered is about 160 mg per day for one week, and then about 240 mg per day for one week, during the Titration Period. In one embodiment, the amount of amantadine free base equivalent administered per day is about 129 mg, or about 193 mg during the Titration Period. In another embodiment, the amount of amantadine administered is about 129 mg per day for one week, and then about 193 mg per day for one week, during the Titration Period. In one embodiment, the pharmaceutical composition is administered in the morning. In one embodiment, the pharmaceutical composition is administered in the afternoon. In one embodiment, the pharmaceutical composition is administered in the evening. In one embodiment, the pharmaceutical composition is administered more than 4 hours before bedtime.

In some embodiments, the Maintenance Period is from about 10 weeks to about 100 weeks, from about 10 weeks to about 70 weeks, from about 10 weeks to about 50 weeks, from about 10 weeks to about 30 weeks, from about 10 weeks to about 25 weeks, from about 10 weeks to about 20 weeks. In some embodiments, the Maintenance Period is at least 10 weeks. In some embodiments, the Maintenance Period is at least more than 10 weeks. In some embodiments, the Maintenance Period is at least 30 weeks. In one embodiment, the Maintenance Period is about 12 weeks. In another embodiment, the Maintenance Period is about 22 weeks.

In some embodiments, the amount of amantadine administered per day is from about 50 mg to about 500 mg, from about 50 mg to about 400 mg, from about 50 mg to about 300 mg, or from about 50 mg to about 200 mg during the Maintenance Period. In one embodiment, the amount of amantadine administered per day is about 160 mg, about 240 mg, or about 320 mg during the Maintenance Period. In another embodiment, the amount of amantadine free base equivalent administered per day is about 129 mg, about 193 mg, or about 258 mg during the Maintenance Period.

In some embodiments, the Taper Period is from about one week to about four weeks, from about one week to about three weeks, from about one week to about two weeks, from about two weeks to about four weeks, from about two weeks to about three weeks, or from about three weeks to about four weeks. In some embodiments, the Taper Period is about one week, about two weeks, about three weeks, or about four weeks. In one embodiment, the Taper Period is about one week. In another embodiment, the Taper Period is about two weeks.

In some embodiments, the amount of amantadine administered per day is from about 20 mg to about 300 mg, from about 20 mg to about 250 mg, from about 20 mg to about 200 mg, or from about 20 mg to about 100 mg during the Taper Period. In one embodiment, the amount of amantadine administered per day is about 160 mg, or about 240 mg during the Taper Period. In another embodiment, the amount of amantadine administered is about 240 mg per day for one week, and then about 160 mg per day for one week, during the Taper Period. In one embodiment, the amount of amantadine free base equivalent administered per day is about 129 mg, or about 193 mg during the Taper Period. In another embodiment, the amount of amantadine free base equivalent administered is about 193 mg per day for one week, and then about 129 mg per day for one week, during the Taper Period. In one embodiment, the pharmaceutical composition is administered in the morning. In one embodiment, the pharmaceutical composition is administered in the afternoon. In one embodiment, the pharmaceutical composition is administered in the evening. In one embodiment, the pharmaceutical composition is administered more than 4 hours before bedtime.

Pharmaceutical Compositions

Another aspect of the present disclosure relates to a pharmaceutical composition comprising amantadine. In some embodiments, the pharmaceutical composition is an oral dosage form. The present disclosure is not limited to a particular oral dosage form, and any dosage form capable of delivering amantadine to a patients is suitable for the present invention, so long as the dosage form achieves pharmacokinetic and therapeutic effects described in the present disclosure. Oral dosage forms are recognized by those skilled in the art to include, but are not limited to, liquid formulations, tablets, capsules, and gelcaps. In one embodiment, the pharmaceutical composition is a tablet. In some embodiments, the tablets of the invention can be round, biconvex, and white, green or blue coated tablets.

In some embodiments, the present disclosure provides a pharmaceutical composition comprising about 50 mg to about 400 mg of amantadine or a pharmaceutically acceptable salt thereof. In some embodiments, the pharmaceutical composition is suitable for oral administration.

In some embodiments, the pharmaceutical composition comprises an adsorbent, antioxidant, buffering agent, colorant, flavorant, sweetening agent, antiadherent, binder, diluent, direct compression excipient, disintegrant, glidant, lubricant, opaquant and/or polishing agent.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

As used herein, the term "antioxidant" is intended to mean an agent that inhibits oxidation and thus is used to prevent the deterioration of preparations by the oxidative process. Such compounds include, by way of example and without limitation, ascorbic acid, ascorbyl palmitate, butylated hydroxyanisole, butylated hydroxytoluene, hypophosphorous acid, monothioglycerol, propyl gallate, sodium ascorbate, sodium bisulfate, sodium formaldehyde sulfoxylate and sodium metabisulfite and other materials known to one of ordinary skill in the art.

As used herein, the term "buffering agent" is intended to mean a compound used to resist change in pH upon dilution or addition of acid or alkali. Such compounds include, by way of example and without limitation, potassium metaphosphate, potassium phosphate, monobasic sodium acetate and sodium citrate anhydrous and dihydrate and other materials known to one of ordinary skill in the art.

As used herein, the term "sweetening agent" is intended to mean a compound used to impart sweetness to a preparation. Such compounds include, by way of example and without limitation, aspartame, dextrose, glycerin, mannitol, saccharin sodium, sorbitol and sucrose and other materials known to one of ordinary skill in the art.

As used herein, the term "antiadherent" is intended to mean an agent that prevents the sticking of tablet formulation ingredients to punches and dies in a tableting machine during production. Such compounds include, by way of example and without limitation, magnesium stearate, talc, calcium stearate, glyceryl behenate, PEG, hydrogenated vegetable oil, mineral oil, stearic acid and other materials known to one of ordinary skill in the art.

As used herein, the term "binder" is intended to mean a substance used to cause adhesion of powder particles in tablet granulations. Such compounds include, by way of example and without limitation, Copovidone (Kollidon VA-64) NF, alginic acid, carboxymethylcellulose sodium, poly(vinylpyrrolidone), compressible sugar (e.g., NuTab™), ethylcellulose, gelatin, liquid glucose, methylcellulose, povidone and pregelatinized starch and other materials known to one of ordinary skill in the art.

When needed, a binder may also be included in the present compositions. Exemplary binders include acacia, tragacanth, gelatin, starch, cellulose materials such as methyl cellulose and sodium carboxy methyl cellulose, alginic acids and salts thereof, polyethylene glycol, guar gum, polysaccharide, bentonites, sugars, invert sugars, poloxamers (PLURONIC F68, PLURONIC F127), collagen, albumin, gelatin, cellulosics in nonaqueous solvents, combinations thereof and others known to those of ordinary skill. Other binders include, for example, polypropylene glycol, polyoxyethylene-polypropylene copolymer, polyethylene ester, polyethylene sorbitan ester, polyethylene oxide, combinations thereof and other materials known to one of ordinary skill in the art.

As used herein, the term "diluent" or "filler" is intended to mean an inert substance used as filler to create the desired bulk, flow properties, and compression characteristics in the preparation of tablets and capsules. Such compounds include, by way of example and without limitation, dibasic calcium phosphate, kaolin, lactose, sucrose, mannitol, microcrystalline cellulose (e.g., Microcrystalline Cellulose PH101 NF, and Microcrystalline Cellulose PH200 NF), powdered cellulose, precipitated calcium carbonate, sorbitol, and starch and other materials known to one of ordinary skill in the art.

As used herein, the term "direct compression excipient" is intended to mean a compound used in direct compression tablet formulations. Such compounds include, by way of example and without limitation, dibasic calcium phosphate (e.g., Ditab) and other materials known to one of ordinary skill in the art.

As used herein, the term "glidant" is intended to mean agents used in tablet and capsule formulations to promote the flowability of a granulation. Such compounds include, by way of example and without limitation, colloidal silica, colloidal silicon dioxide NF, cornstarch, talc, calcium silicate, magnesium silicate, colloidal silicon, silicon hydrogel and other materials known to one of ordinary skill in the art. In some embodiments, the pharmaceutical composition further comprises a granulation solvent, e.g., purified water USP.

As used herein, the term "lubricant" is intended to mean substances used in tablet formulations to reduce friction during tablet compression. Such compounds include, by way of example and without limitation, magnesium stearate NF, calcium stearate, magnesium stearate, mineral oil, stearic acid, and zinc stearate and other materials known to one of ordinary skill in the art.

As used herein, the term "opaquant" is intended to mean a compound used to render a capsule or a tablet coating opaque. May be used alone or in combination with a colorant. Such compounds include, by way of example and without limitation, titanium dioxide and other materials known to one of ordinary skill in the art.

As used herein, the term "polishing agent" is intended to mean a compound used to impart an attractive sheen to coated tablets. Such compounds include, by way of example and without limitation, carnauba wax, and white wax and other materials known to one of ordinary skill in the art.

As used herein, the term "disintegrant" is intended to mean a compound used in solid dosage forms to promote the disruption of the solid mass into smaller particles which are more readily dispersed or dissolved. Such disintegrants include, by way of example and without limitation, starches such as corn starch, potato starch, pre-gelatinized and modified starches thereof, sweeteners, clays, such as bentonite, microcrystalline cellulose (e.g., Avicel), carboxymethylcellulose calcium, cellulose polyacrilin potassium (e.g., Amberlite), alginates, sodium starch glycolate, gums such as agar, guar, locust bean, karaya, pectin, tragacanth and other materials known to one of ordinary skill in the art.

As used herein, the term "colorant" is intended to mean a compound used to impart color to solid (e.g., tablets) pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide, red, other F.D. & C. dyes and natural coloring agents such as grape skin extract, beet red powder, beta-carotene, annato, carmine, turmeric, paprika, and other materials known to one of ordinary skill in the art. The amount of coloring agent used varies as desired.

As used herein, the term "flavorant" is intended to mean a compound used to impart a pleasant flavor and often odor to a pharmaceutical preparation. Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, *eucalyptus*, thyme oil, cedar leave oil, oil of nutmeg, oil of sage, oil of bitter almonds and *cassia* oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors which have been found to be particularly useful include commercially available orange, grape, cherry and bubble gum flavors and mixtures thereof. The amount of flavoring may depend on a number of factors, including the organoleptic effect desired. Flavors will be present in any amount as desired by those of ordinary skill in the art. Particularly preferred flavors are the cherry flavors and citrus flavors such as orange.

In some embodiments, the pharmaceutical composition comprises an internal layer, e.g., a core, and an external layer, e.g., a coat. In some embodiments, the amantadine in the core is in an extended release form and the amantadine in the external coat is in an immediate release form. In some embodiments, the total amount of amantadine in the pharmaceutical composition ranges from about 65 mg to about 320 mg. In one embodiment, the total amount of amantadine is about 160 mg. In another embodiment, the total amount of amantadine is about 240 mg. In another embodiment, the total amount of amantadine is about 320 mg. The amount of amantadine in the core generally exceeds the amount present in the external coat. In some embodiments, the amount of amantadine in the core ranges from about 50% to about 85% of the total amount present in the pharmaceutical composition. In some embodiments, the amount of amantadine in the core ranges from about 60% to about 82% of the total amount present in the pharmaceutical composition. In one embodiment, the amount of amantadine in the core is about 62% of the total amount present in the pharmaceutical composition. In another embodiment, the amount of amantadine in the core is about 75% of the total amount present in the pharmaceutical composition. In another embodiment, the amount of amantadine in the core is about 81% of the total amount present in the pharmaceutical composition.

In some embodiments of the present invention, the pharmaceutical composition is an osmotic device. In some embodiments, the osmotic device comprises an active ingredient (drug) and an osmotic salt (osmotic agent) in the core. In these embodiments, amantadine release from the extended release core of a dosage form of the present disclosure invention is controlled by an osmotic pump system. For example, an osmotic pump system may comprise of a drug core contained within a semipermeable polymer membrane that is permeable to water molecules but not to the drug. In some embodiments, the osmotic device further comprises an immediate release layer comprising amantadine or a pharmaceutically acceptable salt thereof. Amantadine release from the osmotic device is driven by the existence of an osmotic gradient between the contents of the drug core and the fluid in the gastrointestinal tract. Since the osmotic gradient remains constant, drug delivery remains essentially constant after the immediate-release layer dissolves. The biologically inert components of the osmotic device remain intact during gastrointestinal transit and are eliminated in the stool as a tablet shell. In some embodiments, the osmotic device comprises a unitary core enclosed with a semipermeable membrane optionally having at least one preformed passageway there through. In some embodiments, the unitary core comprises a mixture of amantadine salt, osmotic salt and one or more pharmaceutical excipients. In some embodiments, the release rate of the active ingredient is reduced and the release profile of the active ingredient is modified by increasing the amount of the osmotic salt in the core. In some embodiments, the osmotic salt is an organic salt. In some embodiments, the osmotic salt is an inorganic salt. In some embodiments, the osmotic salt and the amantadine salt have an ion in common. Having an "ion in common" means that amantadine salt and the osmotic salt each have ions of the same identity. It is not meant that amantadine salt and the osmotic salt actually share the same ion. In some embodiments, the inorganic osmotic salt is a metal halide. In some embodiments, the inorganic osmotic salt is an alkali metal halide or an earth metal halide. In one embodiment, the inorganic osmotic salt is a sodium chloride. By way of example and without limitation, amantadine HCl and NaCl have the chloride ion in common.

In some embodiments, the osmotic device is capable of providing a sigmoidal, pseudo-zero order or zero order release of amantadine or a pharmaceutically acceptable salt thereof. In some embodiments, the sigmoidal, pseudo-zero order, or zero order release is from the core of the device, once the immediate-release layer is dissolved. In one particular embodiment, the release is a zero order release. In another embodiment, the release is pseudo-zero order. In some embodiments, the release of amantadine or a pharmaceutically acceptable salt thereof is essentially constant.

In some embodiments, the unitary core comprises a heterogeneous mixture. In some embodiments, the unitary core comprises a homogeneous mixture. A homogeneous mixture is one wherein all of the ingredients have been thoroughly mixed such that the composition of the formulation is substantially the same throughout different portions of the core. The combined step of mixing and directly compressing the ingredients of the core generally provides a homogeneous mixture. A heterogeneous mixture is one wherein the ingredients of the core are divided into two or more groups that are processed separately to form two or more respective blends, at least one of which contains drug and at least one of which contains the osmotic salt. The blends are then mixed together and compressed to form the unitary core. A heterogeneous mixture can be obtained by wet granulation, dry granulation, pelleting or combinations thereof.

In some embodiments, the osmotic device has a semipermeable membrane. The semipermeable membrane of the osmotic device is formed of a material that is substantially permeable to the passage of fluid from the environment of use to the core and substantially impermeable to the passage of active agent from the core. In some embodiments, the semipermeable membrane comprises a laser drilled orifice for drug delivery. Many common materials that form a semipermeable wall which are known by those of ordinary skill in the art of pharmaceutical sciences are suitable for this purpose.

In some embodiments, the semipermeable membrane comprises at least one film forming polymer. In one embodiment, the semipermeable membrane comprises at least two film-forming polymers. In other embodiments, the semipermeable membrane comprises a plasticizer. Examples of film-forming polymers include, but are not limited to, cellulose esters, cellulose ethers, cellulose esters-ethers, cellulose acylate, or any combinations thereof. In one embodiment, the film-forming polymer is Cellulose Acetate NF (CA-320S), Cellulose Acetate NF (CA-398-10), or a combination thereof. In another embodiment, the film-forming polymer is Opadry Yellow. Examples of plasticizers include, but are not limited to, polyethylene glycol, propylene glycol, polyesters (e.g. poly (lactic acid), and poly(lactide-co-glycolide)), polyesteramides, diesters/triesters of acids, and diesters/triesters of alcohols.

In one embodiment, the semipermeable membrane comprises cellulose acetate (CA) and poly(ethylene glycol) (PEG). In one embodiment, the PEG is PEG 400. The ratio of CA:PEG generally ranges from about 50-99% by weight of CA:about 50-1% by weight of PEG, and about 95% by weight of CA:about 5% by weight of PEG. The ratio can be varied to alter permeability and ultimately the release profile of the osmotic device. In some embodiments, the cellulose acylate is cellulose acetate, cellulose diacetate, cellulose triacetate or any combinations thereof. Many suitable polymers, including those disclosed in Argentine Patent No. 199,301, U.S. Pat. No. 6,004,582 and other references cited herein, are hereby incorporated by reference.

In some embodiments, the semipermeable membrane comprises at least two different grades of cellulose acetate. Grade 1 cellulose acetate has a higher viscosity, a higher percentage of hydroxyl groups, and a lower percentage of acetyl groups than does grade 2, meaning that grade 2 has a lower viscosity, lower percentage of hydroxyl groups and higher percentage of acetyl groups than does grade 1. In some embodiments, the two different grades of cellulose acetate are Cellulose Acetate NF (CA-320S) and Cellulose Acetate NF (CA-398-10).

In some embodiments, the semi-permeable membrane further comprises a coating solvent. Examples of coating solvents include, but are not limited to, ethylcellulose, ethanol, acetone, dichloromethane, isopropanol, and other materials known to one of ordinary skill in the art. In one embodiment, the coating solvent is acetone. In another embodiment, the coating solvent is water. In yet another embodiment, the semi-permeable membrane comprises acetone and purified water USP.

In some embodiments, the osmotic device comprises a water soluble and/or erodible coating, which covers and surrounds the semipermeable membrane and plug any pre-formed passageway in the membrane if the passageway had been formed prior to addition of the coating. The water soluble and/or erodible coating is described in detail above.

In some embodiments, the osmotic device comprises a color separation coating over the semi-permeable membrane. The color separating coating can comprise a film forming polymer, a coating solvent, or a combination thereof.

In some embodiments, the osmotic device further comprises an IR layer comprising amantadine or a pharmaceutically acceptable salt thereof. In some embodiment, the IR layer further comprises a film forming polymer. In another embodiment, the IR layer comprises a coating solvent. Examples of film-forming polymers and coatings solvents are listed above and can also include other materials known to one of ordinary skill in the art.

In some embodiments, the osmotic device further comprises an aesthetic coating comprising a film forming polymer and a coating solvent. Examples of film-forming polymers and coatings solvents are listed above and can also include other materials known to one of ordinary skill in the art. In one embodiment, the film forming polymer is Opadry White (Y-30-18037), Opadry Green (15B110000), Opadry Blue (15B105001), or any combinations thereof. In one embodiment, the coating solvent is purified water.

In some embodiment, the osmotic device further comprises a printing. In one embodiment, the printing is ink (e.g., Opacode WB NS-78-17821 Black).

Method of Preparation of the Pharmaceutical Compositions

The pharmaceutical compositions can be prepared according to the methods disclosed herein or those well known in the art.

In the embodiment related to an osmotic device, the active agent and excipients that comprise the core are mixed in solid, semisolid or gelatinous form, then moistened and sieved through a specified screen to obtain a granulate. The granulate is then dried in a dryer and compressed, for example, by punching to form uncoated cores. The compressed and uncoated cores are then covered with a solution of suitable materials that comprise the wall. Subsequently, the wall surrounding each core is perforated with, for example, laser equipment to form the preformed passageway in the manner previously described. In some embodiments, a drug-containing external coat is applied to cover the wall as a sprayed coating or a compression coating. In some embodiments, the osmotic device is coated with a finish coat as is commonly done in the art to provide the desired shine, color, taste or other aesthetic characteristics. Materials suitable for preparing the finish coat are well known in the art and found in the disclosures of many of the references cited and incorporated by reference herein.

Combination Therapy

Amantadine may be administered as a combination with a second agent for treatment of Parkinson's Disease. Amantadine may also be administered as a combination with a second agent for treatment of drug-induced extrapyramidal reactions. Additionally, amantadine may be administered as a combination with a second agent for treatment of levodopa-induced dyskinesia. In some embodiments, the second agent comprises one or more compounds selected from the group consisting of levodopa and/or another drug selected from the group consisting of an aromatic-L-amino-acid decarboxylase inhibitor such as carbidopa or benserezide; dopamine agonists such as apomorphine, bromocriptine, cabergoline, lisuride, pergolide, pramipexole, ropinirole, and rotigotine; COMT (catechol O-methyltransferase) inhibitors such as entacapone, tolcapone and BIA 9-1067 (opicapone); MAO-B (monoamine oxidase B) inhibitors such as selegiline, rasagiline and safinamide; anticholinergics such as trihexyphenidyl, benztropine, orphenadrine, procyclidine, ethopropazine, and glycopyrrolate; benzodiazepines such as alprazolam, lorazepam, diazepam, clonazepam; SSRIs (selective serotonin reuptake inhibitors) such as fluoxetine, sertraline, paroxetine and fluvoxamine; tricyclic and tetracyclic antidepressants such as mirtazapine, doxepin, imipramine, desipramine, trazodone, and nortriptyline; nonsteroidal anti-inflammatory agents such as minocycline and COX-2 (cyclooxygenase-2) inhibitors; non-narcotic analgesic such as acetaminophen, aspirin, diclofenac, diflusinal, etodolac, fenbufen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin, tramadol and zomepiracadenosine; narcotic analgesics such as codeine, dihydrocodeine, hydrocodone, hydromorphone, levorphanol, morphine, oxycodone and tapentadol; ADORA2A (adenosine A2A receptor) antagonists such as preladenant, tozadenant, DT-1133 and DT1687; anti-epileptic agents selected from the group consisting of AMPA antagonists, Benzodiazepines, Barbiturates, Valproates, GABA analogs, Iminostilbenes, Hydantoins, NMDA antagonists, Sodium channel blockers, Carboxylic acids, oxazolidinediones, succinimides, pyrrolidines, sulphonamides, aminobutyric acids, sulfamate-substituted monosaccharides, carboxamides, aromatic allylic alcohols, ureas, phenyltriazines, carbamates, pyrrolidines, losigamone, retigabine, rufinamide, acetazolamide, clomthiazole edisilate, zonisamide, felbamate, topiramate, tiagabine, levetiracetam, briveracetam, SPD 421 (DP-VPA), T-2000, XP-13512, GSK-362115, GSK-406725, ICA-69673, CBD cannabis derivative, isovaleramide (NPS-1776), carisbamate, safinamide, seletracetam, soretolide, stiripentol, and valrocemide; lacosamide, gabapentin, indomethacin, steroids, fluorocortisone, desmopressin, oxybutynin, tolterodine, hyoscyamine, midodrine, phenylephrine, phenylpropanolamine, baclofen, dantrolene, domperidone, mosapride, tegaserod, donepezil, memantine, riluzole, rivastigmine, coenzyme Q10, vitamin E, vitamin C, creatine, *ginkgo biloba*, nicotinamide, carnitine, piribedil, buspirone, clozapine, quetiapine, olanzapine, risperidone, aripiprazole, methylphenidate, modafinil, dipraglurant, fipamezole, AFQ056, AQW-051, Neu-120, olesoxime, 17-B-hydroxyepiandrosterone, (+)-phenserine, clavulanic acid, HE-3286, YM-50018, MCD-386, AV-101, SUVN-502, EVP-0334, V-81444, SCH-900800, ADX-88178, NNZ-2591, AEOL-11207, Proximagen, IC-200214, SIG-1012, ADL-5510, TrkB PAM, and G-79.

In some embodiments, the second agent is present in an amount known to be therapeutically (clinically) effective for the treatment of a target condition, disease or disorder, such as those described herein, when a unit dose of the pharmaceutical composition is administered to a subject in need thereof. Guidance as to the therapeutically effective amount of each previously marketed second agent can be obtained from the Food and Drug Administration (USA, www.fda.gov), European Medicines Agency (Europe, ema.europa.eu), National Institute of Health Sciences (Japan, www.nihs.go.jp), and National Administration of Drugs, Food, and Medical Technology (Administracion Nacional de Medicamentos, Alimentos y Tecnologia Medica, Argentina, www.anmat.gov.ar), the disclosures of which are incorporated herein by reference in their entirety. For example, the package insert for any approved drug includes dosage and administration information, which can be used to determine the proper amount of each drug to be included in a pharmaceutical composition of the invention. The amounts for a particular drug combination in accordance with this invention can be determined employing routine experimental testing. If the drugs are present in such a weight ratio that a super-additive or synergistic therapeutic effect is observed upon administration to the patients, the overall administered dose may be lowered, so that fewer undesired side-effects will occur.

In some embodiments, the pharmaceutical composition comprises a combination of amantadine and one or more other drugs, and may contain an excess of amantadine, an excess of the one or more other drugs, or equivalent amounts of amantadine and the one or more other drugs. The weight ratio of amantadine to the one or more other drugs can range from about 100:1 to 1:100. In one embodiment, the one or more other drugs are administered to the subject, sequentially or concomitantly, in another dosage form such that the subject receives a dose of the one or more other drugs in the pharmaceutical composition and a dose of the one or more other drugs in another dosage form. The dosing regimen for the one or more other drugs can thus be the same as or different than the dosing regimen for amantadine.

In some embodiments, the pharmaceutical composition comprises an external coat comprising a second active agent for immediate release of the drug. In some embodiments, the osmotic device comprises a coat external to the semipermeable memebrane. The external coat can be a rapid release coat. In some embodiments, the second active ingredient in the external rapid release coat is selected from the group consisting of amantadine, cabergoline, pergolide, selegiline, rasagiline, trihexyphenidyl, benztropine, donepezil, fluoxetine, sertraline, paroxetine, fluvoxamine, mirtazapine, doxepin, desipramine, clozapine, olanzapine, risperidone, aripiprazole, fludrocortisone, safinamide, and smilagenin. In some embodiments, the osmotic device comprises a non-absorbable shell.

In vitro Assays

The pharmaceutical compositions prepared according to certain embodiments of the present invention preferably exhibit the following dissolution profile when tested in a USP Type II dissolution apparatus (paddles), using water or in 0.1N HCl as a dissolution media, with a fixed agitation rate of 50 revolutions per minute, maintained at a temperature of about 37±0.5° C. In some embodiments, the pharmaceutical composition has an in vitro dissolution profile ranging between about 0.1% to about 50% in about 0.5 hour, about 20% to about 80% in about 2.5 hours, about 40% to about 90% in about 4 hours, and no less than about 85% in about 8 hours using water as a dissolution media. In one embodiment, the pharmaceutical composition has an in vitro dissolution profile ranging between about 28% to about 48% in about 0.5 hour, about 39% to about 63% in about 2.5 hours, about 61% to about 85% in about 4 hours, and no less than about 85% in about 8 hours using water as a dissolution media. In another embodiment, the pharmaceutical composition has an in vitro dissolution profile ranging between about 15% to about 35% in about 0.5 hour, about 29% to about 53% in about 2.5 hours, about 53% to about 77% in about 4 hours, and no less than about 85% in about 8 hours using water as a dissolution media. In another embodiment, the pharmaceutical composition has an in vitro dissolution profile ranging between about 9% to about 29% in about 0.5 hour, about 37% to about 62% in about 2.5 hours, about 59% to about 83% in about 4 hours, and no less than about 85% in about 8 hours using water as a dissolution media. In one embodiment, the pharmaceutical composition has an in vitro dissolution profile ranging between about 0.1% to about 10% in about 1 hour, about 20% to about 60% in about 2.5 hours, about 40% to about 80% in about 4 hours, about 70% to about 95% in about 6 hours, and no less than about 85% in about 8 hours. In another embodiment, the pharmaceutical composition has an in vitro dissolution profile in water ranging between about 0.1% to about 10% in about 1 hour, about 5% to about 50% in about 2.5 hours, about 40% to about 80% in about 4 hours, about 70% to about 95% in about 6 hours, and no less than about 85% in about 8 hours. In another embodiment, the pharmaceutical composition has an in vitro dissolution profile in water ranging between about 0.1% to about 10% in about 1 hour, about 5% to about 60% in about 2.5 hours, about 40% to about 90% in about 4 hours, about 80% to about 97% in about 6 hours, and no less than about 95% in about 8 hours. In some embodiments, an extended release pharmaceutical composition comprising amantadine has an in vitro dissolution profile in a solution with a neutral pH (e.g., water) that is substantially the same as its dissolution profile in an acidic dissolution medium.

Pharmacokinetics

Amantadine in an extended release form is released into a subject sample at a slower rate than observed for an immediate release formulation of the same quantity of amantadine, such that the rate of change in the biological sample is measured as the dC/dT over a defined period.

In some embodiments, the dC/dT of amantadine is less than about 80%, about 70%, about 60%, about 50%, about 40%, about 30%, or about 20% of the dC/dT provided by the same quantity of amantadine in an immediate release form, when the dC/dT is measured between 0 and 4 hours after administration. In some embodiments, the dC/dT of amantadine is greater than about 30%, about 40% and about 50% of the dC/dT provided by the same quantity of amantadine in an immediate release form, when the dC/dT is measured between 0 and 4 hours after administration. In one embodiment, the dC/dT of amantadine is greater than about 50% of the dC/dT provided by the same quantity of amantadine in an immediate release form, when the dC/dT is measured between 0 and 4 hours after administration.

In some embodiments, the dC/dT of amantadine is from about 40% to about 70%, from about 40% to about 60%, from about 40% to about 50%, from about 50% to about 60%, from about 50% to about 70%, from about 60% to about 70% of the dC/dT provided by the same quantity of amantadine in an immediate release form, when the dC/dT is measured between 0 and $T_{max}$ for the IR formulation after administration. In one embodiment, the dC/dT of amantadine is about 45% of the dC/dT provided by the same quantity of amantadine in an immediate release form, when the dC/dT is measured between 0 and $T_{max}$ for the IR formulation after administration. In another embodiment, the dC/dT of amantadine is about 55% of the dC/dT provided by the same quantity of amantadine in an immediate release form, when the dC/dT is measured between 0 and $T_{max}$ for the IR formulation after administration. In another embodiment, the dC/dT of amantadine is about 70% of the dC/dT provided by the same quantity of amantadine in an immediate release form, when the dC/dT is measured between 0 and $T_{max}$ for the IR formulation after administration.

In some embodiments, amantadine is formulated to release at a rate that is significantly reduced over an immediate release dosage form, with an associated delay in the mean $T_{max}$. In some embodiments, the pharmaceutical composition is formulated to provide a shift in $T_{max}$ by about 16 hours, about 14 hours, about 12 hours, about 10 hours, about 9 hours, about 8 hours, about 7 hours, about 6 hours, about 5 hours, about 4 hours, about 3 hours, about 2 hours, or about 1 hour.

In some embodiments, the $T_{max}$ of the pharmaceutical composition is between about 5 and about 12 hours, between about 5 and about 10 hours, between about 5 and about 8 hours, between about 5 and about 6 hours, between about 6 and about 12 hours, between about 6 and about 10 hours, between about 6 and about 8 hours, between about 7 and about 12 hours, between about 7 and about 10 hours, between about 7 and about 8 hours, between about 8 and about 12 hours, between about 8 and about 10 hours, between about 9 and about 12 hours, between about 9 and about 10 hours, or between about 10 and about 12 hours. In one embodiment, the median $T_{max}$ of the pharmaceutical composition is about 7.5 hours.

In some embodiments, the pharmaceutical composition comprising an extended release amantadine reduces the dC/dT of the drug, and not only increases mean $T_{max}$, but also reduces mean $C_{max}$ (the drug concentration at $T_{max}$) and reduces the $C_{max}/C_{mean}$ ratio providing a more constant amount of drug to the subject being treated over a given period of time, enabling increased dosages for appropriate indications. In some embodiments, the mean $C_{max}$ of the pharmaceutical composition after a single-dose administration is between about 200 and about 1000 ng/ml, between about 200 and about 900 ng/ml, between about 200 and about 800 ng/ml, between about 200 and about 700 ng/ml, between about 200 and about 600 ng/ml, between about 200 and about 500 ng/ml, between about 200 and about 400 ng/ml, between about 200 and about 300 ng/ml, between about 300 and about 1000 ng/ml, between about 300 and about 900 ng/ml, between about 300 and about 800 ng/ml, between about 300 and about 700 ng/ml, between about 300 and about 600 ng/ml, between about 300 and about 500 ng/ml, between about 300 and about 400 ng/ml, between about 400 and about 1000 ng/ml, between about 400 and about 900 ng/ml, between about 400 and about 800 ng/ml, between about 400 and about 700 ng/ml, between about 400 and about 600 ng/ml, between about 400 and about 500 ng/ml, between about 500 and about 1000 ng/ml, between about 500 and about 900 ng/ml, between about 500 and about 800 ng/ml, between about 500 and about 700 ng/ml, between about 500 and about 600 ng/ml.

In some embodiments, the mean $C_{max}$ of the pharmaceutical composition after a single-dose administration is between about 540 and about 895 ng/ml. In one embodiment, the pharmaceutical composition comprises about 320 mg amantadine. In some embodiments, the mean $C_{max}$ of the pharmaceutical composition after a single-dose administration is between about 370 and about 550 ng/ml. In one embodiment, the pharmaceutical composition comprises about 240 mg amantadine. In some embodiments, the mean $C_{max}$ of the pharmaceutical composition after a single-dose administration is between about 265 and about 390 ng/ml. In one embodiment, the pharmaceutical composition comprises about 160 mg amantadine. In some embodiments, after a single oral administration of the 129 mg amantadine free base equivalent, the mean (CV %) $C_{max}$ is 328 ng/ml (18%). $C_{max}$ with other dose levels of the pharmaceutical composition increases proportionally.

Another PK parameter of interest is the resulting area under the plasma concentration-time curve ($AUC_{0-\infty}$), calculated to the last measured concentration ($AUC_{0-T}$) and extrapolated to infinity ($AUC_{t-\infty}$), for extent of absorption of amantadine. In some embodiments, the mean $AUC_{0-\infty}$ of the pharmaceutical composition after a single-dose administration is between about 6,000 and about 24,000 ng·h/mL, between about 6,000 and about 20,000 ng·h/mL, between about 6,000 and about 16,000 ng·h/mL, between about 6,000 and about 12,000 ng·h/mL, between about 6,000 and about 10,000 ng·h/mL, between about 6,000 and about 8,000 ng·h/mL, between about 8,000 and about 24,000 ng·h/mL, between about 8,000 and about 20,000 ng·h/mL, between about 8,000 and about 16,000 ng·h/mL, between about 8,000 and about 12,000 ng·h/mL, between about 8,000 and about 10,000 ng·h/mL, between about 10,000 and about 24,000 ng·h/mL, between about 10,000 and about 20,000 ng·h/mL, between about 10,000 and about 16,000 ng·h/mL, between about 10,000 and about 12,000 ng·h/mL, between about 12,000 and about 24,000 ng·h/mL, between about 12,000 and about 20,000 ng·h/mL, between about 12,000 and about 16,000 ng·h/mL, between about 16,000 and about 24,000 ng·h/mL, between about 16,000 and about 20,000 ng·h/mL, or between about 20,000 and about 24,000 ng·h/mL.

In some embodiments, the mean $AUC_{0-\infty}$ of the composition after a single-dose administration is between about 12,000 and about 26,000 ng·h/mL. In some embodiments, the mean $AUC_{0-\infty}$ of the composition after a single-dose administration is between about 12,500 and about 23,500 ng·h/mL. In one embodiment, the pharmaceutical composition comprises about 320 mg amantadine HCl. In some embodiments, the mean $AUC_{0-\infty}$ of the composition after a single-dose administration is between about 8,000 and about 20,000 ng·h/mL. In some embodiments, the mean $AUC_{0-\infty}$ of the composition after a single-dose administration is between about 10,400 and about 15,900 ng·h/mL. In one embodiment, the pharmaceutical composition comprises about 240 mg amantadine HCl. In some embodiments, the mean $AUC_{0-\infty}$ of the composition after a single-dose administration is between about 6,000 and about 26,000 ng·h/mL. In some embodiments, the mean $AUC_{0-\infty}$ of the composition after a single-dose administration is between about 6,900 and about 10,300 ng·h/mL. the mean $AUC_{0-\infty}$ of the composition after a single-dose administration is between about 6,000 and about 12,000 ng·h/mL. In one embodiment, the pharmaceutical composition comprises about 160 mg amantadine HCl. In some embodiments, after a single oral administration of the 129 mg amantadine free base equivalent, the mean $AUC_{0-\infty}$ is about 8580 ng h/mL with other dose levels of the pharmaceutical composition increasing proportionally.

In some embodiments, the relative bioavailability of amantadine or a pharmaceutically acceptable salt thereof is approximately the same under fed and fasting conditions.

Efficacy

In the present invention, treatment of patients with an extended release amantadine dosage form of the present invention improves symptoms of PD, extrapyramidal reactions, and/or levodopa-induced dyskinesia.

In some embodiments, treatment of patients with an extended release amantadine dosage form of the present invention improves dyskinesia in a patient with levodopa-induced dyskinesia (LID) as determined by a reduction in a total Unified Dyskinesia Rating Scale (UdysRS) score after twelve weeks. In some embodiments, the treatment increases the number of awake ON hours without dyskinesia in the patient.

In some embodiments, the reduction in UdysRS score is between about −2 and about −7, between about −2 and about −6, between about −2 and about −5, between about −2 and about −4, between about −2 and about −3, between about −3 and about −7, between about −3 and about −6, between about −3 and about −5, between about −3 and about −4, between about −4 and about −7, between about −4 and about −6, between about −4 and about −5, between about −5 and about −7, between about −5 and about −6, or between about −6 and about −7, after twelve weeks, compared to placebo. In one embodiment, the reduction in UdysRS score is about −5 after twelve weeks, compared to placebo.

In some embodiments, the reduction in UdysRS score is between about −9 and about −17, between about −9 and about −16, between about −9 and about −15, between about −9 and about −14, between about −9 and about −13, about −9 and about −12, about −9 and about −11, about −9 and about −10, between about −10 and about −17, between about −10 and about −16, between about −10 and about −15, between about −10 and about −14, between about −10 and about −13, about −10 and about −12, about −10 and about −11, between about −11 and about −17, between about −11 and about −16, between about −11 and about −15, between about −11 and about −14, between about −11 and about −13, about −11 and about −12, between about −12 and about −17, between about −12 and about −16, between about −12 and about −15, between about −12 and about −14, between about −12 and about −13, between about −13 and about −17, between about −13 and about −16, between about −13 and about −15, between about −13 and about −14, between about −14 and about −17, between about −14 and about −16, between about −14 and about −15, between about −15 and about −17, between about −15 and about −16, or between about −16 and about −17, after twelve weeks. In one embodiment, the reduction in UdysRS score is about −13 after twelve weeks.

In some embodiments, the method increases the number of awake ON hours without dyskinesia in the patient by about 1 to about 4 hours, by about 1 to about 3 hours, by about 1 to about 2 hours, by about 2 to about 4 hours, by about 2 to about 3 hours, or by about 3 to about 4 hours after twelve weeks. In one embodiment, the method increases the number of awake ON hours without dyskinesia in the patient by about 4 hours after twelve weeks.

In some embodiments, the number of awake ON hours without dyskinesia in the patient is between about 9 and about 14 hours, between about 9 and about 13 hours, between about 9 and about 12 hours, between about 9 and about 11 hours, between about 9 and about 10 hours, between about 10 and about 14 hours, between about 10 and about 13 hours, between about 10 and about 12 hours, between about 10 and about 11 hours, between about 11 and about 14 hours, between about 11 and about 13 hours, between about 11 and about 12 hours, between about 12 and about 14 hours, between about 12 and about 13 hours, or between about 13 and about 14 hours.

In some embodiments, MDS-UPDRS (Movement Disorder Society-Unified Parkinson's Disease Rating Scale) Part II and III is used to assess any potential worsening of PD symptoms. In some embodiments, the method does not worsen Parkinson's disease symptoms in the subjects (patients).

Indications

The pharmaceutical compositions of the present invention are suitable for the treatment of diseases, disorders and/or symptoms that are therapeutically or clinically responsive to amantadine therapy. In some embodiments, diseases, disorders and/or symptoms that are responsive to amantadine therapy include, but are not limited to, Parkinson's disease, parkinsonism, drug-induced extrapyramidal reactions (including, for example, akathisia, dystonia or dyskinesia), levodopa-induced dyskinesia, viral infection, and signs and symptoms of infection caused by various strains of influenza A virus, especially for high-risk patients such as those in critical public-service positions, immunosuppressed patients, nursing home residents, contacts of high-risk patients, and those with severe influenza A viral infection.

The pharmaceutical compositions of the present invention can be administered for the treatment of elderly patients believed to develop Parkinsonism in association with or as a result of cerebral arteriosclerosis or another neurodegenerative disease, dementia in Parkinson's disease, fatigue associated with multiple, reducing relapses in multiple sclerosis, improving symptoms of attention deficit hyperactivity disorder (ADHD), SSRI-induced sexual dysfunction, management of addictions and substance dependence, resistant unipolar depression, bipolar disorders, Alzheimer's Disease, senile dementia, Huntington's disease, neuropathic pain, postoperative pain, refractory absence seizures, brain injury, and traumatic brain injury.

In some embodiments, the pharmaceutical compositions of the present invention are suitable for the treatment of a disease or a disorder selected from the group consisting of Parkinson's disease, drug-induced extrapyramidal reactions, levodopa-induced dyskinesia, and any combinations thereof.

In some embodiments, the pharmaceutical compositions of the present invention are suitable for the treatment of Parkinson's disease.

In another embodiment, the pharmaceutical compositions of the present invention are suitable for the treatment of drug-induced extrapyramidal reactions.

In another embodiment, the pharmaceutical compositions of the present invention are suitable for the treatment of levodopa-induced dyskinesia.

In some embodiments, the drug-induced extrapyramidal reactions include, but are not limited to, dystonia (continuous spasms and muscle contractions), akathisia (motor restlessness), parkinsonism (characteristic symptoms such as rigidity), bradykinesia (slowness of movement), tremor, tardive dyskinesia (irregular, jerky movements), and other side effects caused by antipsychotics.

In some embodiments, the drug-induced extrapyramidal reactions are caused by, but not limited to, antipsychotic drugs, such as haloperidol, fluphenazine, thilthixene, trifluoroperazine, acetophenazine, prochlorperazine, perphenazine, loxapine, chlorpromazine, triflupromazine, molindone, mesoridazine, chlorprothixene, thioridazine, clozapine; other anti-dopaminergic drugs, such as antiemetic metoclopramide, trimethobenzamide (e.g., Tigan®) and metoclopramide (e.g., Reglan®), other substituted benzamides; antidepressants, such as selective serotonin reuptake inhibitors (SSRI), serotonin-norepinephrine reuptake inhibitors (SNRT), and norepinephrine-dopamine reuptake inhibitors (NDRI), desipramine (e.g., Norpramin®), protriptyline (e.g., Vivactil®). duloxetine, sertraline, escitalopram, fluoxetine, and bupropion; concomitantly using neuroleptics and lithium; anticonvulsant agents such as phenytoin (e.g., Dilantin®) and carbamazepine (e.g., Tegretol®); and oral contraceptives.

In a specific embodiment, the patient has Parkinson's disease, which, as used herein, also encompasses a diagnosis of parkinsonism. In one embodiment, the patient has early stage Parkinson's disease, and the pharmaceutical composition of the present invention is administered as a monotherapy or in combination with a MAO-B inhibitor without concomitant use of levodopa. In another embodiment, the patient has late stage Parkinson's disease and the patient takes levodopa in addition to the pharmaceutical composition of the present invention. In another embodiment, the patient has multiple sclerosis and the pharmaceutical composition of the present invention is used for the treatment of walking impairment (that is, improve walking mobility, distance and speed), and to reduce or to relieve fatigue.

The pharmaceutical compositions of the present invention are also suitable for the treatment of diseases, disorders and/or symptoms that are responsive to a combination of amantadine and a second drug. In some embodiments, the invention includes an osmotic device for the combined administration of amantadine in a controlled release manner and an antidepressant in an immediate or rapid release manner, e.g., the combination of amantadine and citalopram, fluoxetine, paroxetine, sertraline, fluvoxamine or escitalopram. In some embodiments, the invention also includes an osmotic device for the combined administration of amantadine in a controlled release manner and an anxiolytic agent in an immediate or rapid release manner, e.g., amantadine and buspirone or trazodone, for the amelioration of undesired tremors, akinesia, dyskinesia, or bradykinesia associated with one or more different disorders or diseases. In some embodiments, the invention also includes an osmotic device for the combined administration of amantadine and a second anti-Parkinsonian drug in a controlled release manner from the core, e.g., amantadine and ropinirole, or selegiline, or levodopa-carbidopa. The term "anti-Parkinsonian drug" means a drug known in the art for use in treating Parkinson's disease.

In some embodiments, amantadine is combined with an active agent selected from narcotic analgesics, gabapentin and/or lacosamide to control a patient's pain. Examples of medical conditions and/or types of pain that can be treated with such an osmotic device include acute inflammatory pain; acute pain; alcoholism-associated or alcoholism-induced neuropathic pain; allodynia (occurring independently or as a symptom of another condition); arthritic conditions; back pain; cancer-related neuropathic pain, e.g., painful compression by tumor growth of adjacent nerves, the brain or the spinal cord; central neuropathic pain; chronic headache; chronic inflammatory pain; chronic pain; chronic pain due to peripheral nerve injury; diabetes-associated or diabetes-induced neuropathic pain; diabetic pain; diabetic distal sensory neuropathy; diabetic distal sensory polyneuropathy; fibromyalgia; headache; hyperalgesia (occurring independently or as a symptom of another condition); hyperesthesia; hyperpathia; migraine, including classical migraine and common migraine; myalgia; myofascial pain syndrome; neuralgia; neuroma; non-inflammatory musculoskeletal pain; non-inflammatory osteoarthritic pain; non-neuropathic inflammatory pain; neuropathic pain; pain associated with or induced by chemotherapy or radiation therapy; pain associated with or induced by traumatic nerve injury or compression or by traumatic injury to the brain or spinal cord; painful diabetic neuropathy; peripheral neuropathic pain; persistent clinical pain; phantom pain; rheumatoid arthritis pain; secondary inflammatory osteoarthritic pain; trigeminal neuralgia; and vascular headache.

EXAMPLES

Example 1

Amantadine Tablet Formulation

Amantadine HCl Extended Release (ER) Tablets, 160, 240 and 320 mg (each tablet contains 129 mg, 193 mg, or 258 mg amantadine fee base equivalent, respectively) were manufactured as described herein. The tablets contain an extended release core and an immediate release layer.

Amantadine release from the extended release core is controlled by an osmotic pump system. The osmotic pump system consists of a drug core contained within a semipermeable polymer membrane that is permeable to water molecules but not to the drug with a laser drilled orifice for drug delivery. Amantadine release is driven by the existence of an osmotic gradient between the contents of the drug core and the fluid in the gastrointestinal tract. Since the osmotic gradient remains constant, drug delivery remains essentially constant after the immediate-release layer dissolves. The biologically inert components of the tablet remain intact during gastrointestinal transit and are eliminated in the stool as a tablet shell.

Amantadine HCl core was coated with a semi-permeable membrane (Coating A) and laser drilled to provide an orifice. The extended release core was coated with the following 3 additional coatings: a color separation coating (Coating B), an amantadine HCl immediate release layer (Coating C), and a non-performance color coating (Coating D) with black imprinting.

The formulation was designed to provide for once-a-day dosing; the immediate release component was included to eliminate a lag time. The core composition is the same for all three tablet strengths, the weight of the core increases dose proportionally with increasing dose. The unit-dose composition for Amantadine HCl ER Tablets, 160, 240 and 320 mg is provided in Table 1.

TABLE 1

Summary of Unit-Dose Amantadine HCl ER Tablet Composition by Tablet Strength

| Ingredient | 160 mg | | 240 mg | | 320 mg | |
|---|---|---|---|---|---|---|
| | mg/tablet | % w/w | mg/tablet | % w/w | mg/tablet | % w/w |
| Tablet Core | | | | | | |
| Amantadine Hydrochloride USP (Active) | 100.00 | 30-50 | 180.00 | 35-55 | 260.00 | 40-60 |
| Osmotic Agent | 4-9 | 2-3 | 9-14 | 2-4 | 13-20 | 2-5 |
| Binder | 4-10 | 2-4 | 10-16 | 2-5 | 15-24 | 2-5 |
| Filler 1 | 23-29 | 8-12 | 40-54 | 10-14 | 54-72 | 10-16 |
| Filler 2 | 6-10 | 2-4 | 11-18 | 2-5 | 16-26 | 3-5 |
| Glidant | 0.5-0.8 | 0.2-0.3 | 0.5-2 | 0.2-0.4 | 1-2 | 0.2-0.5 |
| Lubricant | 1-1.5 | 0.4-0.6 | 1-3 | 0.2-1 | 2-4 | 0.4-0.8 |
| Granulation Solvent | 25-35 | | 44-64 | | 63-83 | |
| Final Core weight (mg) | 120-180 | | 210-330 | | 310-470 | |
| Osmotic Coating (Coating A) | | | | | | |
| Film forming polymer 1 | 6-10 | 2-4 | 8-15 | 2-4 | 8-15 | 1-3 |
| Film forming polymer 2 | 6-10 | 2-4 | 8-15 | 2-4 | 8-15 | 1-3 |
| Plasticizer | 0.5-1 | 0.2-0.5 | 0.8-2 | 0.2-0.6 | 0.8-2 | 0.1-0.5 |
| Coating Solvent 1 | 200-300 | | 300-400 | | 300-400 | |
| Coating Solvent 2 | 30-50 | | 50-70 | | 50-70 | |
| Osmotic Coating weight (mg) | 12-21 | | 20-30 | | 20-30 | |
| Coated Tablet weight (mg) | 130-200 | | 230-360 | | 330-500 | |
| Color Separation Coating (Coating B) | | | | | | |
| Film forming polymer | 4-6 | 1.5-2.5 | 7-11 | 1.8-3 | 9-15 | 1.8-3 |
| Coating Solvent | 38-54 | | 64-98 | | 85-130 | |
| Coated Tablet weight (mg) | 135-205 | | 235-365 | | 342-512 | |
| IR Layer (Coating C) | | | | | | |
| Active | 60.00 | 18-30 | 60.00 | 12-18 | 60.00 | 8-14 |
| Film forming polymer | 11-18 | 4-8 | 11-18 | 3-5 | 11-18 | 2-3.5 |
| Coating Solvent | 300-500 | | 300-500 | | 300-500 | |
| IR Layer weight (mg) | 60-90 | | 60-90 | | 60-90 | |

TABLE 1-continued

Summary of Unit-Dose Amantadine HCl ER Tablet Composition by Tablet Strength

| Ingredient | 160 mg | | 240 mg | | 320 mg | |
|---|---|---|---|---|---|---|
| | mg/tablet | % w/w | mg/tablet | % w/w | mg/tablet | % w/w |
| IR Coated Tablet weight (mg) | 200-300 | | 300-450 | | 400-600 | |
| *Aesthetic Coating (Coating D)* | | | | | | |
| Film forming polymer 1 | 6-9 | 2.5-3.5 | — | | | |
| Film forming polymer 2 | — | | 9-14 | 2.5-3.5 | | |
| Film forming polymer 3 | — | | | | 10-20 | 2-4 |
| Coating Solvent | 50-80 | | 80-130 | | 100-170 | |
| Coated Tablet weight (mg) | 200-300 | | 300-500 | | 400-600 | |
| *Printing (Optional)* | | | | | | |
| Ink | | | | | | |
| Total Tablet weight (mg) | 200-300 | 100.00% | 300-500 | 100.00% | 400-600 | 100.00% |

[1] Removed during manufacturing process

Example 2

Biopharmaceutic Studies and Associated Analytical Methods 2.1 Background and Overview.

Three clinical studies were conducted to compare relative bioavailability of Amantadine HCl ER Tablets, 160 mg, 240 mg and 320 mg, and an immediate release amantadine oral syrup formulation. Amantadine HCl ER Tablets were manufactured as described in Example 1. Amantadine HCl syrup, 50 mg/5 mL (amantadine HCl oral solution, USP), ANDA 075060, was the approved immediate-release product (Reference Listed Drug, RLD) and used as reference product in the comparative bioavailability studies.

The three bioavailability studies were carried out in healthy volunteers:

1. Study I compared the steady-state bioavailability of amantadine from one Amantadine HCl ER 320 mg Tablet administered orally once daily to 160 mg amantadine HCl syrup, 50 mg/5 mL administered orally twice daily for 7 days;
2. Study II compared the single-dose bioavailability and pharmacokinetics of Amantadine HCl ER Tablets, at 160 mg, 240 mg, and 320 mg to a single oral 160 mg dose of amantadine HCl syrup, 50 mg/5 mL; and 3. Study III evaluated the effect of a high-fat meal on amantadine bioavailability for Amantadine HCl ER Tablets, at 320 mg.

2.2 Summary of Results of Individual Studies 2.2.1 Study III (Relative Bioavailability of Amantadine HCl ER Tablet, 320 mg Under Fasting and Fed Conditions)

Study III was an open-label, balanced, randomized, two-period, two-sequence, single dose, bioavailability study under fasting and fed conditions of Amantadine HCl 320 mg ER Tablets in normal, healthy, adult male and female volunteers.

In each study period, 22 blood samples (4 mL each), including one pre-dose blood sample were collected from each subject. There were 7 days between dosing periods. The following 2 treatments were administered: Amantadine HCl 320 mg ER tablets given under fasting conditions (Test-T1, Fasted), and Amantadine HCl 320 mg ER tablets given under fed conditions (Test-T2, Fed).

Dosing Under Fasting Conditions

After an overnight fast of at least 10 hours, a single oral dose (320 mg) of the test product was administered to the subjects with 240 mL of drinking water at ambient temperature in sitting posture.

Dosing Under Fed Conditions

After an overnight fast of at least 10 hours, the subjects were served a high fat meal, which they consumed within 30 minutes. A single oral dose (320 mg) of the test product was administered to the subjects at 30 minutes after serving the high fat meal. The standard high fat meal consisted of: 2 eggs fried in butter, 2 strips of bacon, 2 slices of toast with butter, 4 ounces of hash brown potatoes, and 8 fluid ounces (~240 mL) of whole milk. The test product was administered in sitting posture with 240 mL of drinking water at ambient temperature.

The dosing activity was followed by a mouth and hands check to assess the compliance to dosing. The test product administration was as per the randomization schedule and under open-label conditions.

Results:

Subjects enrolled and completed both treatment periods. The mean age was 40.8 years, and the mean BMI was 26.75 kg/m$^2$.

Pharmacokinetic Results:

A summary of the descriptive statistics for the amantadine pharmacokinetic parameter values are summarized in Table 2.

TABLE 2

Descriptive Statistics of Treatment Mean Pharmacokinetic Values for Amantadine HCl ER Tablets Administered Under Fed and Fasting Conditions, Study III

| | Mean ± SD (Un-transformed data) | |
|---|---|---|
| Parameters (Units) | Test-T2 (under fed condition) | Test-T1 (under fasting condition) |
| $T_{max}$ (h)* | 9.009 (5.000-10.067) | 9.000 (5.000-10.000) |
| $C_{max}$ (ng/mL) | 726.500 ± 168.3258 | 667.406 ± 124.7239 |
| $AUC_{0-t}$ (ng · h/mL) | 16689.043 ± 4142.8550 | 17736.805 ± 4550.6428 |
| $AUC_{0-\infty}$ (ng · h/mL) | 17379.367 ± 4644.9896 | 18481.399 ± 5015.5387 |
| $\lambda_z$ (1/h) | 0.053 ± 0.0113 | 0.053 ± 0.0110 |
| $t_{1/2}$ (h) | 13.564 ± 2.9835 | 13.577 ± 3.0546 |
| AUC_% Extrap_obs (%) | 3.509 ± 2.7670 | 3.625 ± 2.7349 |
| $T_{lag}$ (h)* | 0.000 (0.000-0.667) | 0.000 (0.000-0.333) |

*$T_{max}$ and $T_{lag}$ are represented as median (min-max) value.

Conclusions

Amantadine bioavailability following oral administration of 320-mg Amantadine HCl ER Tablets under fed (Test) and fasted (Reference) conditions are equivalent. See mean profile in FIG. 1 for the relative bioavailability under fed and fasted conditions.

2.2.2 Study II (Relative Bioavailability of a Single Dose Amantadine HCl ER Tablets, 160 mg, 240 mg, and 320 mg Compared to Syrup Dose Form Study)

Study II was a single center, randomized, laboratory-blinded, four-treatment, four-period, four-sequence, single oral dose crossover design study in healthy male and female volunteers.

The primary study objectives were to evaluate dose proportionality between Amantadine HCl ER Tablets, 160 mg, 240 mg, and 320 mg and to determine the relative bioavailability of Amantadine HCl ER Tablets 160 mg compared to a reference formulation of 160 mg of Amantadine HCl syrup (50 mg/5 mL) in healthy volunteers of both genders after single dose administration under fasting conditions.

Subjects received the following treatments: Amantadine HCl 160-mg ER Tablet (Treatment A), Amantadine HCl 240-mg ER Tablet (Treatment B), Amantadine HCl 320-mg ER Tablet (Treatment C), and 160 mg Amantadine HCl 50 mg/5 mL syrup (Treatment D).

Following a 10-hour fast, subjects were orally administered their assigned treatment with 240 mL water. During each treatment period, 28 blood samples (4 mL each) were collected from each subject at predetermined times, pre-dose and through 72 hours post-dose.

Figure 2:
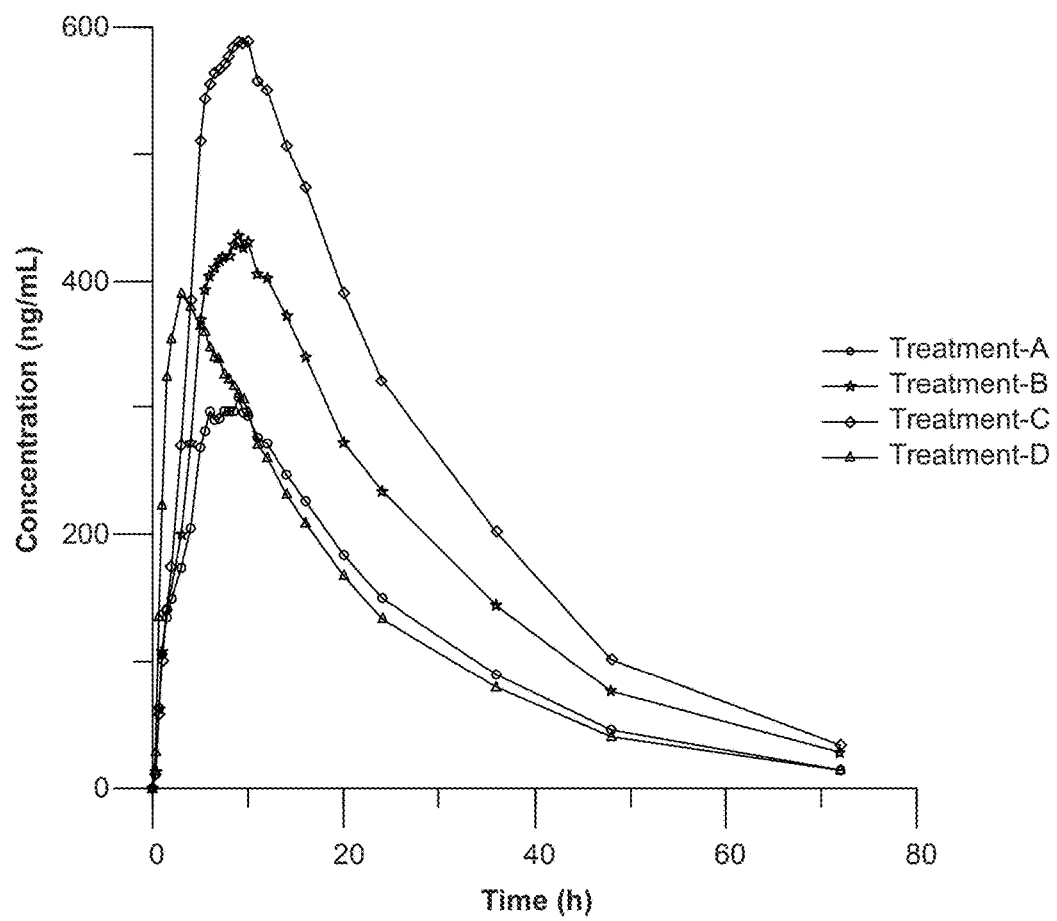
FIG. 2 depicts the mean amantadine plasma concentration-time profile following oral administration of one 160 mg (Treatment-A), 240 mg (Treatment-B) or 320 mg (Treatment-C) Amantadine HCl ER Tablet or 160 mg of Amantadine HCl Oral Syrup (Treatment-D) to 23 fasted healthy volunteers, Study II.

Results:

As shown in FIG. 2 and Table 3, longer $T_{max}$ and decreased $C_{max}$ values confirmed slower rate of amantadine absorption from the Amantadine HCl ER Tablet; $T_{max}$ occurred much later (approximately 9.00 hours post dose) for the Amantadine HCl ER Tablet compared to 3.00 hours for the oral amantadine HCl syrup; $C_{max}$ value for the 160-mg Amantadine HCl ER Tablet was 81.05% of that following administration of oral syrup.

The extent of amantadine absorption from the 160-mg Amantadine HCl ER Tablet was equivalent to that from 160 mg amantadine HCl syrup.

Plasma amantadine exposure ($C_{max}$, $AUC_{inf}$) after single oral doses (160 mg, 240 mg, 320 mg) of Amantadine HCl ER Tablets increased proportionally with increasing dose.

2.2.3 Study I (Relative Bioavailability of Amantadine HCl ER Tablets Compared to Amantadine HCl Syrup at Steady State)

Study I was a single center, laboratory-blinded, randomized, two-treatment, two-period, two-sequence, multiple oral dose crossover design study with a two-day titration period in healthy male and female volunteers.

The primary objective of the study was to determine the steady-state relative bioavailability after multiple dosing of Amantadine HCl ER Tablets, 320 mg once a day compared to the plasma profiles and pharmacokinetics parameters of an equivalent daily dose of 320 mg Amantadine HCl Oral syrup (50 mg/5 mL) divided into two equal doses in healthy volunteers of both genders under fasting conditions.

In each 9-day study period, a once daily dose of 160 mg amantadine HCl oral syrup, 50 mg/5 mL (16 mL) was administered for 2 days (titration period). Thereafter, 320 mg daily doses (one 320-mg Amantadine HCl ER Tablet once daily [Treatment A]; or 160 mg amantadine HCl oral syrup twice daily [Treatment B]) were administered for 7 consecutive days. There was at least a 7-calendar day washout period between the last morning dose of the first period and the first dose of the second period.

During each treatment period, 31 blood samples (4 mL each) were collected from each subject, for pharmacokinetic analysis at predetermined times: pre-dose and through 72 hours post-dose on Day 7.

Result: Following multiple-dose oral administration of 160-mg amantadine HCl syrup twice daily, plasma concentrations increased rapidly with a median $T_{max}$ value of 2.00 to 3.00 hours postdose ($T_{max0-12}$ and $T_{max12-24}$ was 3.00 and 14.00 hours, respectively) and thereafter declined in a log-linear manner with a terminal phase harmonic mean half-life of 13.7 hours, see FIGS. 3 and 4.

Figure 3:
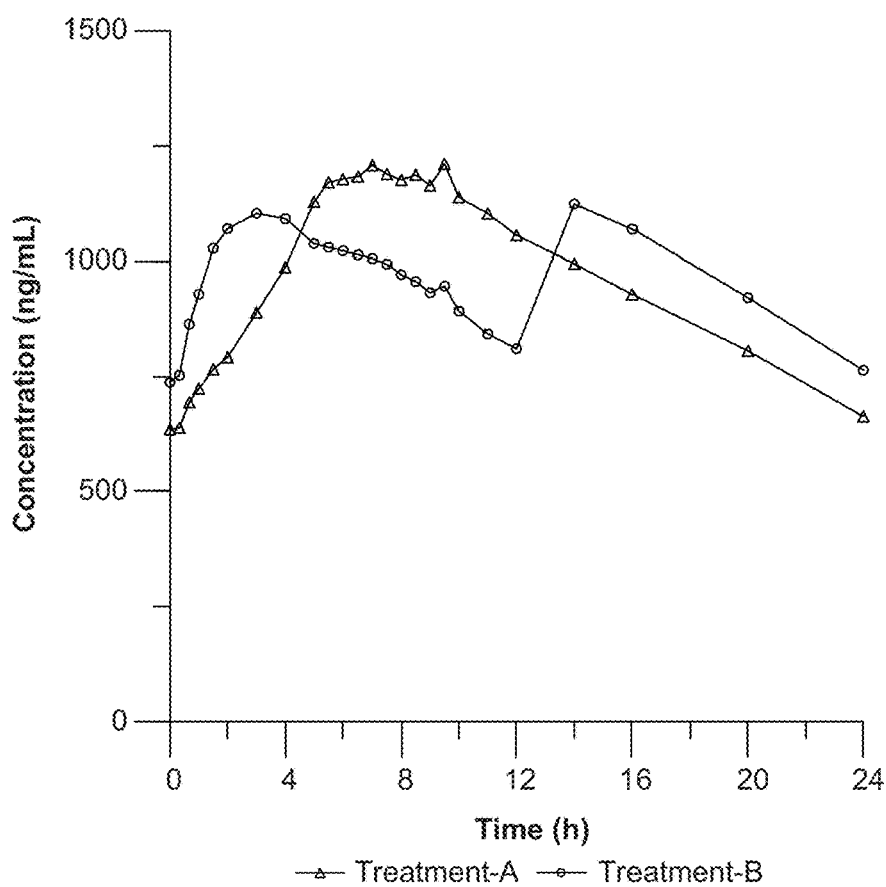
FIG. 3 depicts the amantadine plasma concentration-time (mean) profile following oral administration of one 320-mg Amantadine HCl ER Tablet daily (Treatment-A) or 160 mg of Amantadine HCl Oral Syrup, 50 mg/5 mL twice daily (Treatment-B) for 7 days to fasted healthy volunteers, Study I.
Figure 4:
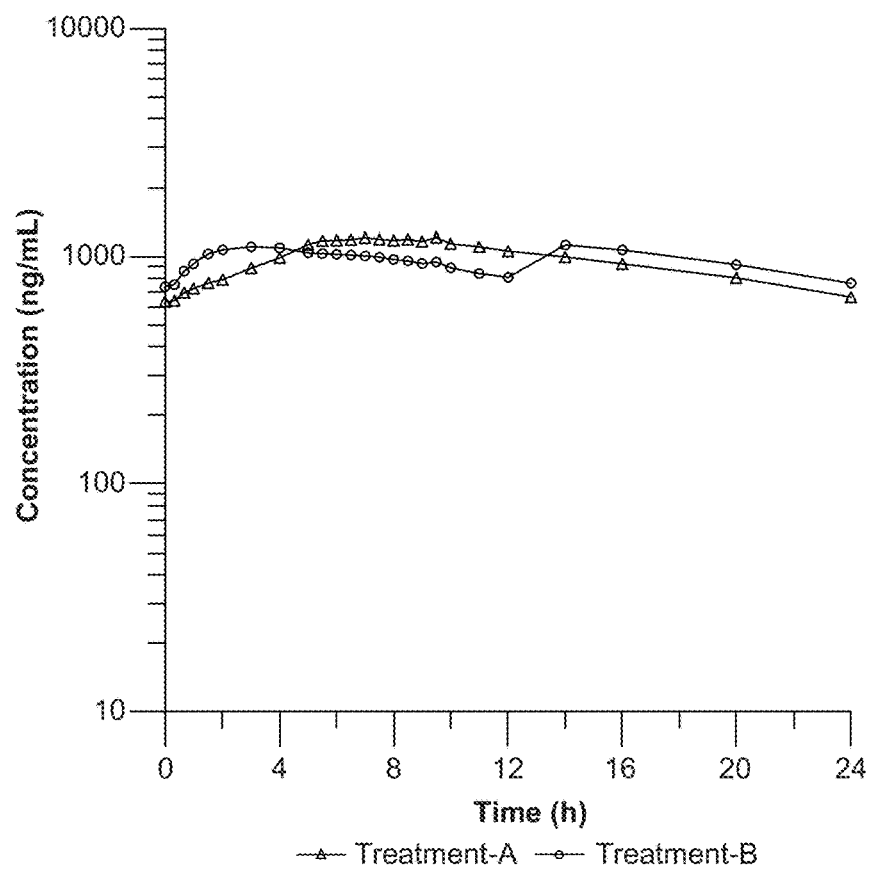
FIG. 4 depicts the amantadine plasma concentration-time (mean) profile (semi-logarithmic scale) following oral administration of one 320-mg Amantadine HCL ER Tablet daily (Treatment-A) or 160 mg of Amantadine HCl Oral Syrup, 50 mg/5 mL twice daily (Treatment-B) for 7 days to fasted healthy volunteers, Study I.

Following multiple-dose oral administration of Amantadine HCl ER 320-mg Tablets once daily, amantadine plasma concentration increased slowly with a median $T_{max0-24}$ value of 7.50 hours and thereafter declined in a log-linear manner with a terminal phase harmonic mean half-life of 13.3 hours, see FIGS. 3 and 4.

Longer $T_{max}$ values confirmed slower rate of amantadine absorption from Amantadine HCl ER Tablets; $T_{max0-24}$ value was much later (7.50 hours postdose) for Amantadine HCl ER Tablets compared to 2.00 to 3.00 hours post dose for amantadine HCl oral syrup.

TABLE 3

Summary of Mean Pharmacokinetic Parameter Values (CV %) of Amantadine Following Oral Administration of one 160 mg, 240 mg or 320 mg Amantadine HCl ER Tablet or 160 mg of Amantadine HCl Oral Syrup to Fasted Healthy Volunteers, Study II

| PARA-METER (units) | Treatment A (160 mg tablet) | | Treatment B (240 mg tablet) | | Treatment C (320 mg tablet) | | Treatment D (160 mg syrup) | |
|---|---|---|---|---|---|---|---|---|
| | Mean | (% CV) | Mean | (% CV) | Mean | (% CV) | Mean | (% CV) |
| $C_{max}$ (ng/mL) | 328.21 | (18.2) | 459.56 | (19.0) | 629.52 | (20.9) | 403.54 | (16.2) |
| $T_{max}$ (hours)[a] | 9.00 | (5.50-10.00) | 9.00 | (6.00-12.00) | 9.50 | (5.00-12.00) | 3.00 | (1.50-8.50) |
| $AUC_{0-T}$ (ng·h/mL) | 8263.28 | (17.9) | 12397.98 | (17.6) | 16931.18 | (19.9) | 8686.33 | (15.9) |
| $AUC_{0-\infty}$ (ng·h/mL) | 8580.45 | (19.0) | 13123.64 | (20.4) | 17705.51 | (21.3) | 9007.72 | (17.8) |
| $\lambda_Z$ (hours$^{-1}$) | 0.0524 | (19.8) | 0.0501 | (28.1) | 0.0515 | (20.5) | 0.0533 | (22.2) |
| $T_{half}$ (hours)[b] | 13.2 | | 13.8 | | 13.5 | | 13.0 | |

[a] Median (range),
[b] harmonic mean $T_{half}$ = 0.693/mean $\lambda_Z$

Both formulations achieved steady-state when evaluation was based on the −24, 0 and 24 hour concentrations for Day 7, thereby confirming that steady state was achieved by Day 6 (−24 hours). Mean 12-hour AUC values following the morning (11656.41 ng h/mL) and evening (11506.74 ng h/mL) syrup doses on Day 7 were similar, further suggesting steady state was achieved prior to Day 7.

At steady state, systemic exposure of amantadine from the once daily Amantadine HCl ER Tablet was similar to the twice daily syrup, further supporting bioequivalence of the formulations.

The mean $C_{avg}$ value for 320-mg Amantadine HCl ER Tablet administered once daily (947.40 ng/mL) was similar (98% to 99%) to the mean $C_{avg}$ value of 160 mg amantadine HCl syrup administered in the morning (971.37 ng/mL) and evening (958.90 ng/mL). The extent of amantadine absorption from the once-daily Amantadine HCl ER Tablet as reflected by $AUC_{0-24}$ was 97.48% of that of amantadine HCl syrup. Inspection of amantadine HCl syrup $C_{max}$ values for each 12-hour dosing interval and for the 24-hour sample interval revealed that $C_{max}$ values for twice daily administration of 160-mg immediate-release amantadine HCl syrup, 50 mg/5 mL were comparable to that for once daily administration of 320-mg Amantadine HCl ER Tablets, see Table 4.

The $C_{min}$ value following oral administration of one Amantadine HCl ER Tablet daily was slightly lower than that following twice daily administration of amantadine HCl syrup; the geometric least squares mean values were 565.68 and 695.90, respectively.

Bioequivalence

At steady state, the 320-mg Amantadine HCl ER Tablet is bioequivalent to 320 mg/day amantadine HCl syrup (160 mg twice daily).

Conclusion

Amantadine is slowly absorbed from 320-mg Amantadine HCl ER Tablets. Steady state is achieved by the 6th day of multiple dose administration of 320-mg Amantadine HCl ER Tablets once daily and 160 mg amantadine HCl oral syrup, 50 mg/5 mL twice daily. At steady state, 320-mg Amantadine HCl ER Tablets are bioequivalent to 320 mg/day amantadine HCl oral syrup, 50 mg/5 mL (160 mg administered twice daily).

TABLE 4

Mean Pharmacokinetic Parameter Values (CV %) of Amantadine Following Oral Administration of One 320-mg Amantadine HCl ER Tablet Daily (Treatment-A) or 160 mg Amantadine HCl Oral Syrup Twice Daily (Treatment-B) to Fasted Healthy Volunteers, Study I

| PARAMETER | Treatment-A[a] | | Treatment-B[b] | |
|---|---|---|---|---|
| | MEAN | C.V. (%) | MEAN | C.V. (%) |
| $C_{min0-12}$ (ng/mL) | NC | NC | 747.53 | (27.0) |
| $C_{min0-24}$ (ng/mL) | 612.19 | (39.5) | 724.34 | (28.8) |
| $C_{max0-12}$ (ng/mL) | NC | NC | 1129.02 | (19.6) |
| $C_{max12-24}$ (ng/mL) | NC | NC | 1140.03 | (19.2) |
| $C_{max0-24}$ (ng/mL) | 1275.01 | (21.6) | 1165.90 | (18.9) |
| $T_{max0-12}$ (hours)c | NC | NC | 3.00 | (2.00-7.50) |
| $T_{max12-24}$ (hours)c | NC | NC | 14.00[e] | (14.00-20.00) |
| $T_{max0-24}$ (hours)c | 7.50 | (5.00-11.95) | 14.00[e] | (2.00-20.00) |
| $AUC_{0-12}$ (ng · h/mL) | NC | NC | 11656.41 | (21.8) |
| $AUC_{12-24}$ (ng · h/mL) | NC | NC | 11506.74 | (22.5) |
| $AUC_{0-24}$ (ng · h/mL) | 22737.52 | (24.7) | 23163.15 | (22.0) |
| $C_{avg0-12}$ (ng/mL) | NC | NC | 971.37 | (21.8) |
| $C_{avg12-24}$ (ng/mL) | NC | NC | 958.90 | (22.5) |
| $C_{avg0-24}$ (ng/mL) | 947.40 | (24.7) | 965.13 | (22.0) |
| $C_{pd(-48)}$ (ng/mL) | 609.08 | (36.5) | 692.18 | (26.2) |
| $C_{pd(-24)}$ (ng/mL) | 662.28 | (35.4) | 750.17 | (26.7) |
| $C_{pd(0)}$ (ng/mL) | 634.58 | (39.6) | 736.85 | (27.8) |
| $C_{24}$ (ng/mL) | 662.70 | (33.6) | 762.75 | (29.8) |
| $\lambda_z$(hours-1) | 0.0521 | (27.6) | 0.0505 | (27.3) |
| $T_{half}$ (hours) [d] | 13.3 | NA | 13.7 | NA |

NA = not applicable; NC = not calculated
[a]Treatment-A = Amantadine HCl 320 mg ER tablet once daily
[b]Treatment-B = Amantadine HCl 160 mg dose oral solution twice daily, 50 mg/5 mL
[c]Median (range)
[d]harmonic mean half-life ($T_{half}$ = 0.693/mean $\lambda_z$)
[e]14.00 hours is 2.00 h postdose Example 3

In Vitro Dissolution

Amantadine HCl ER Tablets were analyzed in various media to confirm the extended release of amantadine HCl from Amantadine HCl ER Tablets. Three Amantadine HCl ER Tablets were manufactured as described in Example 1 and the dissolution profile data are presented in FIGS. 5-7. The dissolution profiles of extended release cores for each of the three strengths (160 mg, 240 mg, and 320 mg) have also been characterized in the following four dissolution media: 1) water (drug product test method) 2) 0.1 N HCl, 3) pH 4.5 acetate buffer and 4) pH 6.8 phosphate buffer.

All 3 strengths (160 mg, 240 mg, and 320 mg of amantadine HCl) are soluble in 250 mL water, and sink conditions (concentration is less than 20% of solubility of amantadine HCl).

3.1 Dissolution in Water

The dissolution test method for Amantadine HCl ER Tablets is summarized in Table 5.

In vitro dissolution data revealed slow release of amantadine HCl from Amantadine HCl ER Tablets, 160 mg, 240 mg and 320 mg. Slow release of amantadine HCl from Amantadine HCl ER Tablets was reflected in the relatively long $T_{max}$ values (9 hours) in the bioavailability studies which confirmed slow absorption of amantadine after oral administration of Amantadine HCl ER Tablets, 160 mg, 240 mg and 320 mg.

TABLE 5

Summary of Dissolution Test Method for Amantadine HCl ER Tablets, 160 mg, 240 mg and 320 mg

| Apparatus | USP Apparatus 2 Paddles |
|---|---|
| Temperature | 37.0 ± 0.5° C. |
| Speed | 50 rpm |
| Volume | 900 mL |
| Dissolution medium | Purified water |
| Draw volume | 9 mL |
| Offset[1] | 3 mL |

TABLE 5-continued

Summary of Dissolution Test Method for Amantadine
HCl ER Tablets, 160 mg, 240 mg and 320 mg

| Apparatus | USP Apparatus 2 Paddles |
|---|---|
| Flush time[1] | 1 time |
| Flush volume[1] | 10 mL (recycle Option - ON) |
| Pull times | 0.5 hour, 2.5 hour, 4 hour, and 8 hour |
| Analytical method | HPLC |
| Test method reference | AP-0057 |

[1]Auto-sampler parameters for Distek Evolution 4300 Dissolution Auto-sampler.

A summary of the dissolution profiles for the amantadine extended release tablet cores in water is shown in Table 6.

TABLE 6

Summary of Dissolution of the Extended Release Core
of Amantadine HCl ER Tablets, 160 mg, 240 mg and 320 mg

| Strength | | 320 mg | | | |
|---|---|---|---|---|---|
| % Dissolved at Time (Hr) Mean (Min - Max) | 1 h | 3 (1-4)[1] | 9 (4-10) | 6 (5-8) | 5 (2-7) |
| | 2.5 h | 27 (21-36)[1] | 43 (31-55) | 43 (40-47) | 39 (29-46) |
| | 4 h | 55 (47-63)[1] | 67 (56-78) | 68 (66-71) | 66 (58-71) |
| | 6 h | 79 (73-85)[1] | 86 (80-93) | 88 (87-91) | 88 (83-91) |
| | 8 h | 92 (88-94)[1] | 94 (91-97) | 96 (95-97) | 95 (94-98) |
| Strength | | 240 mg | | | |
| % Dissolved at Time (Hr) Mean (Min - Max) | 1 h | 1 (0-3) | 2 (1-5)[1] | 1 (1-3) | 1 (0-2) |
| | 2.5 h | 16 (5-32) | 23 (13-45)[1] | 23 (12-36) | 22 (11-31) |
| | 4 h | 54 (43-71) | 54 (45-73)[1] | 56 (45-67) | 55 (42-63) |
| | 6 h | 85 (76-92) | 82 (76-91)[1] | 84 (77-91) | 84 (75-88) |
| | 8 h | 96 (99-92) | 92 (89-97)[1] | 93 (91-96) | 94 (91-97) |
| Strength | | 160 mg | | | |
| % Dissolved at Time (Hr) Mean (Min - Max) | 1 h | 1 (0-3) | 2 (1-3) | 3 (2-8) | |
| | 2.5 h | 25 (8-40) | 24 (13-34) | 31 (18-56) | |
| | 4 h | 65 (54-74) | 62 (49-72) | 68 (60-86) | |
| | 6 h | 90 (86-93) | 89 (84-91) | 91 (88-96) | |
| | 8 h | 96 (95-98) | 96 (95-97) | 97 (95-99) | |

[1]Did not meet dissolution criteria.

3.2 Dissolution in Various Media

The effect of dissolution media on drug release from Amantadine HCl ER Tablets was also examined. A comparison of the profiles by strength is provided in FIG. 5 through FIG. 7. As expected, the dissolution profile of these osmotic pump tablets is relatively insensitive to the dissolution media. The dissolution profiles were comparable ($f_2 > 50$) in water vs 0.1 N HCl and pH 4.5 buffer. The profiles were also comparable in 0.1 N HCl vs pH 6.8 buffer, but they were not considered comparable ($f_2 < 50$) in water or pH 4.5 vs pH 6.8.

The dissolution profile of Amantadine HCl ER Tablets, 160 mg, 240 mg and 320 mg in water (QC dissolution medium) for each of the three registration batches was similar with each other.

After release of the 60-mg immediate-release portion of the tablet, the release rate of amantadine HCl from Amantadine HCl ER Tablets in 0.1 N HCl, pH 4.5 acetate buffer, or pH 6.8 phosphate buffer was similar for all three strengths.

The dissolution of these osmotic pump tablets is relatively insensitive to the dissolution media.

3.3 Ethanol Dissolution

In vitro drug dissolution studies (using 12 tablets) were conduct to evaluate the potential of alcohol induced dose dumping. Drug release for all product strengths at ethanol levels of 0%, 5%, 20% and 40% in 0.1N HCl (pH 1.2) and in water (media of the drug product [QC] dissolution method) were measured employing the chromatographic parameters. Table 5.

3.3.1 Ethanol Impact on Amantadine HCl Immediate-Release Portion

All tablet strengths contained 60 mg amantadine HCl in an IR layer which was coated onto the extended-release tablet core; 60 mg is 38%, 25% and 19% of the label claim (LC) for the 160-mg, 240-mg and 320-mg ER tablets, respectively. The amount of ethanol in water or 0.1N HCl did not affect the amount released in 30 minutes for any of the strengths; mean amount released values ranged from 53 to 70 mg amantadine HCl.

3.3.2 Impact on Extended Release Properties 3.3.2.1 160 mg ER Tablets

Figure 8:
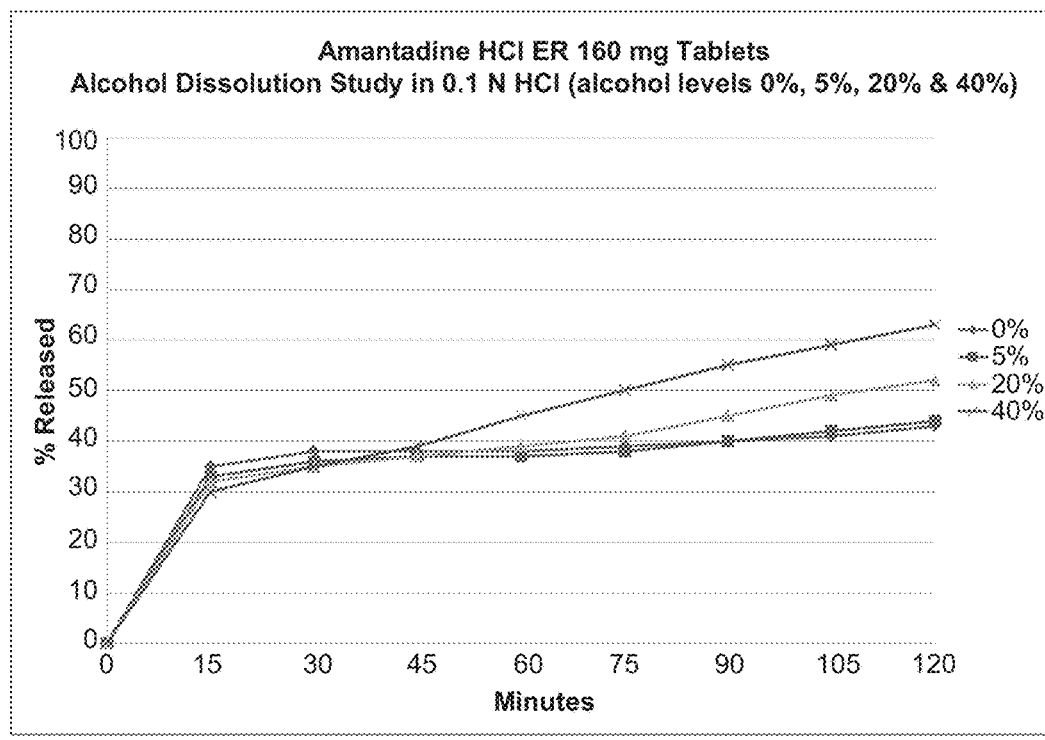
FIG. 8 depicts alcohol effect on the dissolution profile of Amantadine HCl ER 160-mg Tablets in 0.1 N HCl.
Figure 9:
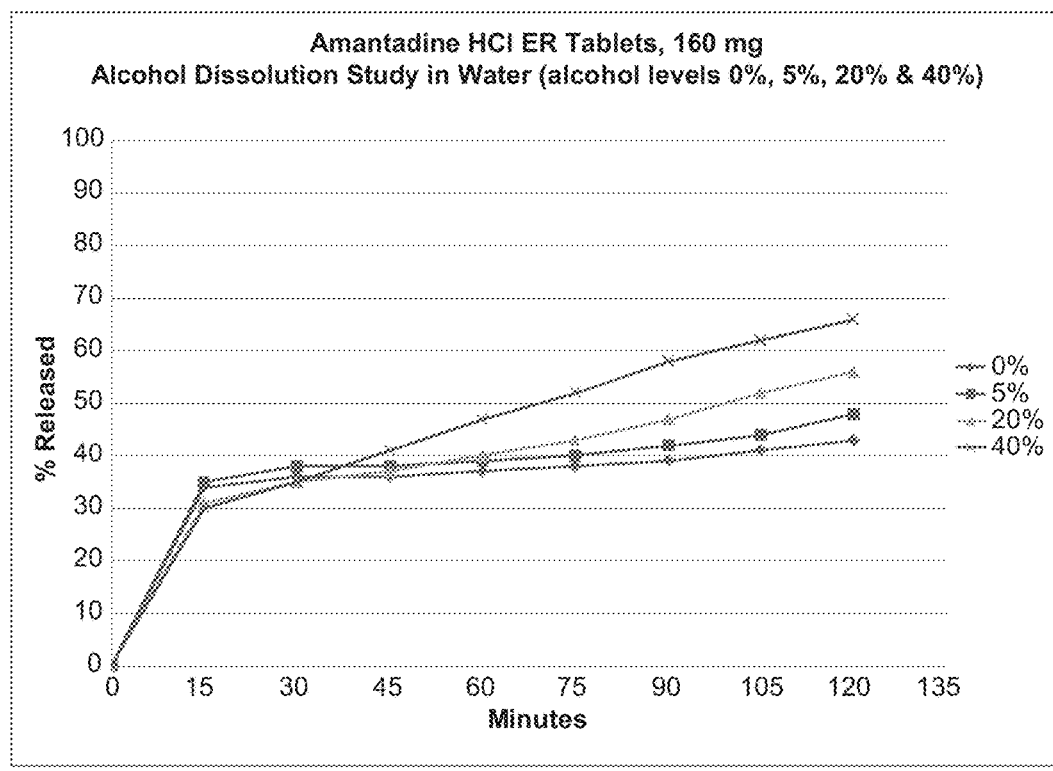
FIG. 9 depicts alcohol effect on the dissolution profile of Amantadine HCl ER 160-mg Tablets in water.

As shown in, FIG. 8 and FIG. 9, levels of ethanol up to 20% in acidic and QC media did not affect the release profile of the 160-mg tablets, $f_2$ values were greater than 50, see Table 7.

TABLE 7

Summary of Comparison of Amantadine HCl Dissolution
Profiles for 160-mg Amantadine HCl ER Tablets in Acidic (0.1 N
HCl) or QC (Water) Media Containing 0%, 5%, 20% and 40% Ethanol

| Dissolution Media | f2 value | Amount dissolved (mg) in 2 hours | Amount dissolved (% LC) in 2 hours |
|---|---|---|---|
| 0% EtOH/0.1 N HCl | NA | 69 mg | 43% |
| 5% EtOH/0.1 N HCl | 90 | 70 mg | 44% |
| 20% EtOH/0.1 N HCl | 65 | 83 mg | 52% |
| 40% EtOH/0.1 N HCl | 46 | 101 mg | 63% |
| 0% EtOH/water | NA | 69 mg | 43% |
| 5% EtOH/water | 77 | 77 mg | 48% |
| 20% EtOH/water | 57 | 90 mg | 56% |
| 40% EtOH/water | 42 | 106 mg | 66% |

Compared to 0% ethanol, the amount released over the 2-hour period in 40% ethanol increased by only 32 mg and 37 mg in 0.1 N HCl and water, respectively (32% and 37% of the 100 mg amantadine HCl in the extended-release tablet core of 160-mg ER tablet). Inspection of the dissolution profiles revealed that the Amantadine HCl ER 160-mg Tablets maintained their extended-release properties. The profile maintained its pseudo-zero order characteristic; the release profile was linear from 30 minutes to 120 minutes. Moreover, the maximum amount released in 2 hours was only 101 mg or 106 mg amantadine HCl, approximately one-half of an amantadine HCl oral solution dose of 200 mg.

These results confirm that Amantadine HCl ER 160-mg Tablets do not dose dump in ethanol solutions containing up to 40% ethanol, as shown in Table 8 and Table 9.

TABLE 8

160-mg Amantadine HCl ER Tablets - Mean Amount Amantadine HCl Released in 0.1 N HCl and 0%, 5%, 20% and 40% Ethanol Over a Two-Hour Period

| % Ethanol | 15 min | 30 min | 45 min | 60 min | 75 min | 90 min | 105 min | 120 min |
|---|---|---|---|---|---|---|---|---|
| Mean Amount Released (% Label Claim) by Sample Time (minutes) | | | | | | | | |
| 0 | 35 | 38 | 38 | 38 | 39 | 40 | 41 | 43 |
| 5 | 33 | 36 | 37 | 37 | 38 | 40 | 42 | 44 |
| 20 | 32 | 35 | 37 | 39 | 41 | 45 | 49 | 52 |
| 40 | 30 | 35 | 39 | 45 | 50 | 55 | 59 | 63 |
| Mean Amount Released (mg) by Sample Time (minutes) | | | | | | | | |
| 0 | 56 | 61 | 61 | 61 | 62 | 64 | 66 | 69 |
| 5 | 53 | 58 | 59 | 59 | 61 | 64 | 67 | 70 |
| 20 | 51 | 56 | 59 | 62 | 66 | 72 | 78 | 83 |
| 40 | 48 | 56 | 62 | 72 | 80 | 88 | 94 | 101 |

TABLE 9

160-mg Amantadine HCl ER Tablets - Mean Amount Amantadine HCl Released in Water and 0%, 5%, 20% and 40% Ethanol Over a Two-Hour Period

| % Ethanol | 15 min | 30 min | 45 min | 60 min | 75 min | 90 min | 105 min | 120 min |
|---|---|---|---|---|---|---|---|---|
| Mean Amount Released (% Label Claim) by Sample Time (minutes) | | | | | | | | |
| 0 | 34 | 36 | 36 | 37 | 38 | 39 | 41 | 43 |
| 5 | 35 | 38 | 38 | 39 | 40 | 42 | 44 | 48 |
| 20 | 31 | 35 | 37 | 40 | 43 | 47 | 52 | 56 |
| 40 | 30 | 35 | 41 | 47 | 52 | 58 | 62 | 66 |
| Mean Amount Released (mg) by Sample Time (minutes) | | | | | | | | |
| 0 | 54 | 58 | 58 | 59 | 61 | 62 | 66 | 69 |
| 5 | 56 | 61 | 61 | 62 | 64 | 67 | 70 | 77 |
| 20 | 50 | 56 | 59 | 64 | 69 | 75 | 83 | 90 |
| 40 | 48 | 56 | 66 | 75 | 83 | 93 | 99 | 106 |

Figure 10:
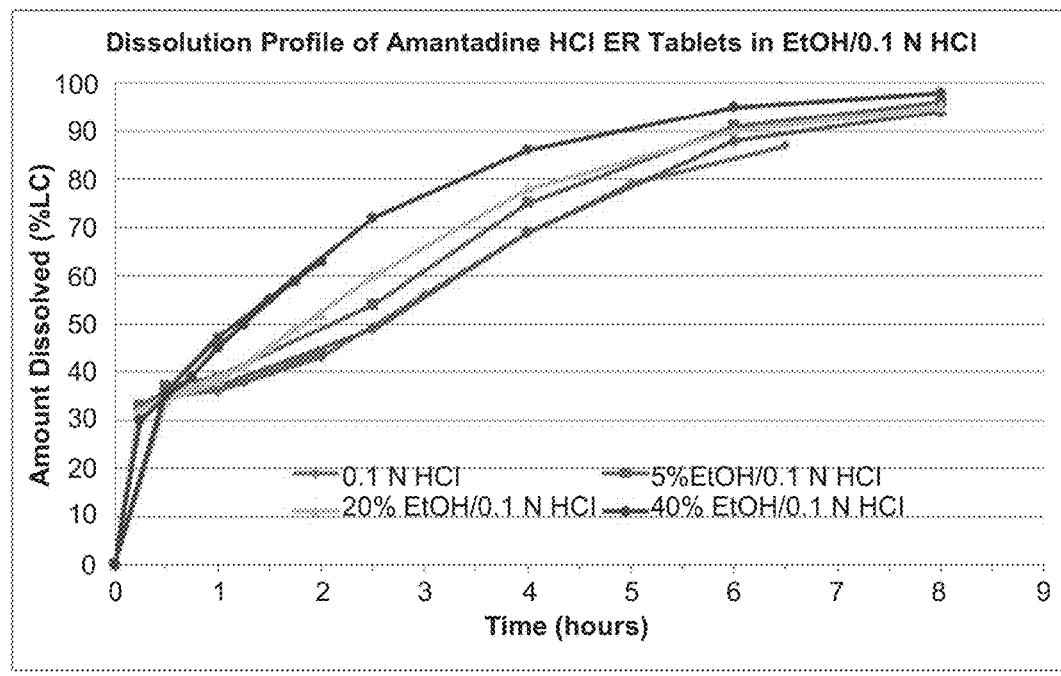
FIG. 10 depicts alcohol effect on the dissolution profile of Amantadine HCl ER 160-mg Tablets (0.1 N HCl media) over two-hour and eight-hour periods.
Figure 11:
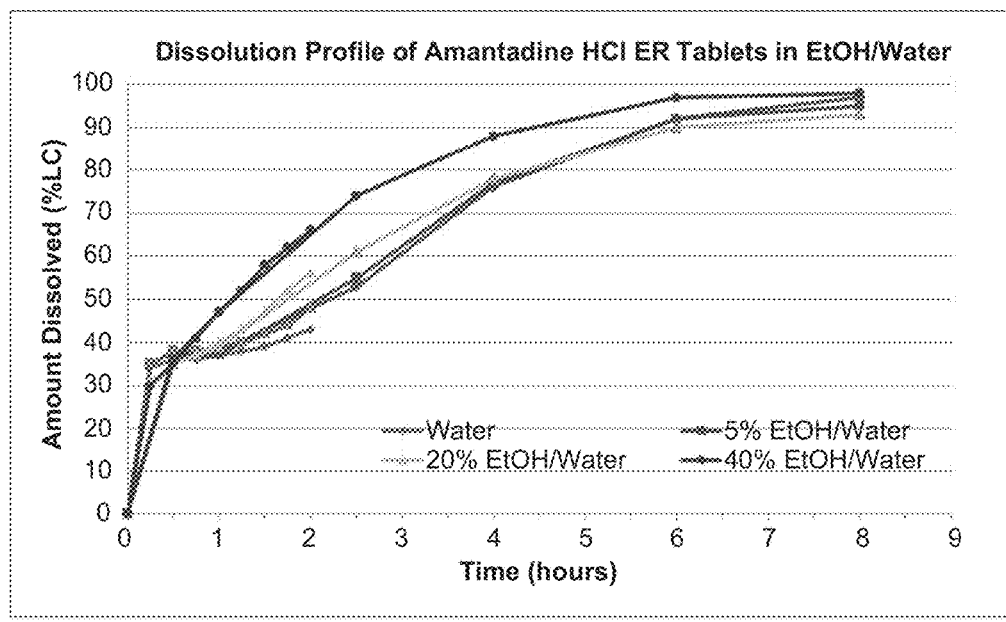
FIG. 11 depicts alcohol effect on the dissolution profile of Amantadine HCl ER 160-mg Tablets in water media over two-hour and eight-hour periods.

Characterization of the profile for 8 hours was performed for the 160-mg tablets. The impact of ethanol on the dissolution profile was examined further for the 160-mg Amantadine HCl ER Tablets as this strength was affected the most in the 2-hour studies. FIG. 10 and FIG. 11 include data from both the 2-hour and 8-hour alcohol interaction studies, and show that levels of ethanol up to 20% in both acidic and QC media did not affect the release profile of the 160-mg tablets over the 8 hour period, $f_2$ values were greater than 50. In 40% ethanol, the $f_2$ values were below 50 for both the acidic ($f_2$=43) and QC media ($f_2$=46), but inspection of the dissolution profiles and the amount of amantadine HCl released confirm that the Amantadine HCl ER 160-mg Tablets do not dose dump in ethanol solutions containing up to 40% ethanol.

3.3.2.2 240 mg ER Tablets

Figure 12:
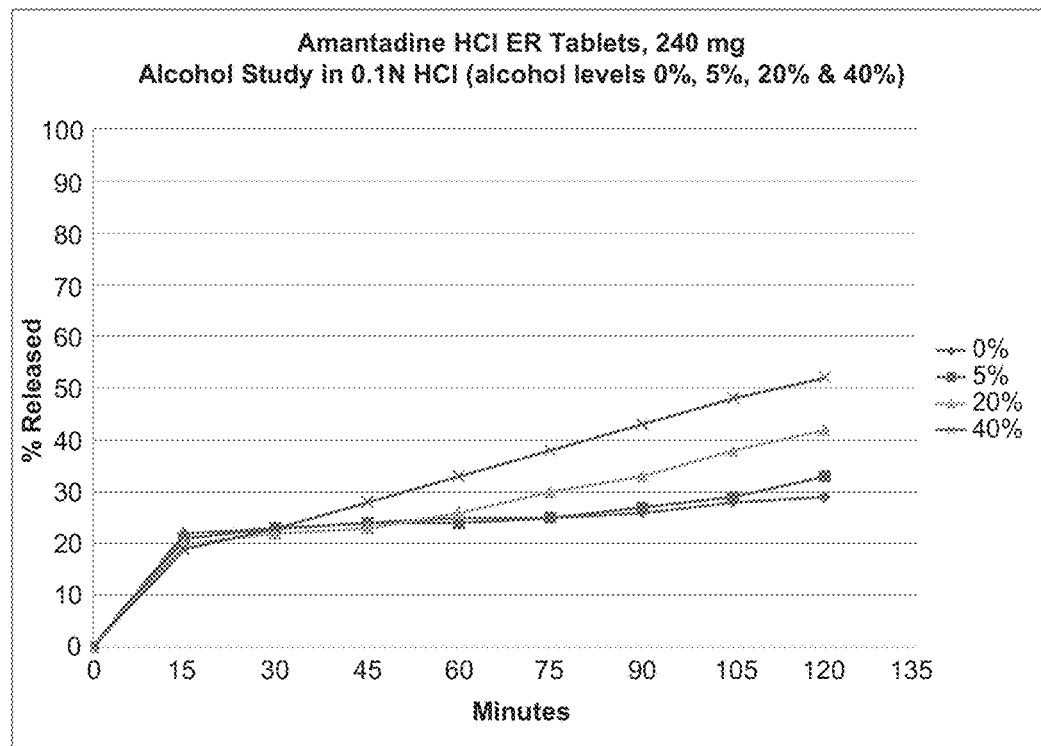
FIG. 12 depicts alcohol effect on the dissolution profile of Amantadine HCl ER 240-mg Tablets in 0.1 N HCl.
Figure 13:
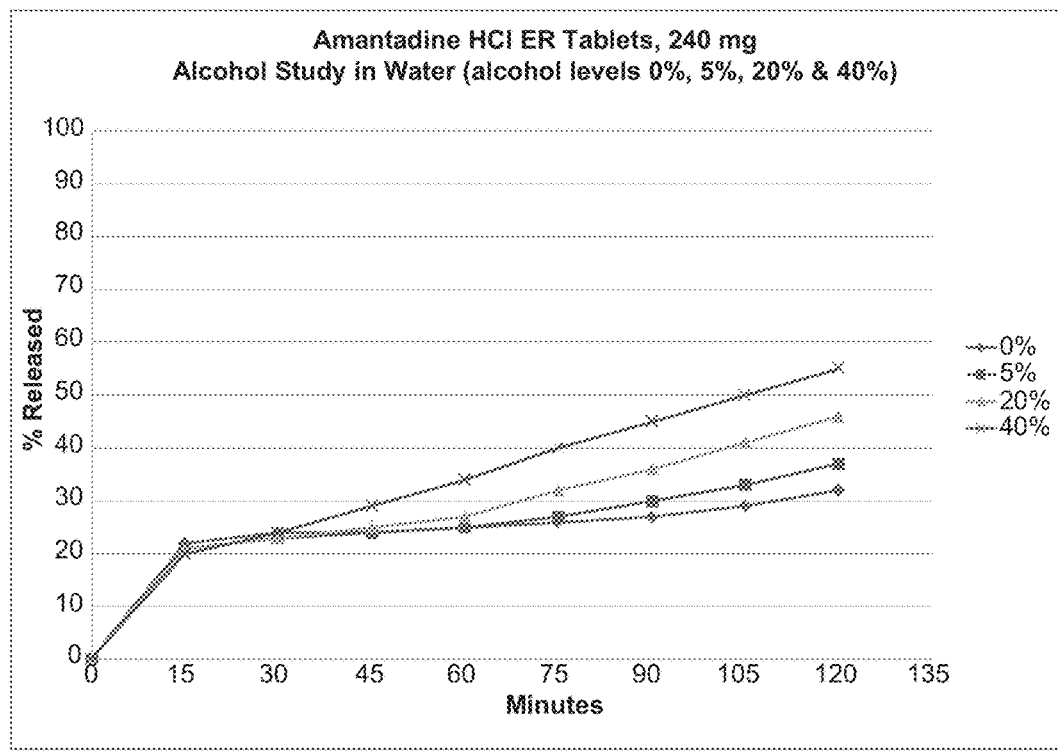
FIG. 13 depicts alcohol effect on the dissolution profile of Amantadine HCl ER 240-mg Tablets in water.

The dissolution study of 240 mg ER Tablets was conducted using the same test method as shown in Table 5 and in the same media as 160 mg ER tablets. FIG. 12 and FIG. 13 show the result of the dissolution study. These results confirmed that Amantadine HCl ER 240-mg tablets, similar to the 160 mg tablets, do not dose dump in ethanol solutions containing up to 40% ethanol.

3.3.2.3 320 mg ER Tablets

Figure 14:
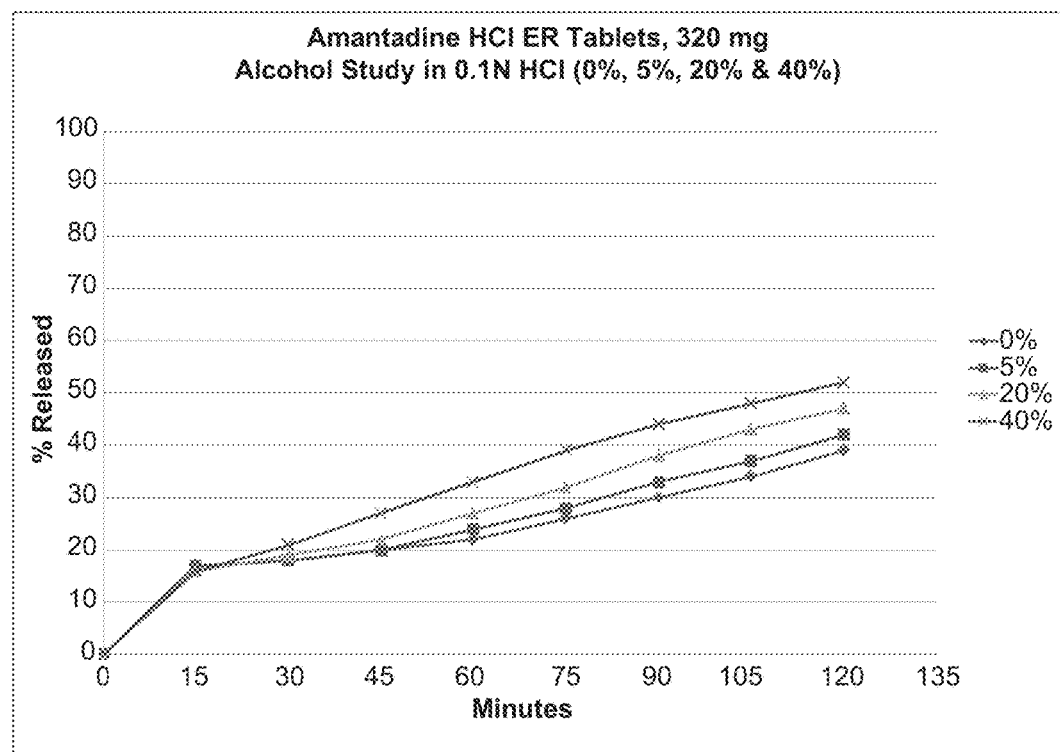
FIG. 14 depicts alcohol effect on the dissolution profile of Amantadine HCl ER 320-mg Tablets in 0.1 N HCl.
Figure 15:
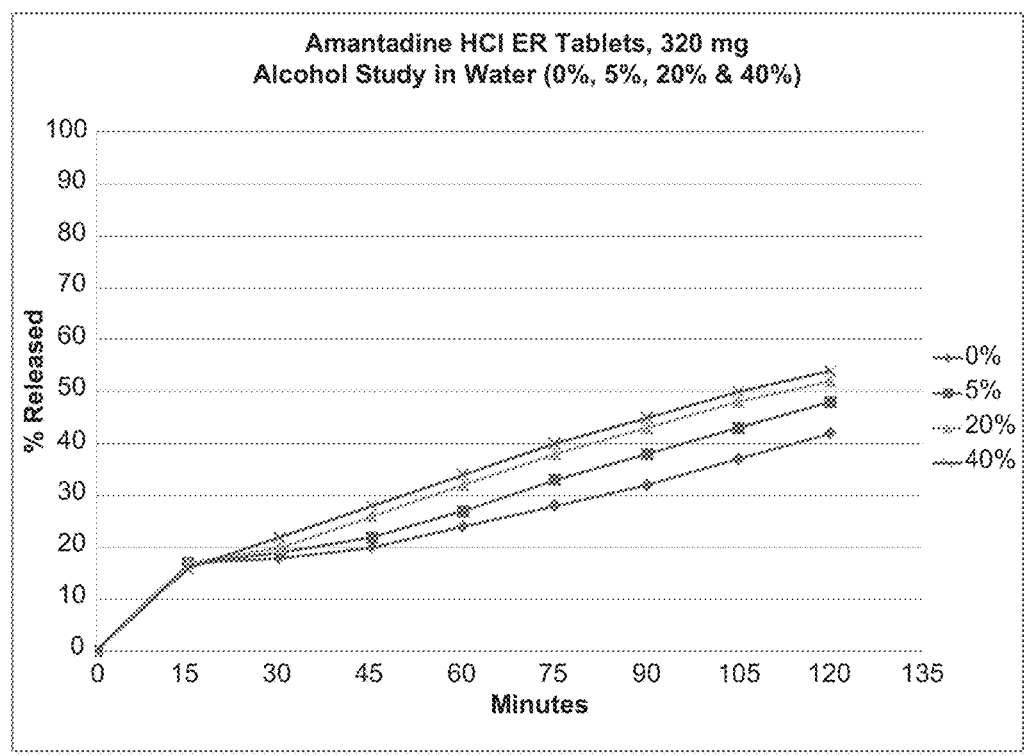
FIG. 15 depicts alcohol effect on the dissolution profile of Amantadine HCl ER 320-mg Tablets in water.

The dissolution study of 320 mg ER Tablets was conducted using the same test method as shown in Table 5 and in the same media as 160 mg ER tablets. FIG. 14 and FIG. 15 show the result of the dissolution study. These results confirmed that the Amantadine HCl ER 320-mg tablets, similar to the 160 mg tablets, do not dose dump in ethanol solutions containing up to 40% ethanol.

3.3.3 Conclusions

Examination of amantadine HCl dissolution profiles in 40% ethanol in acidic (0.1 N HCl) or QC (water) media revealed that Amantadine HCl ER 160-mg, 240-mg, and 320-mg tablets maintained their extended-release properties. The profile maintained its pseudo-zero order characteristic; the release profile was linear from 30 minutes to 120 minutes. The maximum increase in amantadine HCl release induced by the addition of up to 40% ethanol was only 37%, 34% and 16% of the amount of amantadine HCl in the extended release tablet core for the 160-mg, 240-mg and 320-mg ER Tablets, respectively. Moreover, the maximum amount released in 2 hours for the 160-mg, 240-mg and 320-mg ER Tablets was only 53%, 66% and 87% of the dose of a 200-mg immediate-release amantadine HCl oral solution dose.

Further examination of amantadine HCl dissolution profiles for 160-mg Amantadine HCl ER Tablets in up to 40% ethanol for 8 hours confirmed the absence of dose dumping.

Dissolution media containing up to 40% ethanol does not compromise the release-rate controlling mechanism of the extended-release tablet core of Amantadine HCl ER Tablets. Amantadine HCl ER Tablets do not dose dump in ethanol solutions containing up to 40% ethanol.

Example 4

Study to Confirm Extended Release for Amantadine HCl ER Tablets

Amantadine HCl immediate-release products (tablet, capsule, syrup (solution)) are administered twice daily. Amantadine HCl ER Tablets have been developed for once daily administration. All three strengths (160 mg, 240 mg, and 320 mg) of Amantadine HCl ER Tablets provide 60 mg as an immediate-release dose, and the remainder of the amantadine HCl dose is contained in the extended-release tablet core.

Figure 5:
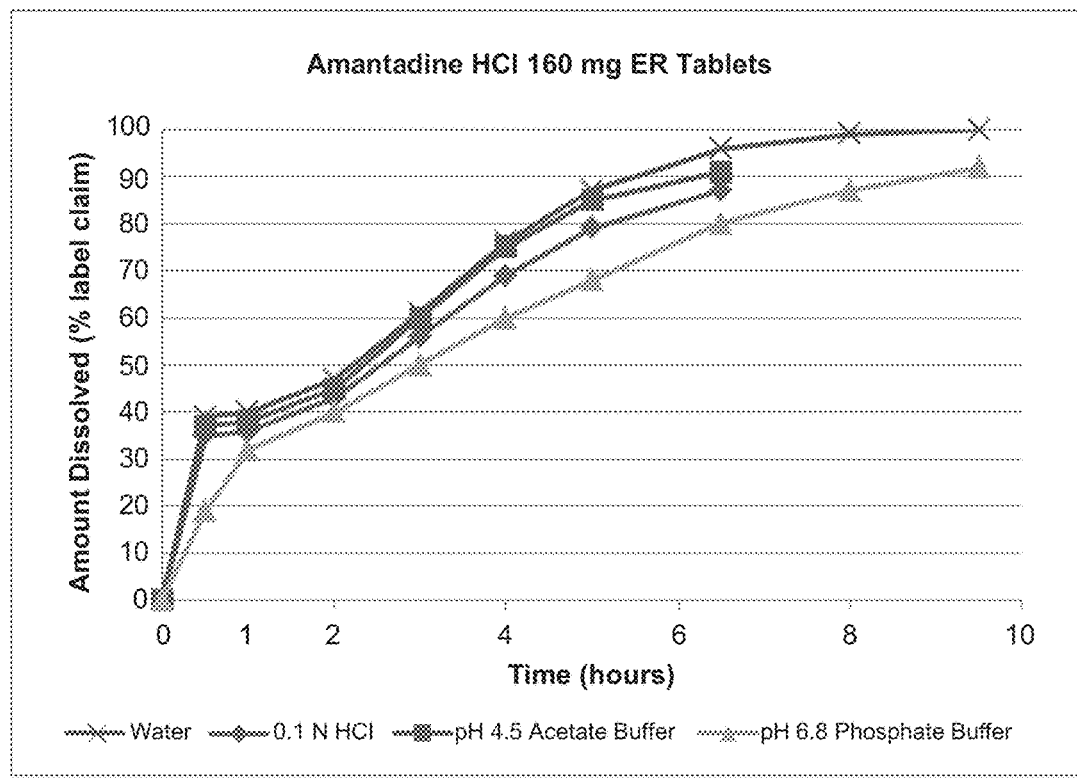
FIG. 5 depicts the dissolution profile of Amantadine HCl ER Tablets, 160 mg in various dissolution media.
Figure 6:
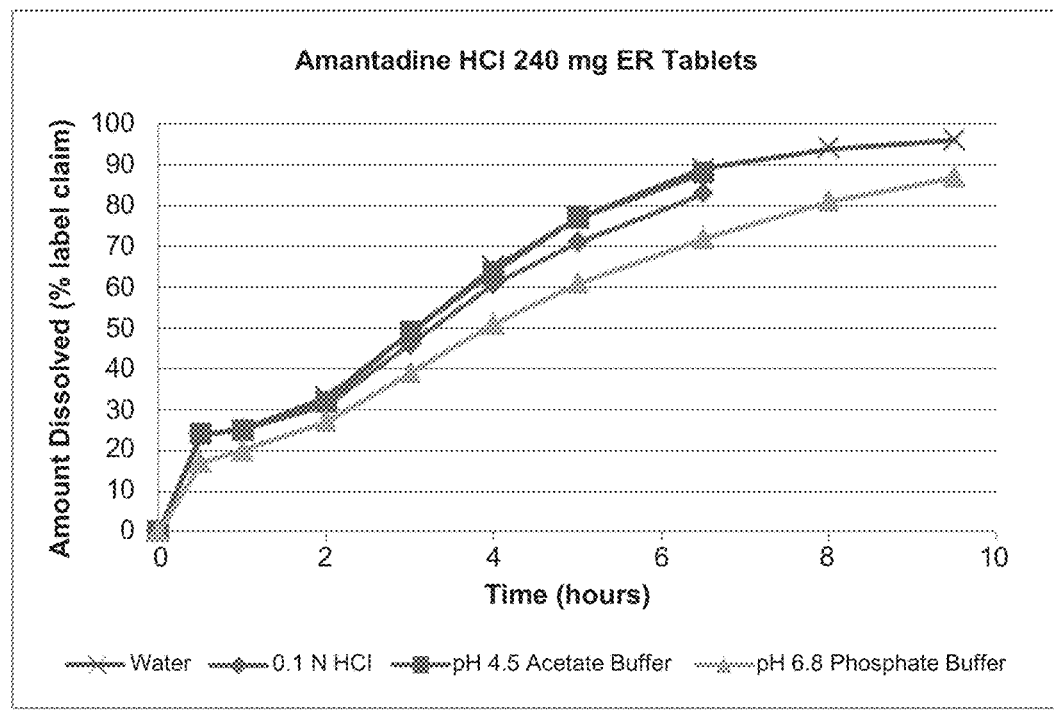
FIG. 6 depicts the dissolution profile of Amantadine HCl ER Tablets, 240 mg in various dissolution media.
Figure 7:
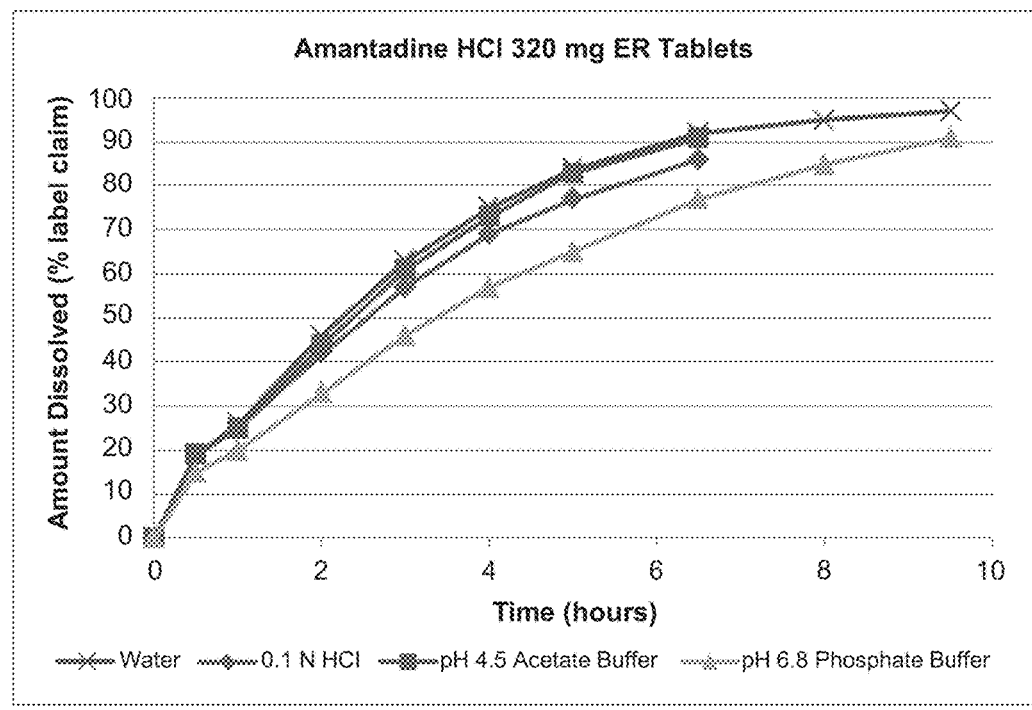
FIG. 7 depicts the dissolution profile of Amantadine HCl ER Tablets, 320 mg in various dissolution media.

In vitro dissolution studies confirm that amantadine HCl is slowly released over 8 hours from Amantadine HCl ER Tablets, see FIGS. 5-7.

The 3 bioavailability studies in Example 2 were also conducted to further characterize the extended-release properties of Amantadine HCl ER Tablets.

The reference material for these bioavailability studies was Amantadine HCl Oral Syrup, 50 mg/5 mL, an approved drug product solution, of the active ingredient (amantadine HCl).

Longer $T_{max}$ values in Study II revealed that amantadine is slowly absorbed following single oral dose administration of Amantadine HCl ER Tablets, 160 mg, 240 mg or 320 mg. Amantadine plasma exposure ($C_{max}$, $AUC_{0-\infty}$) increased dose proportionally following oral administration of single doses of 160-mg, 240-mg, and 320-mg Amantadine HCl ER Tablets. The extent of amantadine absorption (AUC) from the 160-mg ER tablet is equivalent to that from 160 mg Amantadine HCl Oral Syrup, 50 mg/5 mL.

Figure 16:
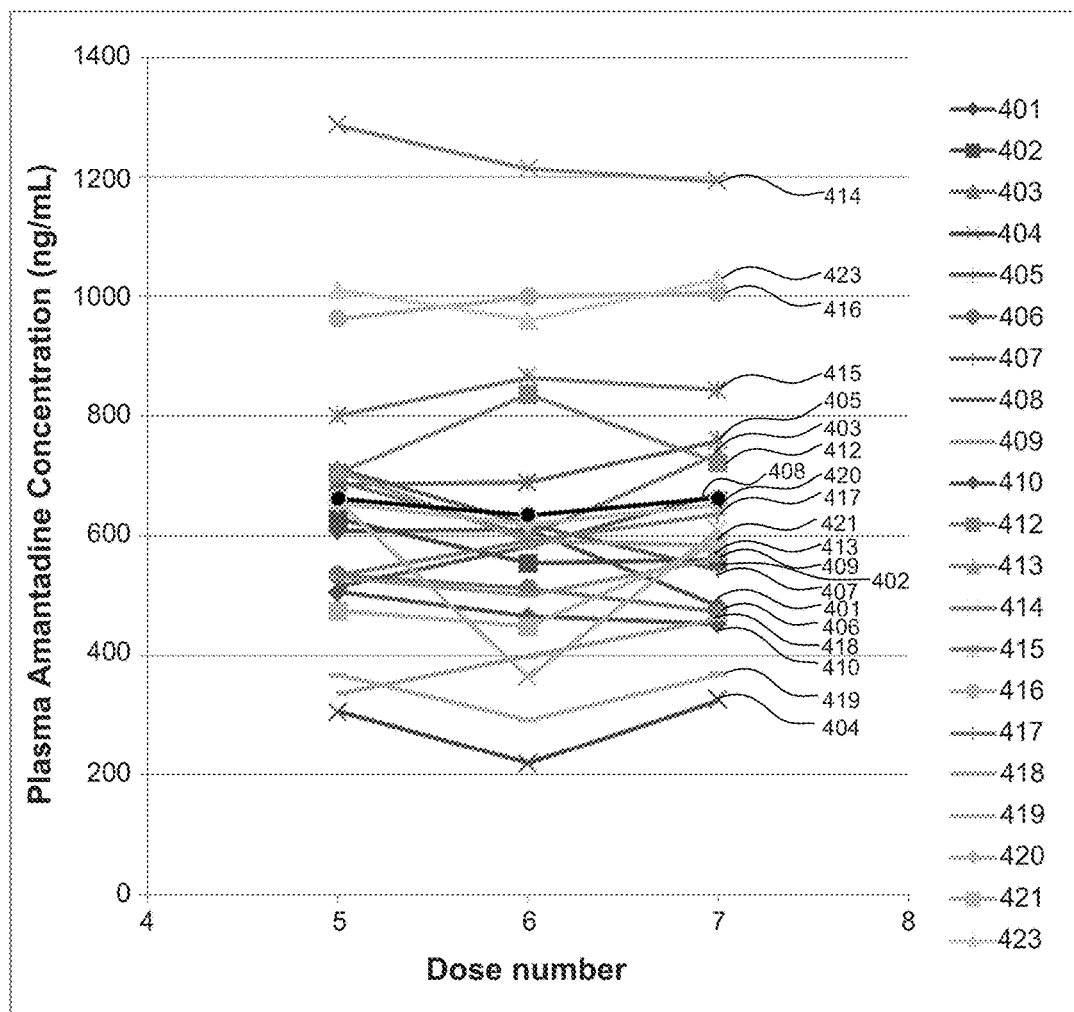
FIG. 16 depicts the individual and mean amantadine plasma concentration 24 hours after dose 5, 6 and 7 of Amantadine HCl ER Tablets, 320 mg. Study I.

Furthermore, following multiple-dose, once-daily, steady state administration in Study I, Amantadine HCl ER Tablets 320 mg were bioequivalent to 320 mg Amantadine HCl Oral Syrup (160 mg twice daily). Thereby confirming that the drug product's steady-state performance is equivalent to a currently marketed non-extended-release drug product that contains the same active drug ingredient or therapeutic moiety and that is subject to an approved full new drug application. Inspection of individual and mean subject data following once-daily oral administration of Amantadine HCl ER Tablets for 7 days revealed that the amantadine plasma concentration values 24 hours after dose 5, 6 and 7 administration were consistent, see FIG. 16.

Study III revealed that amantadine bioavailability following oral administration of 320-mg Amantadine HCl ER Tablets with a high fat meal (fed, Test) is equivalent to fasted (Reference). No significant food effect was observed, thereby ruling out the occurrence of any dose dumping.

Example 5

Pharmacokinetics

Four different formulations were used in this example: 160 mg amantadine HCl syrup (50 mg of amantadine HCl/5 ml, administered 16 ml), in immediate release form; and Amantadine ER 160, 240, 320 mg tablets, manufactured as described in Example 1.

5.1 Absorption, Distribution, and Elimination
Absorption
Following oral administration of Amantadine ER, the peak concentration of amantadine was observed in a median time of 7.5 hours (range 5.5 to 12 hours). After a single oral administration of the Amantadine ER 160 mg tablet (129 mg dose in terms of amantadine freebase), the mean (CV %) Cmax and AUC were 328 ng/ml (18%) and 8263 ng him' (18%) respectively. Cmax and AUC with other dose levels of Amantadine ER increase proportionally.
Effect of Food
Food does not affect the rate or the extent of absorption of Amantadine ER.
Distribution
Amantadine is 67% bound to plasma proteins over a concentration range of 0.1 to 2.0 µg/mL. The volume of distribution after intravenous administration is 3-8 L/kg, suggesting potential extravascular distribution.
Elimination
Amantadine is mainly eliminated renally, and approximately 85% of the administered dose is excreted unchanged in urine. After oral administration of a single Amantadine ER 160 mg tablet (129 mg dose in terms of amantadine free base), the apparent oral clearance was approximately 11 L/h. The half-life was approximately 16 hours. Coadministration of quinine or quinidine with amantadine was shown to reduce the renal clearance of amantadine by about 30%.
Metabolism
Metabolism accounts for only 5-15% of the total clearance for amantadine. Eight metabolites of amantadine have been identified in human urine. One metabolite, an N-acetylated compound, was quantified in human urine and accounted for 0-15% of the administered dose in multiple studies. The contribution of this metabolite to efficacy or toxicity is not known.
Excretion
Amantadine is primarily excreted by glomerular filtration and tubular secretion. The pH of the urine has been reported to influence the excretion rate of amantadine.

5.2 Steady State Pharmacokinetic Simulations

Figure 17:
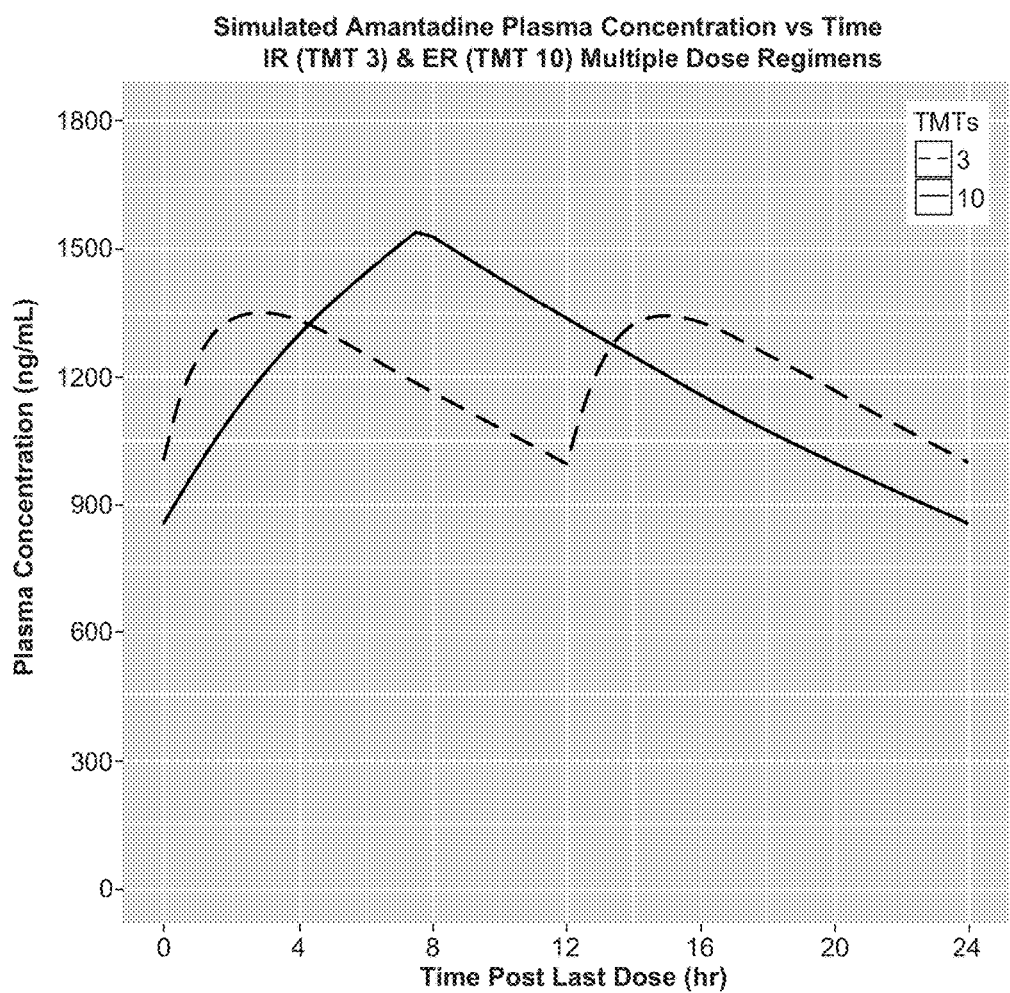
FIG. 17 depicts the simulated amantadine plasma concentration-time profiles over a period of 24 hours following administration of 200 mg amantadine in an immediate release formulation twice a day (TMT 3) and 400 mg amantadine ((160 mg tablet+240 tablet administered simultaneously) in a sustained release formulation once a day (TMT 10).

Using the formulations described above, the amantadine plasma concentration over a period of 24 hours was simulated using the pharmacokinetic software, NONMEM 7, PDx-POP 5.2 following the administration of either 200 mg amantadine in an immediate release formulation b.i.d. (twice per day) or 400 mg amantadine in a sustained release formulation q.d. (160 mg tablet+240 tablet administered simultaneously, once per day). As shown in FIG. 17, the initial slope of the dC/dT for the sustained release formulation is less than the slope determined for the immediate release formulation. As shown in FIG. 17 and Table 10, the sustained release formulation exhibits slightly higher plasma concentration peaks and longer $T_{max}$ and $T_{last}$ compared with the immediate release formulation. In addition, the sustained release formulation indicates higher exposures ($AUC_{0-t}$) compared with the immediate release formulation.

TABLE 10

Amantadine steady state pharmacokinetic parameters

| TMT | Dose Regimen | $C_{max}$ ng/mL | $T_{max}$ h | $T_{last}$ h | $C_{last}$ ng/mL | $AUC_{0-\tau}$ h ng/mL | cav ng/mL |
|---|---|---|---|---|---|---|---|
| ER | 160 mg + 240 mg q24h | 1532 | 7.5 | 24 | 857 | 28838 | 1202 |
| IR | 200 mg q12h | 1342 | 3 | 12 | 1002 | 14413 | 1201 |

Example 6

Pharmacokinetics in Special Populations 6.1 Effect of Age
The apparent oral plasma clearance of amantadine is reduced, and the plasma half-life and plasma concentrations are increased in healthy elderly individuals age 60 and older. After single dose administration of 25 to 75 mg to 7 healthy, elderly male volunteers, the apparent plasma clearance of amantadine was 0.10±0.04 L/h/kg (range 0.06 to 0.17 L/h/kg) and the half-life was 29±7 hours (range 20 to 41 hours). Whether these changes are due to decline in renal function or other age related factors is not known.

In clinical studies with Amantadine ER tablets, patients 65 to 85 years of age on average had higher plasma amantadine concentrations than younger patients.

6.2 Effect of Gender

In a study of young healthy subjects (n=20), mean renal clearance of amantadine, normalized for body mass index, was 1.5 fold higher in males compared to females (p<0.032).

6.3 Effect of Renal Impairment

Compared with otherwise healthy adult individuals, the clearance of amantadine is significantly reduced in adult patients with renal insufficiency. The elimination half-life increases two to three fold or greater when creatinine clearance is less than 40 mL/min/1.73 m$^2$ and averages eight days in patients on chronic maintenance hemodialysis. Amantadine is removed in negligible amounts by hemodialysis.

Renal Impairment—Amantadine ER

A summary of plasma $C_{max}$, $T_{max}$, $AUC_{0-\infty}$, terminal elimination half-life (T-half), apparent clearance (CL/F), and apparent volume of distribution (Vd/F) following a single 160-mg dose of Amantadine ER in subjects with normal renal function compared with subjects with moderate and severe renal impairment is provided in Table 11.

for change in renal function, especially in those with severe renal impairment receiving the maximum daily dosage of 322 mg.

Example 7

Clinical Studies: Primary and Secondary Efficacy Analysis

Amantadine HCl ER Tablets as described in Example 1 were used in Phase 3 clinical studies.

7.1 Overview

Two randomized, double-blind, placebo-controlled Phase 3 studies (Study A and Study B) evaluated the efficacy and safety of Amantadine HCl ER Tablets at dosages of 240 mg/day and 320 mg/day for the treatment of Parkinson's disease (PD) patients with LID.

7.2 Study Designs—Phase 3 Clinical Studies

Study A

Study A was a Phase 3, randomized, double-blind, placebo-controlled, parallel-group, 3-arm, multicenter study. This was a fixed-dose trial (after a Titration Period) that compared the efficacy and safety of Amantadine HCl ER

TABLE 11

Summary of Amantadine ER Pharmacokinetic Parameters in Patients with Renal Impairment and Control Subjects with Normal Renal Function

| Renal Function | | $C_{max}$ (ng/mL) Mean (% CV) | $T_{max}$ (h) Median (range) | $AUC_{(0-0-\infty)}$ (ng · h/mL) Mean (% CV) | T-half (h) Mean (% CV) | CL/F (L/h) Mean (% CV) | Vd/F (L) Mean (% CV) |
|---|---|---|---|---|---|---|---|
| Moderate Impairment[1] eGFR 30-59 mL/min/ 1.73 m$^2$ | N | 8 380.0 (21.4) | 8 11.5 (9.0-24.0) | 8 33066.1 (31.6) | 8 47.2 (31.4) | 8 5.5 (45.2) | 8 344.8 (26.5) |
| Severe Impairment[1] eGFR <30 mL/min/ 1.73 m$^2$ | N | 8 344.9 (22.8) | 8 11.0 (6.0-14.0) | 8 39031.7 (39.9) | 8 116.3 (46.6) | 8 4.6 (29.9) | 8 799.8 (68.8) |
| Normal[2] CrCl >89 mL/min | N | 8 281.3 (26.4) | 8 11.0 (8.0-12.2) | 8 10108.7 (26.9) | 8 18.5 (13.2) | 8 17.4 (40.3) | 8 448.2 (27.3) |

[1]eGFR estimated by the Modification of Diet in Renal Disease equation
[2]CrCl estimated by the Cockcroft-Gault equation The mean renal amantadine clearance was 11 L/h (% CV 41.3), 3.5 L/h (% CV 47.0), and 2.6 L/h (% CV 34.5) in subjects with normal renal function, moderate, and severe renal impairment, respectively.

Dosing in Patients with Renal Impairment

There are no modifications for the recommended initial and maximum dosage in patients with renal impairment; however, modifications are contemplated for the titration interval and frequency of dosing in patients with moderate and severe renal impairment. Renal Function is estimated by Modification of Diet in Renal Disease (MDRD) method, expressed as Estimated GFR (mL/min/1.73 m$^2$). For Mild renal impairment (60 to 89), the minimum titration interval is to increase every week and frequency of dosing regimen is one dose every 24 hours. For Moderate renal impairment (30 to 59), the minimum titration interval is to increase every 3 weeks and frequency of dosing regimen is one dose every 48 hours. For Severe renal impairment (15 to 29), the minimum titration interval is to increase every 4 weeks and frequency of dosing regimen is one dose every 96 hours. For End-Stage renal impairment (below 15), minimum titration interval and frequency of dosing regimen is contraindicated. It is recommended to monitor patients with renal impairment tablets with placebo in subjects 30 to 85 years of age with PD who had LID. Subjects diagnosed with secondary PD or had a history of pallidotomy or other ablative surgery for treatment of PD, or had been implanted with a uni- or bilateral deep brain stimulator, were excluded from participation in the study.

Eligible subjects were randomized in a 1:1:1 manner into one of three treatment groups: Amantadine HCl ER 320 mg, Amantadine HCl ER 240 mg, or Placebo.

Subjects assigned to the Amantadine HCl ER 320 mg group underwent a 2-week dose titration beginning with a 160 mg QD dose for 1 week, then a 240 mg QD dose for 1 week, and then a 320 mg QD dose for 12 weeks followed by a dose-taper for 2 weeks. Subjects assigned to the Amantadine HCl ER 240 mg group underwent a 2-week dose titration beginning with placebo QD dose for 1 week, then a 160 mg QD dose for 1 week, and then a 240 mg QD dose for 12 weeks followed by a dose-taper for 2 weeks. Subjects assigned to the Placebo group took placebo tablets QD for 16 weeks.

Study B

Study B was a Phase 3, randomized, double-blind, placebo-controlled, parallel-group, 3-arm, multicenter study. This was a fixed-dose trial (after a Titration Period) that compared the efficacy and safety of Amantadine HCl ER tablets with placebo in subjects 30 to 85 years of age with PD who had LID. Subjects diagnosed with secondary PD or had a history of pallidotomy or other ablative surgery for treatment of PD, or had been implanted with a uni- or bilateral deep brain stimulator were excluded from participation.

Eligible subjects were randomized in a 1:1:1 manner into one of three treatment groups: Amantadine HCl ER 320 mg, amantadine HCl ER 240 mg, or Placebo.

Subjects assigned to the Amantadine HCl ER 320 mg group underwent a 2-week dose titration beginning with a 160 mg QD (every day) dose for 1 week, then a 240 mg QD dose for 1 week, and then a 320 mg QD dose for 22 weeks followed by a dose-taper for 2 weeks. Subjects assigned to the Amantadine HCl ER 240 mg group underwent a 2-week dose titration beginning with placebo QD dose for 1 week, then a 160 mg QD dose for 1 week, and then a 240 mg QD dose for 22 weeks followed by a dose-taper for 2 weeks. Subjects assigned to the Placebo group took placebo tablets QD for 26 weeks.

Study A and Study B were almost identical; the primary difference between the two studies was the duration of treatment. The duration of treatment was 16 and 26 weeks for Study A and Study B, respectively.

Unified Dyskinesia Rating Scale (UDysRS)

Overview: The Unified Dyskinesia Rating Scale (UDysRS) is developed to evaluate involuntary movements often associated with treating Parkinson's disease. There are two primary sections:

On-Dyskinesia refers to the choreic and dystonic movements described to the patient as "jerking or twisting movements that occur when your medicine is working."

Off-Dystonia were described to the patient as "spasms or cramps that can be painful and occur when your Parkinson's disease medications are not taken or are not working."

7.3 Efficacy Results—Pooled Analysis of Phase 3 Studies (Study A and Study B)

Table 12 summarizes subject disposition for the Phase 3 Study Population. The Phase 3 Study Population included subjects from the two Phase 3 studies (Study A and Study B).

TABLE 12

Subject Disposition by Treatment Group - Study A and Study B - Phase 3 Study Population

| | Amantadine HCl ER 320 mg n (%) | Amantadine HCl ER 240 mg n (%) | Placebo n (%) | All Subjects Combined n (%) |
|---|---|---|---|---|
| Screened | | | | 348 |
| Randomized Population | 75 | 75 | 72 | 222 |
| ITT Population | 75 (100.0) | 75 (100.0) | 72 (100.0) | 222 (100.0) |
| Completed the Study | 46 (61.3) | 44 (58.7) | 43 (59.7) | 133 (59.9) |
| Discontinued Study by Reason | 29 (38.7) | 31 (41.3) | 29 (40.3) | 89 (40.1) |
| Adverse Event | 13 (17.3) | 8 (10.7) | 6 (8.3) | 27 (12.2) |
| Lack of Efficacy | 0 (0.0) | 0 (0.0) | 1 (1.4) | 1 (0.5) |
| Lost to Follow-up | 0 (0.0) | 0 (0.0) | 1 (1.4) | 1 (0.5) |
| Non-Compliance with Study Drug | 0 (0.0) | 0 (0.0) | 1 (1.4) | 1 (0.5) |
| Physician Decision | 0 (0.0) | 2 (2.7) | 1 (1.4) | 3 (1.4) |
| Protocol Violation | 1 (1.3) | 2 (2.7) | 1 (1.4) | 4 (1.8) |
| Trial Screen Failure* | 0 (0.0) | 0 (0.0) | 1 (1.4) | 1 (0.5) |
| Study Terminated by Sponsor | 8 (10.7) | 11 (14.7) | 8 (11.1) | 27 (12.2) |
| Withdrawal by Subject | 6 (8.0) | 8 (10.7) | 8 (11.1) | 22 (9.9) |
| Other | 1 (1.3) | 0 (0.0) | 1 (1.4) | 2 (0.9) |

The denominator for calculating percentagesis the number of subjects in the Randomized Population.

*Subject 002-003 was randomized to study A in error with high serum creatinine levels. As the subject neared completion of the study, the high serum creatinine levels were noted and the investigator removed the subject from the study on Study Day 139 with the reason for discontinuation recorded as "trial screen failure".

ER = extended-release; ITT = Intention-to-Treat.

Table 13 presents the results for mean change in Total UDysRS score from baseline to Day 98 (Visit 7) using stable dose LOCF for the Phase 3 Intent To Treat ("ITT") Population. The mean reduction from baseline to Day 98 using stable dose LOCF was 13.5 for the Amantadine HCl ER 320 mg group, 16.5 for the Amantadine HCl ER 240 mg group, and 9.3 for the Placebo group.

TABLE 13

Mean Change in Total UDysRS Score from Baseline to Day 98 Using Stable Dose LOCF - Study A and Study B - Phase 3 ITT Population

| Visit Statistic | Amantadine HCl ER 320 mg (N = 75) | Amantadine HCl ER 240 mg (N = 75) | Placebo (N = 72) |
|---|---|---|---|
| Visit 2 (Baseline) | | | |
| n | 74 | 74 | 72 |
| Mean (SD) | 37.4 (12.21) | 43.3 (13.74) | 39.9 (12.94) |
| Visit 7 (Day 98)/ Stable Dose LOCF [1] | | | |
| n | 66 | 66 | 62 |
| Mean (SD) | 24.0 (13.03) | 26.9 (15.89) | 30.3 (13.19) |
| Change from Baseline (SD) | −13.5 (11.88) | −16.5 (15.86) | −9.3 (12.39) |

The analysis visit window for Day 98 (Visit 7) for the primary endpoint used stable dose last observation carried forward (last data point collected after Day 39 and before Day 102). n is the number of subjects with values at each time point.
ER = extended-release; LOCF = last observation carried forward; SD = standard deviation; UDysRS = Unified Dyskinesia Rating Scale.

Table 14 presents the treatment comparisons of the Amantadine HCl ER 320 mg group and the Amantadine HCl ER 240 mg group with placebo for mean change in Total UDysRS score from baseline to Day 98 using stable dose LOCF for the Phase 3 ITT Population. Treatment with Amantadine HCl ER 320 mg resulted in a significantly larger reduction in Total UDysRS score than placebo (−5.2; p=0.017). Treatment with Amantadine HCl ER 240 mg also resulted in a significantly larger reduction in Total UDysRS score than placebo (−5.5; p=0.012).

TABLE 14

Analysis of Mean Change in Total UDysRS Score from Baseline to Day 98 Using Stable Dose LOCF - Studies A and B - Phase 3 ITT Population

| Treatment Group | LS Mean (SE) | Treatment Difference (Amantadine HCl ER vs. Placebo) | | |
|---|---|---|---|---|
| | | Difference | 95% CI of Difference | P-value |
| Amantadine HCl ER 320 mg | −14.7 (1.51) | −5.2 | (−9.5, −0.9) | 0.017 |
| Amantadine HCl ER 240 mg | −15.1 (1.52) | −5.5 | (−9.8, −1.2) | 0.012 |
| Placebo | −9.5 (1.55) | | | |

Secondary Efficacy Analysis - Change in the Number of Awake "ON" Hours Without Troublesome Dyskinesias from Baseline to Day 98 Using Stable Dose LOCF Table 15 presents the results for mean change in number of awake "ON" hours without troublesome dyskinesia (without dyskinesia and with non-troublesome dyskinesia) from baseline to Day 98 using stable dose LOCF for the Phase 3 ITT Population.

The mean increase from baseline to Day 98 using stable dose LOCF was 3.7 hours for the Amantadine HCl ER 320 mg group, 2.3 hours for the Amantadine HCl ER 240 mg group, and 1.5 hours for the Placebo group.

TABLE 15

Mean Change in Number of Awake "ON" Hours Without Troublesome Dyskinesias from Baseline to Day 98 Using Stable Dose LOCF - Study A and Study B - Phase 3 ITT Population

| Visit Statistic | Amantadine HCl ER 320 mg | Amantadine HCl ER 240 mg | Placebo |
|---|---|---|---|
| Visit 2 (Baseline) | | | |
| n | 72 | 72 | 62 |
| Mean (SD) | 9.7 (3.48) | 10.0 (3.73) | 9.5 (3.51) |
| Visit 7 (Day 98)/Stable Dose LOCF [1] | | | |
| n | 75 | 75 | 72 |
| Mean (SD) | 13.5 (4.50) | 12.2 (4.04) | 11.3 (3.66) |
| Change from Baseline (SD) | 3.7 (4.40) | 2.3 (3.47) | 1.5 (3.49) |

The analysis visit window for Day 98 (Visit 7) for the secondary endpoint used stable dose last observation carried forward (last data point collected after Day 39 and before Day 102).
n is the number of subjects with values at each time point.

Table 16 presents the treatment comparisons of the Amantadine HCl ER 320 mg group and the Amantadine HCl ER 240 mg group with placebo for mean change in number of awake "ON" hours without troublesome dyskinesia from baseline to Day 98 using stable dose LOCF for the Phase 3 ITT Population.

Treatment with Amantadine HCl ER 320 mg resulted in a significantly larger increase in number of awake "ON" hours without troublesome dyskinesia than placebo (2.3 hours; p<0.001). The treatment comparison of Amantadine HCl ER 240 mg with placebo was not statistically significant (p=0.119).

TABLE 16

Analysis of Mean Change in Number of Awake "ON" Hours Without Troublesome Dyskinesias from Baseline to Day 98 Using Stable Dose LOCF - Study A and Study B - Phase 3 ITT Population

| Treatment Group | LS Mean (SE) | Treatment Difference (Amantadine HCl ER vs. Placebo) | | |
|---|---|---|---|---|
| | | Difference | 95% CI of Difference | P-value |
| Amantadine HCl ER 320 mg | 3.67 (0.42) | 2.3 | (1.1, 3.5) | <0.001 |
| Amantadine HCl ER 240 mg | 2.36 (0.42) | 1.0 | (−0.3, 2.2) | 0.119 |
| Placebo | 1.39 (0.45) | | | |

7.5.5 Exploratory Efficacy Analyses

7.5.5.1 Change in the Number of Awake "OFF" Hours from Baseline to Day 98 Using Stable Dose LOCF Table 17 presents the results for mean change in number of awake "OFF" hours from baseline to Day 98 using stable dose LOCF for the Phase 3 ITT Population. The changes in awake "OFF" hours over time for all treatment groups were small with no meaningful trends observed.

TABLE 17

Number of Awake "OFF" Hours from Baseline to Day 98 Using Stable Dose LOCF - Study A and Study B - Phase 3 ITT Population

| Visit Statistic | Amantadine HCl ER 320 mg | Amantadine HCl ER 240 mg | Placebo |
|---|---|---|---|
| Visit 2 (Baseline) | | | |
| n | 68 | 68 | 58 |
| Mean (SD) | 3.7 (2.45) | 3.4 (2.03) | 4.2 (2.11) |
| Visit 7 (Day 98)/Stable Dose LOCF [1] | | | |
| n | 72 | 74 | 69 |
| Mean (SD) | 3.4 (2.45) | 3.6 (2.36) | 3.7 (2.05) |
| Change from Baseline (SD) | −0.3 (2.12) | 0.3 (2.34) | −0.3 (2.25) |

The analysis visit window for Day 98 (Visit 7) for the primary endpoint used stable dose last observation carried forward (last data point collected after Day 39 and before Day 102).
n is the number of subjects with values at each time point.

Table 18 presents the treatment comparisons of the Amantadine HCl ER 320 mg group and the Amantadine HCl ER 240 mg group with placebo for mean change in number of awake "OFF" hours from baseline to Day 98 using stable dose LOCF for the Phase 3 ITT Population. No statistically significant treatment differences were observed.

TABLE 18

Analysis of Mean Change in Number of Awake "OFF" Hours from Baseline to Day 98 Using Stable Dose LOCF - Study A and Study B - Phase 3 ITT Population

| Treatment Group | LS Mean (SE) | Treatment Difference (Amantadine HCl ER vs. Placebo) | | |
|---|---|---|---|---|
| | | Difference | 95% CI of Difference | P-value |
| Amantadine HCl ER 320 mg | −0.29 (0.244) | −0.26 | (−0.97, 0.45) | 0.472 |

TABLE 18-continued

Analysis of Mean Change in Number of Awake "OFF"
Hours from Baseline to Day 98 Using Stable Dose
LOCF - Study A and Study B - Phase 3 ITT Population

| Treatment Group | LS Mean (SE) | Treatment Difference (Amantadine HCl ER vs. Placebo) | | |
|---|---|---|---|---|
| | | Difference | 95% CI of Difference | P-value |
| Amantadine HCl ER 240 mg | 0.12 (0.245) | 0.15 | (−0.57, 0.87) | 0.680 |
| Placebo | −0.03 (0.266) | | | |

7.5.5.2 Change in the Sum of MDS-UPDRS Parts II and III from Baseline to Day 98 Using Stable Dose LOCF The MDS-UPDRS is a validated scale used to evaluate different neurological aspects of parkinsonian subjects and is composed of 4 parts: Part I (non-motor experiences of daily living), Part II (motor experiences of daily living), Part III (motor examination) and Part IV (motor complications). The MDS-UPDRS Parts II and III were completed at screening (Visit 1), at baseline (Visit 2), at the end of the Titration Period (Visit 4), during the Maintenance Period (Visits 5, 6, and 7) or at the Premature Termination Visit.

The MDS-UPDRS Part II score and the MDS-UPDRS Part III score were derived. The MDS-UPDRS Part II score was calculated as the sum of the individual scores for Part II (score range is from 0 to 52). The MDS-UPDRS Part III score was calculated as the sum of the 33 individual scores for Part III (score range is from 0 to 132).

For the integrated/pooled analysis, the change from baseline in the sum of MDS-UPDRS Part II and Part III score was analyzed at Day 98 (Visit 7).

Table 19 presents the results for mean change in the sum of MDS-UPDRS Parts II and III from baseline to Day 98 using stable dose LOCF for the Phase 3 ITT Population. The mean change in the sum of MDS-UPDRS Parts II and III was −4.3 for the Amantadine HCl ER 320 mg group, −5.9 for the Amantadine HCl ER 240 mg group, and −8.3 for the Placebo group.

TABLE 19

Mean Change in the Sum of MDS-UPDRS Parts II
98 Using Stable Dose and III from Baseline to Day
LOCF - Study A and Study B - Phase 3 ITT Population

| Visit Statistic | Amantadine HCl ER 320 mg | Amantadine HCl ER 240 mg | Placebo |
|---|---|---|---|
| Visit 2 (Baseline) | | | |
| n | 75 | 75 | 72 |
| Mean (SD) | 37.3 (17.91) | 42.3 (19.52) | 42.3 (19.75) |
| Visit 7 (Day 98)/ Stable Dose LOCF [1] | | | |
| n | 67 | 66 | 62 |
| Mean (SD) | 34.4 (17.01) | 37.3 (18.74) | 34.1 (17.85) |
| Change from Baseline (SD) | −4.3 (13.65) | −5.9 (14.76) | −8.3 (14.61) |

The analysis visit window for Day 98 (Visit 7) for the primary endpoint used stable dose last observation carried forward (last data point collected after Day 39 and before Day 102) n is the number of subjects with values at each time point.

Table 20 presents the treatment comparisons of the Amantadine HCl ER 320 mg group and the Amantadine HCl ER 240 mg group with placebo for mean change in the sum of MDS-UPDRS Parts II and III from baseline to Day 98 using stable dose LOCF for the Phase 3 ITT Population. No statistically significant treatment differences were observed.

TABLE 20

Analysis of Mean Change in the Sum of MDS-UPDRS
Parts II and III from Baseline to Day 98 Using Stable Dose
LOCF - Study A and Study B - Phase 3 ITT Population

| Treatment Group | LS Mean (SE) | Treatment Difference (Amantadine HCl ER vs. Placebo) | | |
|---|---|---|---|---|
| | | Difference | 95% CI of Difference | P-value |
| Amantadine HCl ER 320 mg | −5.3 (1.56) | 2.7 | (−1.8, 7.1) | 0.235 |
| Amantadine HCl ER 240 mg | −5.3 (1.57) | 2.7 | (−1.8, 7.1) | 0.237 |
| Placebo | −7.9 (1.62) | | | |

7.5.5.3 Change in Total UDysRS Score from Baseline to Day 42 and Day 70

Table 21 presents the results for mean change in Total UDysRS score from baseline to Day 42 and Day 70 for the Phase 3 ITT Population. From baseline to Day 42 and Day 70, respectively, the mean reduction in the Total UDysRS score was 14.0 and 14.8 for the Amantadine HCl ER 320 mg group, 16.9 and 17.5 for the Amantadine HCl ER 240 mg group, and 8.2 and 9.9 for the Placebo group. At both time points, there were larger reductions in the Total UDysRS score in the Amantadine HCl ER 320 mg and Amantadine HCl ER 240 mg groups compared with placebo.

TABLE 21

Mean Change in Total UDysRS Score from Baseline to
Day 42 and Day 70 - Study A and Study B - Phase 3 ITT Population

| Visit Statistic | Amantadine HCl ER 320 mg | Amantadine HCl ER 240 mg | Placebo |
|---|---|---|---|
| Visit 2 (Baseline) | | | |
| n | 74 | 74 | 72 |
| Mean (SD) | 37.4 (12.21) | 43.3 (13.74) | 39.9 (12.94) |
| Visit 5 (Day 42) | | | |
| n | 63 | 69 | 60 |
| Mean (SD) | 24.2 (13.01) | 26.9 (14.16) | 30.3 (13.39) |
| Change from Baseline (SD) | −14.0 (11.03) | −16.9 (14.59) | −8.2 (11.25) |
| Visit 6 (Day 70) | | | |
| n | 58 | 55 | 54 |
| Mean (SD) | 22.4 (12.58) | 25.6 (14.12) | 28.9 (14.16) |
| Change from Baseline (SD) | −14.8 (11.27) | −17.5 (14.45) | −9.9 (12.23) | n is the number of subjects with values at each time point.

Table 22 presents the treatment comparisons of the Amantadine HCl ER 320 mg group and the Amantadine HCl ER 240 mg group with placebo for mean change in Total UDysRS score from baseline to Day 42 and Day 70 for the ITT Population.

Treatment with Amantadine HCl ER 320 mg and 240 mg both resulted in a significantly larger reduction in Total UDysRS score than placebo from baseline to Day 42 and Day 70.

TABLE 22

Analysis of Mean Change in Total UDysRS Score from Baseline to
Day 42 and Day 70 - Study A and Study B - Phase 3 ITT Population

| Visit (Day) | Treatment Group | N | LS Mean (SE) | Treatment Difference (Amantadine HCl ER vs. Placebo) | | P-value versus Placebo |
|---|---|---|---|---|---|---|
| | | | | Difference | 95% CI of Difference | |
| Visit 5 (Day 42) | Amantadine HCl ER 320 mg | 63 | −15.0 (1.37) | −6.4 | (−10.2, −2.5) | 0.001 |
| | Amantadine HCl ER 240 mg | 69 | −15.3 (1.33) | −6.6 | (−10.5, −2.8) | 0.001 |
| | Placebo | 60 | −8.6(1.39) | | | |
| Visit 6 (Day 70) | Amantadine HCl ER 320 mg | 58 | −16.1 (1.49) | −5.8 | (−10.0, −1.6) | 0.007 |
| | Amantadine HCl ER 240 mg | 55 | −16.2 (1.50) | −5.9 | (−10.1, −1.6) | 0.007 |
| | Placebo | 54 | −10.3 (1.53) | | | |

A mixed effect repeated measure analysis was performed on change from baseline values with treatment group, visit, and treatment group-by-visit interaction as fixed effects, patient as a random effect and baseline score as a covariate.

Overall Conclusions

The pooled results from two Phase 3 randomized, double-blind, placebo-controlled studies designed to evaluate the efficacy and safety of Amantadine HCl ER Tablets with placebo in subjects with PD who had LID were analyzed. The primary efficacy endpoint in these studies was the change from baseline to Day 98 in the Total UDysRS score. The pooled analysis of these Phase 3 studies demonstrated that Amantadine HCl ER tablets, at both 320 mg and 240 mg administered once daily in the morning, improved dyskinesia in PD subjects with LID as determined by statistically significant and clinically meaningful reductions in Total UDysRS scores.

The Phase 3 studies enrolled male and female subjects 30 to 85 years of age who had been diagnosed with idiopathic PD who had levodopa-induced predictable peak-effect dyskinesia considered by the subject to be problematic and/or disabling. UDysRS and MDS-UPDRS were administered within 3 hours of the last dose of levodopa to allow for consistent assessment of peak dose dyskinesia. The two Phase 3 studies randomized 222 subjects: 75 subjects were randomized to Amantadine HCl ER 320 mg, 75 subjects to Amantadine HCl ER 240 mg, and 72 subjects to placebo. One hundred thirty-three subjects completed the respective studies.

Subjects recruited for the Phase 3 studies were typical of a population with PD who had LID. To enter the studies all subjects were required to be currently treated with levodopa. The baseline mean dose of levodopa was 735 mg. For all subjects, the mean baseline Total UDysRS score was 40. Across all treatment groups, the mean Hoehn & Yahr Stage was 2.

The primary analysis window was Day 98 (Visit 7) using stable dose LOCF, which included the last data point collected after Day 39 and before Day 102. The LS mean reduction in Total UDysRS score was 14.7 for the Amantadine HCl ER 320 mg group, 15.1 for the Amantadine HCl ER 240 mg group, and 9.5 for the Placebo group. From baseline to Day 98 with stable dose LOCF, treatment with Amantadine HCl ER 320 mg resulted in a significantly larger reduction in Total UDysRS score than placebo (−5.2; p=0.017). Treatment with Amantadine HCl ER 240 mg also resulted in a significantly larger reduction in Total UDysRS score than placebo (−5.5; p=0.012) from baseline to Day 98 with stable dose LOCF.

A key secondary endpoint in the Phase 3 trials was the change in the number of awake "ON" hours without troublesome dyskinesia from baseline to Day 98 using stable dose LOCF. Treatment with Amantadine HCl ER 320 mg resulted in a larger increase in the number of awake "ON" hours without troublesome dyskinesia than placebo (2.3 hours; p<0.001). Treatment with Amantadine HCl ER 240 mg resulted in a mean increase in the number of awake "ON" hours without troublesome dyskinesia, however, the treatment difference was not statistically significant compared with placebo (1.0 hours; p=0.119).

MDS-UPDRS Part II and III was used to assess any potential worsening of PD symptoms during the study. There was little change in the sum of MDS-UPDRS Parts II and III compared with placebo at both dose levels of Amantadine HCl ER, which suggests that treatment with Amantadine HCl ER did not worsen PD symptoms.

In the analysis of the primary and secondary efficacy parameters by subgroups, there were larger mean reductions in Total UDysRS score observed in subjects who had more severe LID (baseline Total UDysRS scores >median) compared to subjects with less severe LID (baseline Total UDysRS scores median). There were larger mean reductions in Total UDysRS observed in the subgroup of subjects enrolled outside the US compared to those subjects enrolled at sites in the US. There were no noteworthy trends in mean change in Total UDysRS scores or in mean change in awake "ON" hours without troublesome dyskinesia from baseline to Day 98 using stable dose LOCF based on subpopulations of age, race, gender, or baseline levodopa dose categories median vs. >median dose).

In the pooled efficacy analysis from Study A and Study B, treatment with Amantadine HCl
ER 320-mg and 240-mg tablets for 12 weeks was effective in improving dyskinesia in PD subjects with LID as measured by objective and subjective measures. Both doses produced statistically significant reductions in Total UDysRS score, and Amantadine HCl ER 320 mg was associated with a statistically significant increase in awake "ON" hours without troublesome dyskinesia.

Example 8

Safety

The safety of Amantadine ER tablets, prepared according to Example 1, was evaluated in two placebo-controlled clinical studies in the U.S., Canada, and Europe. Adverse events were consistent and no new or unexpected safety issues were reported. Throughout the study, the most frequently reported Treatment-emergent adverse events (TE-AEs) by preferred term were hallucinations (8.1%), increased dyskinesia (8.1%), fall (7.2%), nausea (7.2%), dry mouth (5.4%), peripheral edema (5.0%), urinary tract infection (5.0%), and somnolence (5.0%).

Example 9

Clinical Trials on Patients with Drug-Induced Extrapyramidal Reactions

A clinical trial on the effects of amantadine on drug-induced extrapyramidal reactions is conducted. Inclusion criteria include patients, both male and female, who are 18 years old of age and older and who suffer from drug-induced extrapyramidal reactions. The patients exhibit at least one of the following symptoms: dystonia (continuous spasms and muscle contractions), akathisia (motor restlessness), parkinsonism (characteristic symptoms such as rigidity), bradykinesia (slowness of movement), tremor, and tardive dyskinesia (irregular, jerky movements).

Studies are conducted to evaluate the efficacy and safety of Amantadine HCl ER Tablets at dosages of 160 mg/day, 240 mg/day and 320 mg/day for the treatment of patients with drug-induced extrapyramidal reactions.

Study C and D

These two studies are two fixed-dose trials (after a Titration Period) that compare the efficacy and safety of Amantadine HCl ER tablets with placebo in subjects 18 to 85 years of age with drug-induced extrapyramidal reactions. Eligible subjects are randomized in a 1:1:1:1 manner into one of four treatment groups: Amantadine HCl ER 320 mg, Amantadine HCl ER 240 mg, Amantadine HCl ER 160 mg, or Placebo.

Subjects assigned to the Amantadine HCl ER 320 mg group undergo a 2-week dose titration beginning with a 160 mg QD dose for 1 week, then a 240 mg QD dose for 1 week, and then a 320 mg QD dose for 12 weeks or 22 weeks followed by a dose-taper for 2 weeks. Subjects assigned to the Amantadine HCl ER 240 mg group undergo a 2-week dose titration beginning with placebo QD dose for 1 week, then a 160 mg QD dose for 1 week, and then a 240 mg QD dose for 12 weeks or 22 weeks followed by a dose-taper for 2 weeks. Subjects assigned to the Amantadine HCl ER 160 mg group begin with placebo QD dose for 1 week, and then a 160 mg QD dose for 15 weeks or 25 weeks. Subjects assigned to the Placebo group take placebo tablets QD for 16 weeks or 26 weeks.

During the Titration Period, patients randomized to the Amantadine ER 240 mg treatment group receive placebo daily for one week, then Amantadine ER 160 mg daily for one week, before increasing to the 240 mg once daily maintenance dose. Patients in the Amantadine ER 320 mg treatment group receive Amantadine ER 160 mg daily for one week, then Amantadine ER 240 mg daily for one week, before increasing to the 320 mg once daily maintenance dose. The 2-week dose controlled Taper Period follows the 12-week and 26-week Maintenance Periods, respectively. During the Taper Period, patients receiving Amantadine ER 240 mg daily are withdrawn from study medication by receiving Amantadine ER 160 mg daily for 1 week, then placebo for 1 week. Patients receiving Amantadine ER 320 mg daily are withdrawn from study medication by receiving Amantadine ER 240 mg daily for 1 week, then Amantadine ER 160 mg for 1 week.

Study C and Study D are almost identical; the primary difference between the two studies is the duration of treatment. The duration of treatment is 16 and 26 weeks for Study C and Study D, respectively.

For efficacy assessments, the patients are assessed with the following rating scales that are commonly used to assess the severity of movement disorders: Simpson-Angus Scale (SAS), Barnes Akathisia Rating Scale (BARS), Abnormal Involuntary Movement Scale (AIMS), and Extrapyramidal Symptom Rating Scale (ESRS).

What is claimed is:

1. A method of treating a drug-induced extrapyramidal reaction in an adult patient, comprising:
   i) administering to the patient once daily in the morning a pharmaceutical composition comprising about 129 mg of amantadine free base equivalent for one week;
   ii) increasing the dose of amantadine by administering to the patient once daily in the morning a pharmaceutical composition comprising about 193 mg of amantadine free base equivalent;
   wherein each of the pharmaceutical compositions comprises i) an extended release component comprising amantadine free base equivalent; and ii) an immediate release component comprising about 48 mg of amantadine free base equivalent, wherein each of the pharmaceutical compositions is an osmotic device comprising an osmotic agent and an osmotic coating,
   wherein the maximum daily dose of amantadine is about 322 mg of amantadine free base equivalent,
   wherein each of the pharmaceutical compositions provides a mean change in amantadine plasma concentration as a function of time (dC/dT) that is between about 40% and about 70% of the dC/dT provided by the same quantity of amantadine or a pharmaceutically acceptable salt thereof in an immediate release form, and
   wherein the dC/dT values are measured in a single dose human pharmacokinetic study over the time period between 0 and 4 hours after administration.

2. A method of treating a drug-induced extrapyramidal reaction in an adult patient, comprising:
   i) administering to the patient once daily in the morning a pharmaceutical composition comprising about 129 mg of amantadine free base equivalent for one week;
   ii) increasing the dose of amantadine by administering to the patient once daily in the morning a pharmaceutical composition comprising about 193 mg of amantadine free base equivalent for one week;
   iii) increasing the dose of amantadine by administering to the patient once daily in the morning a pharmaceutical composition comprising about 258 mg of amantadine free base equivalent;
   wherein each of the pharmaceutical compositions consists of i) an extended release component consisting essentially of amantadine free base equivalent and ii) an immediate release component consisting essentially of about 48 mg of amantadine free base equivalent, wherein each of the pharmaceutical compositions is an osmotic device comprising an osmotic agent and an osmotic coating,
   wherein the maximum daily dose of amantadine is about 322 mg of amantadine free base equivalent,
   wherein each of the pharmaceutical compositions provides a mean change in amantadine plasma concentration as a function of time (dC/dT) that is between about 40% and about 70% of the dC/dT provided by the same quantity of amantadine or a pharmaceutically acceptable salt thereof in an immediate release form, and
   wherein the dC/dT values are measured in a single dose human pharmacokinetic study over the time period between 0 and 4 hours after administration.

3. The method of claim 1, wherein the $T_{max}$ of each pharmaceutical composition after a single-dose administration is between about 5 and about 12 hours.

4. The method of claim 3, wherein the median $T_{max}$ of each pharmaceutical composition after a single-dose administration is about 7.5 hours.

5. The method of claim 2, wherein the mean $C_{max}$ of the pharmaceutical composition comprising about 258 mg of amantadine free base equivalent after a single-dose administration is between about 540 and about 895 ng/ml.

6. The method of claim 1, wherein the mean $C_{max}$ of the pharmaceutical composition comprising about 193 mg of amantadine free base equivalent after a single-dose administration is between about 370 and about 550 ng/ml.

7. The method of claim 1, wherein the mean $C_{max}$ of the pharmaceutical composition comprising about 129 mg of amantadine free base equivalent after a single-dose administration is between about 265 and about 390 ng/ml.

8. The method of claim 2, wherein the mean $AUC_{0-\infty}$ of the pharmaceutical composition comprising about 258 mg of amantadine free base equivalent after a single-dose administration is between about 12,000 and about 26,000 ng·h/mL.

9. The method of claim 1, wherein the mean $AUC_{0-\infty}$ of the pharmaceutical composition comprising about 193 mg of amantadine free base equivalent after a single-dose administration is between about 8,000 and about 20,000 ng·h/mL.

10. The method of claim 1, wherein the mean $AUC_{0-\infty}$ of the pharmaceutical composition comprising about 129 mg of amantadine free base equivalent after a single-dose administration is between about 6,000 and about 12,000 ng·h/mL.

11. The method of claim 1, wherein the drug-induced extrapyramidal reaction is selected from the group consisting of dystonia, akathisia, parkinsonism, bradykinesia, tremor, and tardive dyskinesia, or any combination thereof.

12. The method of claim 1, wherein the drug-induced extrapyramidal reaction is caused by an antipsychotic, antiemetic, antidepressant, or any combination thereof.

13. The method of claim 12, wherein the antipsychotic comprises haloperidol, fluphenazine, thilthixene, trifluoroperazine, acetophenazine, prochlorperazine, perphenazine, loxapine, chlorpromazine, triflupromazine, molindone, mesoridazine, chlorprothixene, thioridazine, clozapine or any combinations thereof.

14. The method of claim 12, wherein the antiemetic comprises metoclopramide, trimethobenzamide or a combination thereof.

15. The method of claim 12, wherein the antidepressant comprises selective serotonin reuptake inhibitors (SSRI), serotonin-norepinephrine reuptake inhibitors (SNRI), norepinephrine-dopamine reuptake inhibitors (NDRI) or any combination thereof.

16. The method of claim 12, wherein the patient continues to receive the antipsychotic, antiemetic, antidepressant, or any combination thereof.

17. The method of claim 1, wherein the relative bioavailability of amantadine or a pharmaceutically acceptable salt thereof is approximately the same under fed and fasting conditions.

18. The method of claim 1, wherein the osmotic devise comprises a semipermeable membrane.

19. The method of claim 18, wherein the osmotic device has an in vitro dissolution profile ranging between about 0.1% to about 50% in about 0.5 hour, about 20% to about 80% in about 2.5 hours, about 40% to about 90% in about 4 hours, and no less than about 85% in about 8 hours, when tested in a USP Type II dissolution apparatus (paddles) in water at about 37° C.

20. The method of claim 19, wherein the osmotic device comprising about 193 mg of amantadine free base equivalent has an in vitro dissolution profile ranging between about 28% to about 48% in about 0.5 hour, about 39% to about 63% in about 2.5 hours, about 61% to about 85% in about 4 hours, and no less than about 85% in about 8 hours.

21. The method of claim 19, wherein the osmotic device comprising about 129 mg of amantadine free base equivalent has an in vitro dissolution profile ranging between about 9% to about 29% in about 0.5 hour, about 37% to about 62% in about 2.5 hours, about 59% to about 83% in about 4 hours, and no less than about 85% in about 8 hours.

22. The method of claim 2, wherein the mean $C_{max}$ of the pharmaceutical composition comprising about 193 mg of amantadine free base equivalent after a single-dose administration is between about 370 and about 550 ng/ml.

23. The method of claim 2, wherein the mean $C_{max}$ of the pharmaceutical composition comprising about 129 mg of amantadine free base equivalent after a single-dose administration is between about 265 and about 390 ng/ml.

24. The method of claim 2, wherein the mean $AUC_{0-\infty}$ of the pharmaceutical composition comprising about 193 mg of amantadine free base equivalent after a single-dose administration is between about 8,000 and about 20,000 ng·h/mL.

25. The method of claim 2, wherein the mean $AUC_{0-\infty}$ of the pharmaceutical composition comprising about 129 mg of amantadine free base equivalent after a single-dose administration is between about 6,000 and about 12,000 ng·h/mL.

26. The method of claim 2, wherein the pharmaceutical composition comprising about 193 mg of amantadine free base equivalent has an in vitro dissolution profile ranging between about 15% to about 35% in about 0.5 hour, about 29% to about 53% in about 2.5 hours, about 53% to about 77% in about 4 hours, and no less than about 85% in about 8 hours as measured in water using a USP type II (paddle) dissolution system at 50 rpm, at a temperature of 37±0.5° C.

27. The method of claim 2, wherein the pharmaceutical composition comprising about 129 mg of amantadine free base equivalent has an in vitro dissolution profile ranging between about 9% to about 29% in about 0.5 hour, about 37% to about 62% in about 2.5 hours, about 59% to about 83% in about 4 hours, and no less than about 85% in about 8 hours as measured in water using a USP type II (paddle) dissolution system at 50 rpm, at a temperature of 37±0.5° C.

28. A method of treating a drug-induced extrapyramidal reaction in an adult patient, comprising:
  i) administering to the patient once daily in the morning a pharmaceutical composition comprising about 129 mg of amantadine free base equivalent, and
  ii) increasing the dose of amantadine in weekly intervals to a maximum daily dose of 322 mg administered once daily in the morning,
  wherein the pharmaceutical composition consists of i) an extended release component consisting essentially of amantadine free base equivalent, and ii) an immediate release component consisting essentially of about 48 mg of amantadine free base equivalent, wherein the pharmaceutical composition is an osmotic device comprising an osmotic agent and an osmotic coating,
  wherein the pharmaceutical composition provides a mean change in amantadine plasma concentration as a function of time (dC/dT) that is between about 40% and about 70% of the dC/dT provided by the same quantity of amantadine or a pharmaceutically acceptable salt thereof in an immediate release form, and
  wherein the dC/dT values are measured in a single dose human pharmacokinetic study over the time period between 0 and 4 hours after administration.

* * * * *

UNITED STATES PATENT AND TRADEMARK OFFICE
CERTIFICATE OF CORRECTION

PATENT NO. : 10,213,394 B1
APPLICATION NO. : 15/898148
DATED : February 26, 2019
INVENTOR(S) : Meyer et al.

It is certified that error appears in the above-identified patent and that said Letters Patent is hereby corrected as shown below:

In the Specification

In Column 5, Line 55, delete "thilthixene," and insert -- thiothixene, --, therefor.

In Column 5, Line 55, delete "trifluoroperazine," and insert -- trifluoperazine, --, therefor.

In Column 9, Line 56, delete "(C1)." and insert -- (Ct). --, therefor.

In Column 10, Line 12, delete "hours" as" and insert -- hours", as --, therefor.

In Column 15, Line 46, delete "patients" and insert -- patient --, therefor.

In Column 16, Line 11, delete "sodium bisulfate," and insert -- sodium bisulfite, --, therefor.

In Column 17, Line 46, delete "polyacrilin" and insert -- polacrilin --, therefor.

In Column 17, Line 58, delete "annato," and insert -- annatto, --, therefor.

In Column 19, Line 62, delete "acylate," and insert -- acrylate, --, therefor.

In Column 20, Line 1, delete "(e.g. poly" and insert -- (e.g., poly --, therefor.

In Column 21, Lines 36-37, delete "benserezide;" and insert -- benserazide; --, therefor.

In Column 22, Lines 3-4, delete "clomthiazole edisilate," and insert -- clomethiazole edisylate, --, therefor.

In Column 22, Line 5, delete "briveracetam," and insert -- brivaracetam, --, therefor.

Signed and Sealed this
Twentieth Day of August, 2019

Andrei Iancu
*Director of the United States Patent and Trademark Office*

CERTIFICATE OF CORRECTION (continued)

In Column 22, Line 10, delete "fluorocortisone," and insert -- fludrocortisone, --, therefor.

In Column 22, Line 35, delete "(Administracion" and insert -- (Administración --, therefor.

In Column 22, Line 36, delete "Tecnologia Medica," and insert -- Tecnología Médica, --, therefor.

In Column 23, Line 1, delete "memebrane." and insert -- membrane. --, therefor.

In Column 28, Line 13, delete "thilthixene," and insert -- thiothixene, --, therefor.

In Column 28, Lines 13-14, delete "trifluoroperazine," and insert -- trifluoperazine, --, therefor.

In Column 28, Line 21, delete "(SNRT)," and insert -- (SNRI), --, therefor.

In Column 35, under "TABLE 4", Line 61, delete "Tinax0-12 (hours)c" and insert -- Tmax0-12 (hours)c --, therefor.

In Column 36, under "TABLE 4-continued", Line 17, delete "λz(hours-1)" and insert -- λz (hours-1) --, therefor.

In Column 41, Line 59, delete "ng him'"" and insert -- ng.h/mL --, therefor.

In Column 42, Line 40, delete "(AUC0-t)" and insert -- (AUC0-τ) --, therefor.

In Column 46, under "TABLE 12", Line 20, delete "percentagesis" and insert -- percentages is --, therefor.

In Column 46, Line 29, delete "Intent To Treat ("ITT")" and insert -- Intent-To-Treat ("ITT") --, therefor.

In Column 49, under "TABLE 19", Lines 45-46, delete "Parts II 98 Using Stable Dose and III from Baseline to Day" and insert -- Parts II and III from Baseline to Day 98 Using --, therefor.

In Column 49, under "TABLE 19", Line 62, delete "102)" and insert -- 102). --, therefor.

In the Claims

In Column 54, Claim 1, Lines 5-6, delete "comprises" and insert -- comprises: --, therefor.

In Column 54, Claim 2, Line 38, delete "of" and insert -- of: --, therefor.

In Column 54, Claim 2, Line 39, delete "equivalent" and insert -- equivalent; --, therefor.

In Column 55, Claim 13, Line 27, delete "thilthixene," and insert -- thiothixene, --, therefor.

In Column 55, Claim 13, Line 27, delete "trifluoroperazine," and insert -- trifluoperazine, --, therefor.

CERTIFICATE OF CORRECTION (continued)
U.S. Pat. No. 10,213,394 B1

In Column 55, Claim 18, Line 47, delete "devise" and insert -- device --, therefor.

In Column 56, Claim 28, Line 47, delete "of" and insert -- of: --, therefor.

In Column 56, Claim 28, Line 49, delete "equivalent," and insert -- equivalent; --, therefor.